United States Patent
Okada et al.

(10) Patent No.: US 10,882,906 B2
(45) Date of Patent: Jan. 5, 2021

(54) CLAUDIN 5 ANTIBODY, AND MEDICINE CONTAINING SAID ANTIBODY

(71) Applicant: OSAKA UNIVERSITY, Osaka (JP)

(72) Inventors: Yoshiaki Okada, Osaka (JP); Masuo Kondoh, Osaka (JP); Yosuke Hashimoto, Osaka (JP); Keisuke Shirakura, Osaka (JP); Takefumi Doi, Osaka (JP); Kiyohito Yagi, Osaka (JP); Hiroyuki Takeda, Ehime (JP); Tatsuya Sawasaki, Ehime (JP)

(73) Assignee: OSAKA UNIVERSITY, Osaka (JP)

( * ) Notice: Subject to any disclaimer, the term of this patent is extended or adjusted under 35 U.S.C. 154(b) by 0 days.

(21) Appl. No.: 16/467,751

(22) PCT Filed: Dec. 4, 2017

(86) PCT No.: PCT/JP2017/043497
§ 371 (c)(1),
(2) Date: Jun. 7, 2019

(87) PCT Pub. No.: WO2018/105560
PCT Pub. Date: Jun. 14, 2018

(65) Prior Publication Data
US 2020/0223915 A1   Jul. 16, 2020

(30) Foreign Application Priority Data
Dec. 7, 2016 (JP) ................................ 2016-237370

(51) Int. Cl.
*A61K 39/395* (2006.01)
*C07K 16/18* (2006.01)
*C07K 16/28* (2006.01)

(52) U.S. Cl.
CPC .......... *C07K 16/28* (2013.01); *A61K 39/3955* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| 2009/0202556 A1 | 8/2009 | Ohta et al. |
| 2011/0064792 A1 | 3/2011 | Humphries et al. |
| 2016/0222125 A1 | 8/2016 | Sahin et al. |

FOREIGN PATENT DOCUMENTS

| JP | 2003-524384 | 8/2003 |
| JP | 2016-47845 | 4/2016 |
| JP | 2016-525558 | 8/2016 |
| WO | 00/26360 | 5/2000 |
| WO | 2008/114733 | 9/2008 |
| WO | 2009/028663 | 3/2009 |

(Continued)

OTHER PUBLICATIONS

International Search Report dated Feb. 27, 2018 in corresponding International (PCT) Application No. PCT/JP2017/043497.

(Continued)

*Primary Examiner* — Aurora M Fontainhas
(74) *Attorney, Agent, or Firm* — Wenderoth, Lind & Ponack, L.L.P.

(57) ABSTRACT

Provided is a novel technique for controlling the blood-brain barrier. An antibody whose epitope is a region within an extracellular domain of Claudin 5 protein.

15 Claims, 12 Drawing Sheets
Specification includes a Sequence Listing.

(56) References Cited

FOREIGN PATENT DOCUMENTS

| WO | 2011/057788 | 5/2011 |
|---|---|---|
| WO | 2015/014657 | 2/2015 |

OTHER PUBLICATIONS

Liao et al., "Specific Binding of a Mutated Fragment of *Clostridium perfringens* Enterotoxin to Endothelial Claudin-5 and Its Modulation of Cerebral Vascular Permeability", Neuroscience, Apr. 13, 2016, vol. 327, pp. 53-63.

Nitta et al., "Size-selective loosening of the blood-brain barrier in claudin-5-deficient mice", The Journal of Cell Biology, May 12, 2003, vol. 161, No. 3, pp. 653-660.

Protze et al., "Directed structural modification of *Clostridium perfringens* enterotoxin to enhance binding to claudin-5", Cell. Mol. Life Sci., 2015, vol. 72, pp. 1417-1432.

Escudero-Esparza et al., "Claudin-5 is involved in breast cancer cell motility through the N-WASP and ROCK signalling pathways", Journal of Experimental & Clinical Cancer Research, vol. 31, No. 43, 2012, pp. 1-18.

Fofana et al., "Monoclonal Anti-Claudin 1 Antibodies Prevent Hepatitis C Virus Infection of Primary Human Hepatocytes", Gastroenterology, vol. 139, 2010, pp. 953-964.

Campbell et al., "RNAi-mediated reversible opening of the blood-brain barrier", The Journal of Gene Medicine, vol. 10, 2008, pp. 930-947.

Staat et al., "Mode of action of claudin peptidomimetics in the transient opening of cellular tight junction barriers", Biomaterials, vol. 54, 2015, pp. 9-20.

The partial supplementary European search report dated Dec. 20, 2019 in corresponding European Patent Application No. 17878840.2.

Ando et al., "Generation of specific monoclonal antibodies against the extracellular loops of human claudin-3 by immunizing mice with target-expressing cells", Bioscience, Biotechnology, and Biochemistry, 2015, vol. 79, No. 8, pp. 1272-1279.

Li et al., "Development of an Anti-Claudin-3 and -4 Bispecific Monoclonal Antibody for Cancer Diagnosis and Therapy", Journal of Pharmacology and Experimental Therapeutics, 2014, vol. 351, No. 1, pp. 206-213.

Fig. 1

```
Wild-Type Claudin 5  ATGGGGTCCGCAGCGTTGGAGATCCTGGGCCTGGTGCTGTGCCTGGTGGGCTGGGGGGGT  60
Codon Conversion     ATGGGATCTGCTGCTCTTGAGATCCTTGGACTTGTTCTCTGCCTTGTTGGATGGGGAGGA  60
                     ***** ** ** **  * ******** ** ** ** ** ***** ** ** ***** **

Wild-Type Claudin 5  CTGATCCTGGCGTGCGGGCTGCCCATGTGGCAGGTGACCGCCTTCCTGGACCACAACATC  120
Codon Conversion     CTTATCCTTGCTTGCGGACTTCCTATGTGGCAGGTTACAGCTTTCCTCGATCACAACATC  120
                     ** ***** ** ***** ** ** ********** ** ** ***** ** *********

Wild-Type Claudin 5  GTGACGGCGCAGACCACCTGGAAGGGGCTGTGGATGTCGTGCGTGGTGCAGAGCACCGGG  180
Codon Conversion     GTGACTGCTCAGACTACTTGGAAGGGACTCTGGATGTCTTGCGTGGTGCAATCTACTGGA  180
                     ***** ** ***** ** ******** ** ******** **********   ** ** **

Wild-Type Claudin 5  CACATGCAGTGCAAAGTGTACGACTCGGTGCTGGCTCTGAGCACCGAGGTGCAGGCGGCG  240
Codon Conversion     CACATGCAGTGCAAGGTGTACGATTCTGTTCTCGCTCTCTCTACTGAGGTTCAAGCTGCT  240
                     **************  ******* ** **  **  *****    **  *****  ** ** **

Wild-Type Claudin 5  CGGGCGCTCACCGTGAGCGCCGTGCTGCTGGCGTTCGTTGCGCTCTTCGTGACCCTGGCG  300
Codon Conversion     AGGGCTCTTACTGTTTCTGCTGTTCTCCTCGCTTTCGTGGCTCTCTTCGTTACTCTTGCT  300
                     **** ** ** **   ** ** ** ** **  *****  ** ** ******** ** ** **

Wild-Type Claudin 5  GGCGCGCAGTGCACCACCTGCGTGGCCCCGGGCCCGGCCAAGGCGCGTGTGGCCCTCACG  360
Codon Conversion     GGTGCTCAGTGTACTACCTGTGTTGCTCCTGGACCTGCTAAGGCTAGAGTTGCTCTTACA  360
                     ** ** ***** ** ***** ** ** ** ** ** ** *****  * ** ** ** **

Wild-Type Claudin 5  GGAGGCGTGCTCTACCTGTTTTGCGGGCTGCTGGCGCTCGTGCCACTCTGCTGGTTCGCC  420
Codon Conversion     GGTGGTGTGCTCTACCTTTTCTGTGGACTTCTTGCTCTTGTGCCTCTCTGCTGGTTCGCT  420
                     ** ** *********** ** ** ** ** ** ** ** ***** ** ***************

Wild-Type Claudin 5  AACATTGTCGTCCGCGAGTTTTACGACCCGTCTGTGCCCGTGTCGCAGAAGTACGAGCTG  480
Codon Conversion     AACATCGTGGTTAGAGAGTTCTACGATCCTTCTGTGCCTGTGTCTCAGAAGTACGAACTT  480
                     ***** ** **  * ***** ***** ** ******** ***** ********** **

Wild-Type Claudin 5  GGCGCAGCGCTGTACATCGGCTGGGCGGCCACCGCGCTGCTCATGGTAGCGGCTGCCTC  540
Codon Conversion     GGAGCTGCTCTCTACATTGGATGGGCTGCTACTGCTCTCCTTATGGTTGGAGGATGCCTT  540
                     ** ** ** ** ***** ** ***** ** ** ** ** **  ***** ** ** *****

Wild-Type Claudin 5  TTGTGCTGCGGCGCCTGGGTCTGCACCGGCCGTCCCGACCTCAGCTTCCCCGTGAAGTAC  600
Codon Conversion     CTTTGTTGTGGTGCTTGGGTGTGCACTGGAAGGCCTGATTTGTCTTTCCCAGTGAAGTAC  600
                     * ** ** ** ** ***** ***** ** *  * ** **  *  * ***** ********

Wild-Type Claudin 5  TCAGCGCCGCGGCGGCCCACGGCCACCGGCGACTACGACAAGAAGAACTACGTCTGA     657
Codon Conversion     TCTGCTCCTAGAAGGCCTACTGCTACCGGTGATTACGATAAGAAGAACTACGTTTGA     657
                     ** ** **  *  **** ** ** *****  ** ***** ************ ***
```

Fig. 2

```
MGSAALEILGLVLCLVGWVGLILACGLPMWQVTAFLDHNIVTAQTTWKGLWMSC
N-terminal     TM1
VVQSTGHMQCKVYDSVLALSTEVQAARALTVAVLLALVALFVTLTGAQCTTCV
        ECL1                    TM2
APGPVKARVALTGGALYAVCGLLALVPLCWFANIVVREFYDPSVPVSQKYELGA
   ICL              TM3              ECL2
ALYIGWAATALLMGGGLVCCGAWVCTGRPEFSFPVKYSAPRRPTANGDYDKKNYV
           TM4                  C-terminal
```

Fig. 3

```
MGSAALEILGLVLCLVGWGGLILACGLPMWQVTAFLDHNIVTAQTTWKGLWMSCVVQSTGHMQCKVYDSVLALSTEVQAA
RALTVSAVLLAFWGGLILACGLPMWQVTAFLDHNIVTAQTTWKGLWMSCVVQSTGHMQCKVYDSVLALSTEVQAARALT
VSAVLLAFLIALVPLCWFANIVVREFYDPSVPVSQKYELGAALYIGWAATALLMVGLLALVPLCWFANIVVREFYDPSV
PVSQKYELGAALYIGWAATALLMVGWGGLILACGLPMWQVTAFL
```

Fig. 6

```
Human CLDN-5      MGSAALEILGLVLCLVGWGGLILACGLPMWQVTAFLDHNIVTAQTTWKGLWMSCVVQSTG
Cynomolgus CLDN-5 MGSAALEILGLVLCLVGWGGLILACGLPMWQVTAFLDHNIVTAQTTWKGLWMSCVVQSTG
Mouse CLDN-5      MGSAALEILGLVLCLVGWVGLILACGLPMWQVTAFLDHNIVTAQTTWKGLWMSCVVQSTG
Wistar rat CLDN-5 MGSAALEILGLVLCLVGWVGLILACGLPMWQVTAFLDHNIVTAQTTWKGLWMSCVVQSTG
                            68    75
Human CLDN-5      HMQCKVYDSVLALSTEVQAARALTVSAVLLAFVALFVTLAGAQCTTCVAPGPAKARVALT
Cynomolgus CLDN-5 HMQCKVYDSVLALSTEVQAARALTVGAVLLAFVALFVTLAGAQCTTCVAPGPAKARVALT
Mouse CLDN-5      HMQCKVYESVLALSAEVQAARALTVGAVLLALVALFVTLTGAQCTTCVAPGPVKARVALT
Wistar rat CLDN-5 HMQCKVYESVLALSAEVQAARALTVGAVLLALVALFVTLTGAQCTTCVAPGPVKARVALT
                                                        151
Human CLDN-5      GGVLYLFCGLLALVPLCWFANIVVREFYDPSVPVSQKYELGAALYIGWAATALLMVGGCL
Cynomolgus CLDN-5 GGVLYLLCGLLALVPLCWFANIVVREFYDPSVPVSQKYELGAALYIGWAATALLMVGGGL
Mouse CLDN-5      GGALYAVCGLLALVPLCWFANIVVREFYDPTVPVSQKYELGAALYIGWAASALLMCGGGL
Wistar rat CLDN-5 GGALYALCGLLALVPLCWFANIVVREFYDPTVPVSQKYELGAALYIGWAASALLMCGGGL Human CLDN-5      LCCGAWVCTGRPDLSFPVKYSAPRRPTATGDYDKKNYV
Cynomolgus CLDN-5 LCCGAWVCTSRPDLSFPVKYSAPRRPTATGDYDKKNYV
Mouse CLDN-5      VCCGAWVCTGRPEFSFPVKYSAPRRPTANGDYDKKNYV
Wistar rat CLDN-5 VCCGAWVCTGRPEFSFPVKYSAPRRITANGDYDKKNYV
```

Fig. 8

```
Human CLDN-5    MGSAALEILGLVLCLVGWGGLILACGLPMWQVTAFLDHNIVTAQTTWKGLWMSCVVQSTG
Human CLDN-1    MANAGLQLLGFILAFLGWIGAIVSTALPQWRIYSYAGDNIVTAQAMYEGLWMSCVSQSTG
1-1-5           MGSAALEILGLVLCLVGWGGLILACALPQWRIYSYAGDNIVTAQAMYEGLWMSCVSQSTG
1-5-5           MGSAALEILGLVLCLVGWGGLILACALPQWRIYSYAGDNIVTAQAMYEGLWMSCVVQSTG
5-1-5           MGSAALEILGLVLCLVGWGGLILACGLPMWQVTAFLDHNIVTAQTTWKGLWMSCVSQSTG
5-5-1           MGSAALEILGLVLCLVGWGGLILACGLPMWQVTAFLDHNIVTAQTTWKGLWMSCVVQSTG
                                     68        75
Human CLDN-5    HMQCKVYDSVLALSTEVQAARALTVSAVLLAFVALFVTLAGAQCTTCVAPGPAKARVALT
Human CLDN-1    QIQCKVFDSLLNLSSTLQATRALMVVGILLGVIAIFVATVGMKCMKCLEDDEVQKMRMAV
1-1-5           QIQCKVFDSLLNLSSTVQAARALTVSAVLLAFVALFVTLAGAQCTTCVAPGPAKARVALT
1-5-5           HMQCKVYDSVLALSTEVQAARALTVSAVLLAFVALFVTLAGAQCTTCVAPGPAKARVALT
5-1-5           QIQCKVFDSLLNLSSTVQAARALTVSAVLLAFVALFVTLAGAQCTTCVAPGPAKARVALT
5-5-1           HMQCKVYDSVLALSTEVQAARALTVSAVLLAFVALFVTLAGAQCTTCVAPGPAKARVALT
                                                   151
Human CLDN-5    GGVLYLFCGLLALVPLCWFANIVVREFYDPSVPVSQKYELGAALYIGWAATALLMVGGCL
Human CLDN-1    IGGAIFLLAGLAILVATAWYGNRIVQEFYDPMTPVNARYEFGQALFTGWAAASLCLLGGA
1-1-5           GGVLYLFCGLLALVPLCWFANIVVREFYDPSVPVSQKYELGAALYIGWAATALLMVGGCL
1-5-5           GGVLYLFCGLLALVPLCWFANIVVREFYDPSVPVSQKYELGAALYIGWAATALLMVGGCL
5-1-5           GGVLYLFCGLLALVPLCWFANIVVREFYDPSVPVSQKYELGAALYIGWAATALLMVGGCL
5-5-1           GGVLYLFCGLLALVPLCWFANIVVREFYDPMTPVNARYEFGQALYIGWAATALLMVGGCL Human CLDN-5    LCCGAWVCTGRPDLSFPVKYSAPRRPTATGDYDKKNYV
Human CLDN-1    LLCCSCPRKTTSYPTPRPYPKPAPSSGKDYV
1-1-5           LCCGAWVCTGRPDLSFPVKYSAPRRPTATGDYDKKNYV
1-5-5           LCCGAWVCTGRPDLSFPVKYSAPRRPTATGDYDKKNYV
5-1-5           LCCGAWVCTGRPDLSFPVKYSAPRRPTATGDYDKKNYV
5-5-1           LCCGAWVCTGRPDLSFPVKYSAPRRPTATGDYDKKNYV
```

CLAUDIN 5 ANTIBODY, AND MEDICINE CONTAINING SAID ANTIBODY

TECHNICAL FIELD

The present invention relates to a Claudin 5 antibody, and a medicine comprising the antibody. More specifically, the present invention relates to an antibody that recognizes extracellular regions of Claudin 5, a medicine for controlling the blood-brain barrier, and the like.

BACKGROUND ART

The blood-brain barrier is a mechanism that limits material exchange between the blood and brain, and plays an important role in protecting the brain from invasion of foreign substances. On the other hand, the blood-brain barrier interferes with the transfer of intravenously administered drugs to the brain, thus greatly hindering the development of drugs for the treatment of brain diseases. This function of the blood-brain barrier is created by a high level of tight junctions formed between brain capillary endothelial cells, and differs greatly from peripheral capillary endothelial cells in other organs that allow for material permeation. A method of administering mannitol hypertonic solution via the carotid artery was clinically accepted as a methodology to open the tight junctions that limit this material transfer, and to deliver drugs into the brain through the intercellular space. However, this method has large side effects because it is mediated through the destruction of physical cell morphology by cell dehydration. Therefore, developing a new technology that specifically controls only tight junctions is desired.

Claudin family molecules play critical roles in the formation of tight junctions between epithelial cells and vascular endothelial cells. The Claudin family consists of members of 27 four-pass transmembrane proteins with two extracellular loops (first and second extracellular loops from the N-terminal side), and interactions between these cells contribute to tight junction assembly. Different types (composition ratios) and amounts of Claudin family molecules are expressed in different tissues, and this difference creates tissue-specific tight junctions and barrier functions. In particular, in tight junctions between cerebrovascular endothelial cells, Claudin 5 is highly expressed to produce a function of the blood-brain barrier. In fact, in Claudin 5-deficient mice, the function of the blood-brain barrier is partially lost, and permeation of materials with a molecular weight of 1000 or less is permitted. It has also been reported that intravenous administration of Claudin 5 siRNA to mice induces extravasation of materials with a molecular weight of 1000 or less due to siRNA-mediated decreased expression of Claudin 5 in cerebrovascular endothelial cells, and that there are no serious side effects (NFL 1). From these findings, it is expected that the functional control of Claudin 5 will become a new intracerebral drug delivery strategy through the intercellular space.

Several Claudin 5-interacting molecules have been produced thus far for the purpose of inhibiting barrier function by Claudin 5. For example, there has been a report on peptides and antibodies that regulate cellular sealing of Claudin family molecules; however, this report does not show verified data concerning blood-brain barrier control by Claudin 5 antibodies (PTL 1), As another example, it has been reported that peptides derived from the partial sequence of the first extracellular loop of Claudin 1 (about 20 amino acids) can be used to control the barriers of mouse cerebral capillary endothelial cells by inhibiting the interaction of Claudin 1 and Claudin 5 (NPL 2). It has also been reported that a Claudin 5-binding molecule is created by introducing a mutation in the C-terminal of *Clostridium perfringens* enterotoxin, which is known as a molecule that binds to Claudin 3 and Claudin 4, and has a high barrier control activity (NPL 3), However, these molecules have poor binding specificity to Claudin 5 and bind to other Claudin molecules. Due to these problems, developing blood-brain barrier control techniques using these molecules is considered very difficult in terms of enhanced barrier control activity and reduced side effects.

CITATION LIST

Patent Literature

PTL 1: JP2003-524384A

Non-Patent Literature

NPL 1: Matthew Campbell, Anna-Sophia Kiang, Paul F. Kenna, Christian Kerskens, Christoph Blau, Laurence O'Dwyer, Amanda Tivnan, Julie Anne Kelly, Brenda Brankin, Gwyneth-Jane Farrar, Peter Humphries, RNA-mediated reversible opening of the blood-brain barrier, The Journal of Gene Medicine 10 (2008) 930-947.

NPL 2: Christian Staat, Caroline Coisne, Sebastian Dabrowski, Svetlana M. Stamatovic, Anuska V. Andjelkovic, Hartwig Wolburg, Britta Engelhardt, Ingolf E. Blasig, Mode of action of claudin peptidomimetics in the transient opening of cellular tight junction barriers, Biomaterials 54 (2015) 9-20.

NPL 3: Jonas Protze, Miriam Eichner, Anna Piontek, Stefan Dinter, Jan Rossa, Kinga Grazyna Blecharz, Peter Vajkoczy, Joerg Piontek, Gerd Krause, Directed structural modification of *Clostridium perfringens* enterotoxin to enhance binding to claudin-5, Cellular and Molecular Life Sciences 72 (2015) 1417-1432

SUMMARY OF INVENTION

Technical Problem

An object of the present invention is to provide a novel monoclonal antibody that has high Claudin 5 specificity and that recognizes the extracellular domain of Claudin 5. Another object of the present invention is to provide a technique for detecting Claudin 5-expressing cells using this antibody, and a technique for controlling the blood-brain barrier.

Solution to Problem

There are no examples in which binding molecules highly specific to Claudin 5 are produced, and in which their beneficial activity, preferably activity to control the blood-brain barrier, is demonstrated. Some reasons for this are as follows: Claudin 5 is a membrane protein; it is difficult to purify Claudin 5 in terms of solubility and aggregation; and it is not possible to obtain screening materials and immunogens of sufficient quality and quantity for use in the phage display method. As a result of intensive studies in view of the above object, the present inventors succeeded in producing an antibody whose epitope is a region within the extracellular domain of Claudin 5 protein (also referred to as "the antibody of the present invention," "the Claudin 5 extracellular domain antibody," etc., in the present specification). Further, the present inventors surprisingly found that the antibody of the present invention has the effect of opening junctions between cerebrovascular endothelial cells, i.e., blood-brain barrier control activity. As a result of further research based on this finding, the present invention has been completed.

Specifically, the present invention includes the following aspects as embodiments:

Item 1. An antibody that recognizes an epitope region within an extracellular domain of Claudin 5 protein.

Item 2. The antibody according to Item 1, wherein the epitope region is at least one member selected from the group consisting of a region within a first extracellular loop C terminal side of Claudin 5 protein, a region within a second extracellular loop of Claudin 5 protein, and a three-dimensional structure formed from the first extracellular loop and the second extracellular loop.

Item 3. The antibody according to Item 1 or 2, wherein the epitope region is a region within the second extracellular loop of Claudin 5 protein.

Item 4. The antibody according to Item 3, wherein the epitope region is a region containing 151st amino acid from the N-terminal in human Claudin 5 protein comprising the amino acid sequence represented by SEQ ID NO: 73, or an amino acid in another Claudin 5 protein corresponding to the 151st amino acid.

Item 5. The antibody according to Item 3 or 4, wherein the affinity of the antibody to human Claudin 5 protein point mutant S151T comprising the amino acid sequence represented by SEQ ID NO: 99 is ⅕ or less of the affinity thereof to human Claudin 5 protein comprising the amino acid sequence represented by SEQ ID NO: 73.

Item 6. The antibody according to Item 1 or 2, wherein the epitope region is a three-dimensional structure formed from the first extracellular loop and second extracellular loop of Claudin 5 protein.

Item 7. The antibody according to any one of Items 1 to 6, wherein the affinity of the antibody to Claudin family proteins other than Claudin 5 protein is ⅕ or less of the affinity thereof to Claudin 5 protein.

Item 8. The antibody according to any one of Items 1 to 7, which is selected from the group consisting of the following antibodies A to I:

(A) antibody A comprising:
a heavy-chain variable region comprising:
heavy-chain CDR1 comprising the amino acid sequence represented by SEQ ID NO: 1,
heavy-chain CDR2 comprising the amino acid sequence represented by SEQ ID NO: 2, and
heavy-chain CDR3 comprising the amino acid sequence represented by SEQ ID NO: 3; and/or
a light-chain variable region comprising:
light-chain CDR1 comprising the amine acid sequence represented by SEQ ID NO: 5,
light-chain CDR2 comprising the amino acid sequence represented by SEQ ID NO: 6, and
light-chain CDR3 comprising the amino acid sequence represented by SEQ ID NO: 7;

(B) antibody B comprising:
a heavy-chain variable region comprising:
heavy-chain CDR1 comprising the amino acid sequence represented by SEQ ID NO: 9,
heavy-chain CDR2 comprising the amino acid sequence represented by SEQ ID NO: 10, and
heavy-chain CDR3 comprising the amino acid sequence represented by SEQ ID NO: 11, and/or
a light-chain variable region comprising:
light-chain CDR1 comprising the amino acid sequence represented by SEQ ID NO: 13,
light-chain CDR2 comprising the amino acid sequence represented by SEQ ID NO: 14, and
light-chain CDR3 comprising the amino acid sequence represented by SEQ ID NO: 15;

(C) antibody C comprising:
a heavy-chain variable region comprising:
heavy-chain CDR1 comprising the amino acid sequence represented by SEQ ID NO: 17,
heavy-chain CDR2 comprising the amino acid sequence represented by SEQ ID NO: 18, and
heavy-chain CDR3 comprising the amino acid sequence represented by SEQ ID NO: 19; and/or
a light-chain variable region comprising:
light-chain CDR1 comprising the amino acid sequence represented by SEQ ID NO: 21,
light-chain CDR2 comprising the amino acid sequence represented by SEQ ID NO: 22, and
light-chain CDR3 comprising the amino acid sequence represented by SEQ ID NO: 23;

(D) antibody D comprising:
a heavy-chain variable region comprising:
heavy-chain CDR1 comprising the amino acid sequence represented by SEQ ID NO: 25,
heavy-chain CDR2 comprising the amino acid sequence represented by SEQ ID NO: 26, and
heavy-chain CDR3 comprising the amino acid sequence represented by SEQ ID NO: 27; and/or
a light-chain variable region comprising:
light-chain CDR1 comprising the amino acid sequence represented by SEQ ID NO: 29,
light-chain CDR2 comprising the amino acid sequence represented by SEQ ID NO: 30, and
light-chain CDR3 comprising the amino acid sequence represented by SEQ ID NO: 31;

(E) antibody E comprising:
a heavy-chain variable region comprising:
heavy-chain CDR1 comprising the amino acid sequence represented by SEQ ID NO: 33,
heavy-chain CDR2 comprising the amino acid sequence represented by SEQ ID NO: 34, and
heavy-chain CDR3 comprising the amino acid sequence represented by SEQ ID NO: 35; and/or
a light-chain variable region comprising:
light-chain CDR1 comprising the amino acid sequence represented by SEQ ID NO: 37,
light-chain CDR2 comprising the amino acid sequence represented by SEQ 1D NO: 38, and
light-chain CDR3 comprising the amino acid sequence represented by SEQ ID NO: 39;

(F) antibody F comprising:
a heavy-chain variable region comprising:
heavy-chain CDR1 comprising the amino acid sequence represented by SEQ ID NO; 41,
heavy-chain CDR2 comprising the amino acid sequence represented by SEQ ID NO: 42, and
heavy-chain CDR3 comprising the amino acid sequence represented by SEQ ID NO: 43; and/or
a light-chain variable region comprising:
light-chain CDR1 comprising the amino acid sequence represented by SEQ ID NO: 45,
light-chain CDR2 comprising the amino acid sequence represented by SEQ ID NO: 46, and
light-chain CDR3 comprising the amino acid sequence represented by SEQ ID NO: 47;

(G) antibody G comprising:
a heavy-chain variable region comprising:
heavy-chain CDR1 comprising the amino acid sequence represented by SEQ ID NO: 49,
heavy-chain CDR2 comprising the amino acid sequence represented by SEQ ID NO: 50, and
heavy-chain CDR3 comprising the amino acid sequence represented by SEQ ID NO; 51; and/or
a light-chain variable region comprising:
light-chain CDR1 comprising the amino acid sequence represented by SEQ ID NO: 53,
light-chain CDR2 comprising the amino acid sequence represented by SEQ ID NO: 54, and
light-chain CDR3 comprising the amino acid sequence represented by SEQ ID NO: 55;
(H) antibody H comprising:
a heavy-chain variable region comprising:
heavy-chain CDR1 comprising the amino acid sequence represented by SEQ ID NO: 57,
heavy-chain CDR2 comprising the amino acid sequence represented by SEQ ID NO: 58, and
heavy-chain CDR3 comprising the amino acid sequence represented by SEQ ID NO: 59; and/or
a light-chain variable region comprising:
light-chain CDR1 comprising the amino acid sequence represented by SEQ ID NO: 61,
light-chain CDR2 comprising the amino acid sequence represented by SEQ ID NO: 62, and
light-chain CDR3 comprising the amino acid sequence represented by SEQ ID NO: 63; and
(I) antibody I comprising:
a heavy-chain variable region comprising:
heavy-chain CDR1 comprising the amino acid sequence represented by SEQ ID NO: 65,
heavy-chain CDR2 comprising the amino acid sequence represented by SEQ ID NO: 66, and
heavy-chain CDR3 comprising the amino acid sequence represented by SEQ ID NO: 67; and/or
a light-chain variable region comprising:
light-chain CDR1 comprising the amino acid sequence represented by SEQ ID NO: 69,
light-chain CDR2 comprising the amino acid sequence represented by SEQ ID NO: 70, and
light-chain CDR3 comprising the amino acid sequence represented by SEQ ID NO: 71.

Item 9. The antibody according to any one of Items 1 to 8, which is a monoclonal antibody.

Item 10. A polynucleotide that encodes the antibody according to any one of Items 1 to 9.

Item 11. A cell comprising the polynucleotide according to Item 10.

Item 12. A complex of the antibody according to any one of Items 1 to 9 and a drug.

Item 13. A medicine comprising at least one member selected from the group consisting of the antibody according to any one of Items 1 to 9 and the complex according to Item 12.

Item 14A. The medicine according to Item 13, which is for blood-brain barrier control.

Item 14B. The medicine according to Item 13, which is for cerebrovascular endothelial cell layer barrier function control.

Item 14O. The medicine according to Item 13, which is for promotion of drug permeation through the blood-brain barrier.

Item 14A1. At least one member selected from the group consisting of the antibody according to any one of Items 1 to 9 and the composite according to Item 12, for use in blood-brain barrier control.

Item 14B1. At least one member selected from the group consisting of the antibody according to any one of Items 1 to 9 and the composite according to Item 12, for use in cerebrovascular endothelial cell layer barrier function control.

Item 14C1. At least one member selected from the group consisting of the antibody according to any one of Items 1 to 9 and the composite according to Item 12, for use in promotion of drug permeation through the blood-brain barrier.

Item 14A2. Use of at least one member selected from the group consisting of the antibody according to any one of Items 1 to 9 and the composite according to Item 12, for production of a medicine for blood-brain barrier control.

Item 14B2. Use of at least one member selected from the group consisting of the antibody according to any one of Items 1 to 9 and the complex according to Item 12, for production of a medicine for cerebrovascular endothelial cell layer barrier function control.

Item 14C2. Use of at least one member selected from the group consisting of the antibody according to any one of Items 1 to 9 and the complex according to Item 12, for production of a medicine for promoting drug permeation through the blood-brain barrier.

Item 14A3. A blood-brain barrier control method, comprising administering, to a patient, at least one member selected from the group consisting of the antibody according to any one of Items 1 to 9 and the complex according to Item 12.

Item 14B3. A cerebrovascular endothelial cell layer barrier function control method, comprising administering, to a patient, at least one member selected from the group consisting of the antibody according to any one of Items 1 to 9 and the complex according to Item 12.

Item 14C3. A method for promoting drug permeation through the blood-brain barrier, comprising administering, to a patient, at least one member selected from the group consisting of the antibody according to any one of items 1 to 9 and the complex according to Item 12.

Item 15. A reagent comprising at least one member selected from the group consisting of the antibody according to any one of Items 1 to 9 and the complex according to Item 12.

Advantageous Effects of Invention

The monoclonal antibody obtained by the present invention, which recognizes extracellular regions of Claudin 5, has high Claudin specificity, unlike existing molecules binding to extracellular regions of Claudin 5. Accordingly, a small population of cells expressing Claudin 5 can be detected and isolated without immobilization and permeabilization of the cells. The antibody obtained by the present invention can also be used academically. Vascular endothelial cells, including cerebrovascular endothelial cells, are known to be a heterogeneous group; however, the use of the antibody obtained by the present invention makes it possible to, for example, analyze these cells after grouping depending on the difference in the expression levels of Claudin 5. Thus, the antibody of the present invention can serve as a valuable reagent for unraveling the mechanism of the blood-brain barrier, and the understanding of pathological breakdown.

The antibody developed in the present invention has the activity to control barriers formed by tight junctions formed by cerebrovascular endothelial cells, whereby the passage of a drug through the blood-brain barrier can be facilitated, for example, by co-administration of the antibody with the drug or by administration of a complex of the drug and the antibody. Eventually, it becomes possible to further enhance preventive or therapeutic effects of the drug against diseases, such as central nervous system diseases.

The present invention can provide an antibody against the extracellular domain of Claudin 5 as a novel antibody, and can thus contribute to studies on Claudin 5, blood-brain barrier, and the like.

BRIEF DESCRIPTION OF DRAWINGS

FIG. 1 illustrates a comparison between the coding sequence of Claudin 5 from human cDNA (SEQ ID NO:100), and the coding sequence of the Claudin 5 after codon conversion (SEQ ID NO:74). The upper row shows the coding sequence of Claudin 5 from human cDNA, and the lower row shows the coding sequence of Claudin 5 after codon conversion. The asterisks indicate a base that remains the same before and after conversion.

FIG. 2 illustrates a sequence of human-mouse-chimeric Claudin 5 protein (SEQ ID NO:75). The sequences of the extracellular loops (ECLs) and their neighboring transmembrane regions (TMs, underlined) of mouse Claudin 5 protein have been replaced with those from human Claudin 5. The amino acid residues that have been changed from those of the mouse sequence to the residues of the human sequence are indicated within red squares. The portion deleted from the intracellular C-terminal region of the chimeric Claudin 5 protein is indicated by hatching (residues 190 to 218 of SEQ ID NO:90).

FIG. 3 illustrates the sequence of extracellular domain reversible Claudin 5 protein (SEQ ID NO:77). The portion underlined in red indicates the first extracellular loop, and the portion double-underlined in blue indicates the second extracellular loop, with the portions enclosed in boxes indicating the transmembrane regions.

FIG. 6 illustrates a comparison of the amino acid sequence of Claudin 5 protein between a variety of species (SEQ ID NOs:73, 92, 90, and 91). Amino acids that differ between species are underlined in red. The figures above the sequences indicate amino acid numbers counted from the N-terminal.

FIG. 8 illustrates a comparison of the amino acid sequence between human Claudin proteins (SEQ ID NOs:73 and 79) and chimeric proteins (SEQ ID NOs:93, 94, 95 ,and 96) The sequence of human Claudin 1 is underlined in red. The figures above the sequences indicate amino acid numbers counted from the N-terminal.

DESCRIPTION OF EMBODIMENTS

1. Definition

Figure 4:
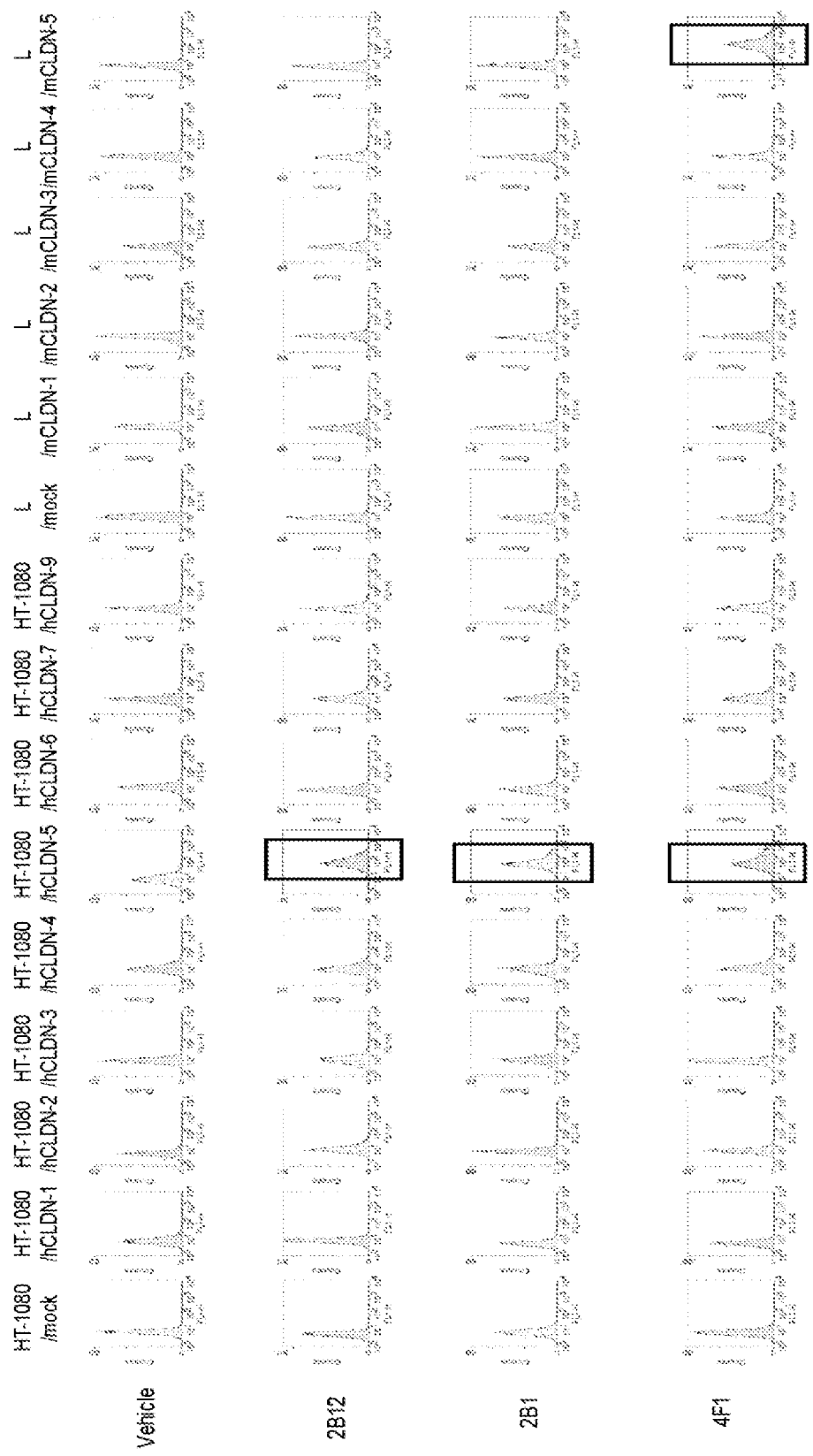
FIG. 4 illustrates FACS histograms showing the results of specificity analysis (Example 3) of the antibodies obtained in Example 1. Shown at the top of the histograms are the name of the cell lines used (HT-1080 or L), and the name of the Claudin proteins expressed in the cells using a retrovirus (h denotes human abbreviation, m denotes mouse abbreviation, CLDN denotes Claudin abbreviation, and mock denotes retrovirus-infected cells that do not express Claudin protein). The antibodies used as a primary antibody are shown on the leftmost side of the histograms. In each histogram, the horizontal axis represents the fluorescence signal, and the vertical axis represents the cell count. Peaks that are shifted to the right (on the side of stronger fluorescent signals), as compared with peaks of the case in which the antibody was not reacted (vehicle), are indicated within square boxes.

In the present specification, the terms "comprise" and "contain" include the concepts "comprise," "contain," "substantially consist of," and "consist of."

The "identity" of amino acid sequences refers to the degree of consistency between two or more amino acid sequences that can be compared with each other. Thus, the higher the consistency between two amino acid sequences, the higher the identity or similarity between these sequences. Levels of amino acid sequence identity are determined using default parameters using, for example, FASTA, which is a sequence analysis tool. Alternatively, identity levels can be determined using the algorithm BLAST developed by Karlin and Altschul (Karlin S, Altschul S F, "Methods for assessing the statistical significance of molecular sequence features by using general scoring schemes," Proc Natl Acad Sci USA, 87: 2264-2268 (1990); Karlin S, Altschul S F, "Applications and statistics for multiple high-scoring segments in molecular sequences," Proc Natl Acad Sci USA, 90 5873-7 (1993)). A program called BLASTX based on this BLAST algorithm has been developed. Specific techniques for these analysis methods are known, and reference may be made to the National Center of Biotechnology Information (NCBI) website (http://www.ncbi.nlm.nih.gov/). The "identity" of base sequences is also defined as described above.

In the present specification, "conservative substitution" means that an amino acid residue is replaced by an amino acid residue having a similar side chain. Examples of conservative substitutions include substitution between amino acid residues having a basic side chain, such as lysine, arginine, and histidine. Other conservative substitutions include substitution between amino acid residues having an acidic side chain, such as aspartic acid and glutamic acid; substitution between amino acid residues having an uncharged polar side chain, such as glycine, asparagine, glutamine, serine, threonine, tyrosine, and cysteine; substitution between amino acid residues having a non-polar side chain, such as alanine, valine, leucine, isoleucine, proline, phenylalanine, methionine, and tryptophan; substitution between amino acid residues having a β-branched side chain, such as threonine, valine, and isoleucine; and substitution between amino acid residues having an aromatic side chain, such as tyrosine, phenylalanine, tryptophan, and histidine.

In the present specification, "CDR" is an abbreviation for complementarity determining region, and is also referred to as complementarity determining region, CDR is a region that is present in the variable region of immunoglobulin, and that is deeply involved in the specific binding of antibodies to antigens. "Light-chain CDR" refers to CDR present in the variable region of the light chain of immunoglobulin, and "heavy-chain CDR" refers to CDR present in the variable region of the heavy chain of immunoglobulin.

In the present specification, the "variable region" refers to a region including CDR1 to CDR3 (hereinafter simply referred to as "CDRs 1-3") described above. The arrangement order of these CDRs 1-3 is not limited. Preferably, in this region, CDR1, CDR2, and CDR3 are arranged in this order in the N-terminal to C-terminal direction, or vice versa, via other continuous amino acid sequences or other amino acid sequences called framework regions (FRs) described below. The "heavy-chain variable region" is a region in which the above heavy-chain CDRs 1-3 are arranged, and the "light-chain variable region" is a region in which the above light-chain CDRs 1-3 are arranged.

The regions of each variable region other than the above-mentioned CDRs 1-3 are called framework regions (FRs), as described above. Specifically, a region between the N-terminal of the variable region and CDR1 is defined as FR1, a region between CDR1 and CDR2 is defined as FR2, a region between CDR2 and CDR3 is defined as FR3, and a region between CDR3 and the C-terminal of the variable region is defined as FR4.

FRs are regions that also function as linker sequences that connect CDRs 1-3 of particular importance as antigen-recognition sequences described above, and that contribute to the three-dimensional formation of the entire variable regions.

2. Antibody

As one embodiment, the present invention relates to an antibody that recognizes an epitope region within the extracellular domain of Claudin 5 protein (also referred to as "the antibody of the present invention," "Claudin 5 extracellular domain antibody," etc., in the present specification). This will be described below.

Claudin 5 protein is an expression product of Claudin 5 (also referred to as CLDN 5 or Cldn 5) gene, and is expressed in organisms. The organism species from which Claudin 5 protein is derived are not limited. Examples include various mammals, such as humans, monkeys, mice, rats, dogs, cats, rabbits, pigs, horses, cows, sheep, goats, and deer.

The amino acid sequences of Claudin 5 proteins derived from various organism species are known. Specifically, examples of human Claudin 5 protein include a protein comprising the amino acid sequence represented by SEQ ID NO 73, examples of mouse Claudin 5 protein include a protein comprising the amino acid sequence represented by SEQ ID NO: 90, examples of rat Claudin 5 protein include a protein comprising the amino acid sequence represented by SEQ ID NO: 91, and examples of monkey Claudin 5 protein include a protein comprising the amino acid sequence represented by SEQ ID NO: 92.

Claudin 5 protein may have amino acid mutations, such as substitution, deletion, addition, and insertion, as long as their original activity is not impaired, and Claudin 5 proteins can interact with each other via their extracellular loops to form tight junctions. The mutation is preferably substitution, and more preferably conservative substitution, in terms of less susceptibility to loss of activity.

Preferable specific examples of Claudin 5 protein include at least one member selected from the group consisting of a protein described in (a) below and a protein described in (b) below:

(a) a protein comprising the amino acid sequence represented by any of SEQ ID NOs: 73 and 90 to 92; and (b) a protein comprising an amino acid sequence having 85% or more identity to the amino acid sequence represented by any of SEQ ID NOs: 73 and 90 to 92, and having tight junction-forming ability.

In the above (b), the identity is more preferably 90% or more, even more preferably 95% or more, and still more preferably 98% or more.

Examples of the protein described in (b) above include:

(b') a protein comprising an amino acid sequence with substitution, deletion, addition, or insertion of one or more amino acids in the amino acid sequence represented by any of SEQ ID NOs: 73 and 90 to 92, and having inositol phosphate bond hydrolysis activity.

In the above (b'), the number of "more amino acids" is, for example, 2 to 20, preferably 2 to 10, more preferably 2 to 5, and even more preferably 2 or 3.

The extracellular domain of Claudin 5 protein is an extracellularly exposed region in a state in which the Claudin 5 protein four times penetrates the cell membrane (preferably endothelial cell membrane, more preferably vascular endothelial cell membrane, and even more preferably brain capillary endothelial cell membrane). The extracellular domain of Claudin 5 protein is not limited to that extent. The extracellular domain of Claudin 5 protein consists of a first extracellular loop present on the N-terminal side, and a second extracellular loop present on the C-terminal side. The extracellular domain of each Claudin 5 protein, as well as the first extracellular loop and the second extracellular loop, are already known or can be easily determined using various transmembrane region prediction tools (e.g., SOSUI http://harrier.nagahama-i-bio.ac.jp/sosui/).

Examples of the extracellular domain include, for example, in human Claudin 5 protein comprising the amino acid sequence represented by SEQ ID NO: 73, a region from 28th amino acid (proline) to 80th amino acid (alanine) from the N-terminal (first extracellular loop), and a region from 147th amino acid (phenylalanine) to 163rd amino acid (alanine) from the N-terminal (second extracellular loop). Specific examples of the extracellular domain of other types of Claudin 5 protein include regions corresponding to these regions. In the present specification, the phrase "regions corresponding to" refers to, for example, corresponding regions when the amino acid sequence of human Claudin 5 protein is compared with the amino acid sequence of another type of Claudin 5 using a sequence analysis tool (FASTA, BLAST, etc.).

The antibody of present invention recognizes an epitope region within the extracellular domain of Claudin 5 protein (also referred to simply as the "epitope" in the present specification). In other words, the antibody of the present invention binds to, or has affinity to, a region within the extracellular domain of Claudin 5 protein.

The epitope of the antibody of the present invention is not limited, and may be a linear epitope or a three-dimensional epitope. When the epitope is a linear epitope, the "region within the extracellular domain of Claudin 5 protein" as the epitope is a contiguous amino acid sequence. When the epitope is a three-dimensional epitope, the "region within the extracellular domain of Claudin 5 protein" as the epitope may be a contiguous amino acid sequence or a plurality of non-contiguous amino acid sequences.

The number of amino acid residues constituting the epitope is not limited, and is, for example, 40 or less, 35 or less, 6 to 30, 6 to 25, 6 to 20, 6 to 15, or 6 to 10.

Preferable specific examples of the epitope of the antibody of the present invention include a region within the C-terminal side of the first extracellular loop, a region within the second extracellular loop, a three-dimensional structure formed from the first extracellular loop and the second extracellular loop, and the like.

Examples of the region within the C-terminal side of the first extracellular loop, which is a preferable specific example of the epitope, include a region comprising ⅔ of the amino acid sequence on the C-terminal side when the amino acid sequence constituting the first extracellular loop is divided into three, and a region comprising half of the amino acid sequence on the C-terminal side when the amino acid sequence constituting the first extracellular loop is divided into two. More specifically, for example, in human Claudin 5 protein comprising the amino acid sequence represented by SEQ ID NO 73, a region from 46th amino acid to 80th amino acid from the N-terminal is preferable, and a region from 55th amino acid to 80th amino acid from the N-terminal is more preferable.

Examples of the region within the second extracellular loop, which is a preferable specific example of the epitope, include, for example, in human Claudin 5 protein comprising the amino acid sequence represented by SEQ ID NO: 73, a region from 147th amino acid (phenylalanine) to 163rd amino acid (alanine) from the N-terminal, and preferably a region containing 151st amino acid (serine) from the N-terminal. Specific examples of other Claudin 5 proteins include regions corresponding to these regions.

When the epitope of the antibody of the present invention is a region within the second extracellular loop, preferable embodiments of the antibody against human Claudin 5 protein include antibodies whose affinity to human Claudin 5 protein point mutant S151T comprising the amino acid sequence represented by SEQ ID NO: 99 (Example 6) is ⅕ or less, 1/20 or less, 1/100 or less, 1/500 or less, 1/2000 or less, or 1/10000 or less, of the affinity thereof to human Claudin 5 protein comprising the amino acid sequence represented by SEQ ID NO: 73; and preferable embodiments of the antibody against other Claudin 5 proteins include antibodies whose affinity to a point mutant corresponding to the above point mutant is ⅕ or less, 1/20 or less, 1/100 or less, 1/500 or less, 1/2000 or less, or 1/10000 or less, of the affinity thereof to wild-type Claudin 5 protein.

When the epitope of the antibody of the present invention is a region within the second extracellular loop, preferable embodiments of the antibody against human Claudin 5 protein include antibodies having affinity to human Claudin 5 protein point mutants comprising the amino acid sequences represented by SEQ ID NOs: 97 and/or 98 (D68E and T75A: Example 6); and preferable embodiments of the antibody against other Claudin 5 proteins include antibodies having affinity to point mutants corresponding to the above point mutants.

The affinity of the test antibody to the target Claudin protein can be examined by fluorescently staining cells expressing the target Claudin protein using the test antibody (or a solution used to dilute the antibody), and analyzing the fluorescently stained cells by FACS, in the same manner as in Examples 1 to 4. The sum of the fluorescent signals of the cells can be regarded as the affinity of the test antibody to the target Claudin protein. When the sum of fluorescent signals when the test antibody is used is 1.5, 2, 5, 10, 20, 50, 100, 200, 500, 1000, 5000, or 10000 times or more the sum of fluorescent signals when a diluent of the antibody is used (vehicle), the test antibody can be determined to "have affinity" to the target protein. Regarding the affinity, the same applies to the following.

When the antibody of present invention is an antibody against human Claudin 5 protein, having an epitope that is a region within the second extracellular loop, preferable embodiments include antibodies whose affinity to a human Claudin 5 protein mutant comprising the amino acid sequence represented by SEQ ID NO: 96 (5-5-1: Example 5) is 1/5 or less, 1/20 or less, 1/100 or less, 1/500 or less, 1/2000 or less, or 1/10000, or less of the affinity thereof to human Claudin 5 protein comprising the amino acid sequence represented by SEQ ID NO: 73.

When the antibody of present invention is an antibody against human Claudin 5 protein, having an epitope that is a region within the second extracellular loop, preferable embodiments includes antibodies having affinity to human Claudin 5 protein mutants comprising the amino acid sequences represented by SEQ ID NOs: 93 to 95 (1-1-5, 1-5-5, and/or 5-1-5: Example 5).

Examples of the three-dimensional structure formed from the first extracellular loop and the second extracellular loop, which is a preferable specific example of the epitope, include, for example, in human Claudin 5 protein comprising the amino acid sequence represented by SEQ ID NO: 73, a three-dimensional structure formed from a region from 28th amino acid (proline) to 80th amino acid (alanine) from the N-terminal, and a region from 147th amino acid (phenylalanine) to 163rd amino acid (alanine) from the N-terminal; preferably a three-dimensional structure formed from a region from 28th amino acid (praline) to 67th amino acid (tyrosine) from the N-terminal, and a region from 147th amino acid (phenylalanine) to 163rd amino acid (alanine) from the N-terminal; more preferably a three-dimensional structure formed from a region from 28th amino acid (proline) to 55th amino acid (valine) from the N-terminal, and a region from 147th amino acid (phenylalanine) to 163rd amino acid (alanine) from the N-terminal; and even more preferably a three-dimensional structure formed from a region from 28th amino acid 28 (proline) to 48th amino acid (lysine) from the N-terminal, and a region from 147th amino acid (phenylalanine) to 163rd amino acid (alanine) from the N-terminal. Specific examples of other types of Claudin 5 proteins include regions corresponding the above regions.

When the epitope of the antibody of the present invention is a three-dimensional structure formed from the first extracellular loop and the second extracellular loop, preferable embodiments of the antibody against human Claudin 5 protein include antibodies having affinity to human Claudin 5 protein point mutants comprising the amino acid sequence represented by
SEQ ID NOs: 97 to 99 (D68E, T75A, and/or S151T: Example 6); and preferable embodiments of the antibody against other Claudin 5 proteins include antibodies having affinity to point mutants corresponding to the above point mutants.

When the antibody of the present invention is an antibody against human Claudin 5 protein, having an epitope that is a three-dimensional structure formed from the first extracellular loop and the second extracellular loop, preferable embodiments include antibodies whose affinity to human Claudin 5 protein mutants comprising the amino acid sequences represented by SEQ ID NOs: 93, 94, and/or 96 (1-1-5, 1-5-5, and/or 5-5-1: Example 5) is 1/5 or less, 1/20 or less, 1/100 or less, 1/500 or less, 1/2000 or less, or 1/10000 or less, of the affinity thereof to human Claudin 5 protein comprising the amino acid sequence represented by SEQ ID NO: 73.

When the antibody of the present invention is an antibody against human Claudin 5 protein, having an epitope that is a three-dimensional structure formed from the first extracellular loop and the second extracellular loop, preferable embodiments include antibodies having affinity to a human Claudin 5 protein mutant comprising the amino acid sequence represented by SEQ ID NO: 95 (5-1-5: Example 5).

The antibody of the present invention is preferably more specific to Claudin 5 protein. This makes it possible to further reduce side effects due to the opening of tight junctions other than the blood-brain barrier. From this viewpoint, preferable examples of the antibody of the present invention include an antibody whose affinity to Claudin family proteins other than Claudin 5 protein is 1/5 or less of the affinity thereof to Claudin 5 protein.

Examples of the "Claudin family proteins other than Claudin 5 protein" to be compared for affinity determination include Claudin 1, Claudin 2, Claudin 3, Claudin 4, Claudin 6, Claudin 7, Claudin 9, etc., in the case of humans; and Claudin 1, Claudin 2, Claudin 3, Claudin 4, etc., in the case of mice. When the affinity is determined, the Claudin family proteins to be compared may be used singly or in any combination of two or more; or all of them may be used.

The dissociation constant (Kd) of the antibody of the present invention is not limited. Kd is, for example, $1 \times 10^{-7}$ (M) or less, preferably $3 \times 10^{-8}$ (M) or less, and more preferably $1 \times 10^{-8}$ (M) or less.

Preferable examples of the antibody of the present invention include the following antibodies A to I, in terms of affinity to Claudin 5 protein, blood-brain barrier control activity, and the like.

(Antibody A)

Antibody A comprising:

a heavy-chain variable region comprising:

heavy-chain CDR1 comprising the amino acid sequence represented by SEQ ID NO: 1, heavy-chain CDR2 comprising the amino acid sequence represented by SEQ ID NO: 2, and heavy-chain CDR3 comprising the amino acid sequence represented by SEQ ID NO: 3; and/or a light-chain variable region comprising:

light-chain CDR1 comprising the amino acid sequence represented by SEQ ID NO: 5, light-chain CDR2 comprising the amino acid sequence represented by SEQ ID NO: 6, and light-chain CDR3 comprising the amino acid sequence represented by SEQ ID NO: 7.

In antibody A, preferable examples of the sequence of the entire heavy-chain variable region (sequence arranged in the order of FR1, CDR1, FR2, CDR2, FR3, CDR3, and FR4 from the N-terminal side) include the amino acid sequence represented by SEQ ID NO: 4; and preferable examples of the sequence of the entire light-chain variable region (sequence arranged in the order of FR1, CDR1, FR2, CDR2, FR3, CDR3, and FR4 from the N-terminal side) include the amino acid sequence represented by SEQ ID NO: 8. More specific examples of antibody A include antibody 2B12 in the Examples.

(Antibody B)
Antibody B comprising:
a heavy-chain variable region comprising:
heavy-chain CDR1 comprising the amino acid sequence represented by SEQ ID NO: 9,
heavy-chain CDR2 comprising the amino acid sequence represented by SEQ ID NO: 10, and
heavy-chain CDR3 comprising the amino acid sequence represented by SEQ ID NO: 11, and/or
a light-chain variable region comprising:
light-chain CDR1 comprising the amino acid sequence represented by SEQ ID NO: 13,
light-chain CDR2 comprising the amino acid sequence represented by SEQ ID NO: 14, and
light-chain CDR3 comprising the amino acid sequence represented by SEQ ID NO: 15.

In antibody B, preferable examples of the sequence of the entire heavy-chain variable region (sequence arranged in the order of FR1, CDR1, FR2, CDR2, FR3, CDR3, and FR4 from the N-terminal side) include the amino acid sequence represented by SEQ ID NO: 12; and preferable examples of the sequence of the entire light-chain variable region (sequence arranged in the order of FR1, CDR1, FR2, CDR2, FR3, CDR3, and FR4 from the N-terminal side) include the amino acid sequence represented by SEQ ID NO: 16. More specific examples of antibody B include antibody 2B1 in the Examples, (Antibody C)
Antibody C comprising:
a heavy-chain variable region comprising:
heavy-chain CDR1 comprising the amino acid sequence represented by SEQ ID NO: 17,
heavy-chain CDR2 comprising the amino acid sequence represented by SEQ ID NO: 18, and
heavy-chain CDR3 comprising the amino acid sequence represented by SEQ ID NO: 19; and/or
a light-chain variable region comprising:
light-chain CDR1 comprising the amino acid sequence represented by SEQ ID NO: 21,
light-chain CDR2 comprising the amino acid sequence represented by SEQ ID NO: 22, and
light-chain CDR3 comprising the amino acid sequence represented by SEQ ID NO: 23.

In antibody C, preferable examples of the sequence of the entire heavy-chain variable region (sequence arranged in the order of FR1, CDR1, FR2, CDR2, FR3, CDR3, and FR4 from the N-terminal side) include the amino acid sequence represented by SEQ ID NO: 20; and preferable examples of the sequence of the entire light-chain variable region (sequence arranged in the order of FR1, CDR1, FR2, CDR2, FR3, CDR3, and FR4 from the N-terminal side) include the amino acid sequence represented by SEQ ID NO: 24. More specific examples of antibody C include antibody 4F1 in the Examples.

(Antibody D)
Antibody D comprising:
a heavy-chain variable region comprising:
heavy-chain CDR1 comprising the amino acid sequence represented by SEQ ID NO: 25,
heavy-chain CDR2 comprising the amino acid sequence represented by SEQ ID NO: 26, and
heavy-chain CDR3 comprising the amino acid sequence represented by SEQ ID NO: 27; and/or
a light-chain variable region comprising:
light-chain CDR1 comprising the amino acid sequence represented by SEQ ID NO: 29,
light-chain CDR2 comprising the amino acid sequence represented by SEQ ID NO: 30, and
light-chain CDR3 comprising the amino acid sequence represented by SEQ ID NO: 31.

In antibody D, preferable examples of the sequence of the entire heavy-chain variable region (sequence arranged in the order of FR1, CDR1, FR2, CDR2, FR3, CDR3, and FR4 from the N-terminal side) include the amino acid sequence represented by SEQ ID NO: 28; and preferable examples of the sequence of the entire light-chain variable region (sequence arranged in the order of FR1, CDR1, FR2, CDR2, FR3, CDR3, and FR4 from the N-terminal side) include the amino acid sequence represented by SEQ ID NO: 32. More specific examples of antibody D include antibody 4D2 in the Examples.

(Antibody E)
Antibody E comprising:
a heavy-chain variable region comprising:
heavy-chain CDR1 comprising the amino acid sequence represented by SEQ ID NO: 33,
heavy-chain CDR2 comprising the amino acid sequence represented by SEQ ID NO: 34, and
heavy-chain CDR3 comprising the amino acid sequence represented by SEQ ID NO: 35; and/or
a light-chain variable region comprising:
light-chain CDR1 comprising the amino acid sequence represented by SEQ ID NO: 37,
light-chain CDR2 comprising the amino acid sequence represented by SEQ ID NO: 38, and
light-chain CDR3 comprising the amino acid sequence represented by SEQ ID NO: 39.

In antibody E, preferable examples of the sequence of the entire heavy-chain variable region (sequence arranged in the order of FR1, CDR1, FR2, CDR2, FR3, CDR3, and FR4 from the N-terminal side) include the amino acid sequence represented by SEQ ID NO: 36; and preferable examples of the sequence of the entire light-chain variable region (sequence arranged in the order of FR1, CDR1, FR2, CDR2, FR3, CDR3, and FR4 from the N-terminal side) include the amino acid sequence represented by SEQ ID NO: 40. More specific examples of antibody E include antibody 1B3 in the Examples.

(Antibody F)
Antibody F comprising:
a heavy-chain variable region comprising:
heavy-chain CDR1 comprising the amino acid sequence represented by SEQ ID NO: 41,
heavy-chain CDR2 comprising the amino acid sequence represented by SEQ ID NO: 42, and
heavy-chain CDR3 comprising the amino acid sequence represented by SEQ ID NO: 43; and/or
a light-chain variable region comprising:
light-chain CDR1 comprising the amino acid sequence represented by SEQ ID NO: 45,
light-chain CDR2 comprising the amino acid sequence represented by SEQ ID NO: 46, and
light-chain CDR3 comprising the amino acid sequence represented by SEQ ID NO: 47.

In antibody F, preferable examples of the sequence of the entire heavy-chain variable region (sequence arranged in the order of FR1, CDR1, FR2, CDR2, FR3, CDR3, and FR4 from the N-terminal side) include the amino acid sequence represented by SEQ ID NO: 44; and preferable examples of the sequence of the entire light-chain variable region (sequence arranged in the order of FR1, CDR1, FR2, CDR2, FR3, CDR3, and FR4 from the N-terminal side) include the amino acid sequence represented by SEQ ID NO: 48. More specific examples of antibody F include antibody 1D1 in the Examples.

(Antibody G)
Antibody G comprising:
a heavy-chain variable region comprising:
    heavy-chain CDR1 comprising the amino acid sequence represented by SEQ ID NO: 49,
    heavy-chain CDR2 comprising the amino acid sequence represented by SEQ ID NO: 50, and
    heavy-chain CDR3 comprising the amino acid sequence represented by SEQ ID NO: 51; and/or
a light-chain variable region comprising:
    light-chain CDR1 comprising the amino acid sequence represented by SEQ ID NO: 53,
    light-chain CDR2 comprising the amino acid sequence represented by SEQ ID NO: 54, and
    light-chain CDR3 comprising the amino acid sequence represented by SEQ ID NO: 55.

In antibody G, preferable examples of the sequence of the entire heavy-chain variable region (sequence arranged in the order of FR1, CDR1, FR2, CDR2, FR3, CDR3, and FR4 from the N-terminal side) include the amino acid sequence represented by SEQ ID NO: 52; and preferable examples of the sequence of the entire light-chain variable region (sequence arranged in the order of FR1, CDR1, FR2, CDR2, FR3, CDR3, and FR4 from the N-terminal side) include the amino acid sequence represented by SEQ ID NO: 56. More specific examples of antibody G include antibody 3A5 in the Examples.

(Antibody H)
Antibody H comprising:
a heavy-chain variable region comprising:
    heavy-chain CDR1 comprising the amino acid sequence represented by SEQ ID NO: 57,
    heavy-chain CDR2 comprising the amino acid sequence represented by SEQ ID NO: 58, and
    heavy-chain CDR3 comprising the amino acid sequence represented by SEQ ID NO: 59; and/or
a light-chain variable region comprising:
    light-chain CDR1 comprising the amino acid sequence represented by SEQ ID NO: 61,
    light-chain CDR2 comprising the amino acid sequence represented by SEQ ID NO: 62, and
    light-chain CDR3 comprising the amino acid sequence represented by SEQ ID NO: 63, In antibody H, preferable examples of the sequence of the entire heavy-chain variable region (sequence arranged in the order of FR1, CDR1, FR2, CDR2, FR3, CDR3, and FR4 from the N-terminal side) include the amino acid sequence represented by SEQ ID NO: 60; and preferable examples of the sequence of the entire light-chain variable region (sequence arranged in the order of FR1, CDR1, FR2, CDR2, FR3, CDR3, and FR4 from the N-terminal side) include the amino acid sequence represented by SEQ ID NO: 64. More specific examples of antibody H include antibody 2D1 in the Examples.

(Antibody I)
Antibody I comprising:
a heavy-chain variable region comprising:
    heavy-chain CDR1 comprising the amino acid sequence represented by SEQ ID NO: 65,
    heavy-chain CDR2 comprising the amino acid sequence represented by SEQ ID NO: 66, and
    heavy-chain CDR3 comprising the amino acid sequence represented by SEQ ID NO: 67; and/or
a light-chain variable region comprising:
    light-chain CDR1 comprising the amino acid sequence represented by SEQ ID NO: 69,
    light-chain CDR2 comprising the amino acid sequence represented by SEQ ID NO: 70, and
    light-chain CDR3 comprising the amino acid sequence represented by SEQ ID NO: 71.

In antibody I, preferable examples of the sequence of the entire heavy-chain variable region (sequence arranged in the order of FR1, CDR1, FR2, CDR2, FR3, CDR3, and FR4 from the N-terminal side) include the amino acid sequence represented by SEQ ID NO: 68; and preferable examples of the sequence of the entire light-chain variable region (sequence arranged in the order of FR1, CDR1, FR2, CDR2, FR3, CDR3, and FR4 from the N-terminal side) includes the amino acid sequence represented by SEQ ID NO: 72. More specific examples of antibody I include antibody 4A1 in the Examples.

In the above preferable examples of the sequences of the entire heavy-chain variable region and the sequences of the entire light-chain variable region of antibodies A to I (SEQ ID NOs: 4, 8, 12, 16, 20, 24, 28, 32, 36, 40, 44, 48, 52, 56, 60, 64, 68, and 72), the amino acid sequences may be mutated. For example, sequences preferably having 90% or more, more preferably 95% or more, even more preferably 98% or more, and still more preferably 99% or more, identity to the above preferable examples (SEQ ID NOs: 4, 8, 12, 16, 20, 24, 28, 32, 36, 40, 44, 48, 52, 56, 60, 64, 68, and 72) can also be employed as the sequences of the entire heavy-chain variable region and the sequences of the entire light-chain variable region of antibodies A to I. The mutation site may be any site, but is preferably a site other than CDR.

The antibody of the present invention may be either a monoclonal antibody or a polyclonal antibody, but is preferably a monoclonal antibody in terms of Kd values, specificity, and the like.

The molecular weight of the antibody of the present invention is not limited. The lower limit is, for example, 20,000, preferably 50,000, more preferably 100,000, and even more preferably 120,000. The upper limit is, for example, 1,000,000, preferably 500,000, and more preferably 200,000, The structure of the antibody of the present invention is not limited. The antibody of the present invention may contain a constant region or may not contain a constant region. When a constant region is contained, all of the heavy-chain constant regions (CH1, CH2, and CH3) and the light-chain constant region (CL) may be contained; or any one, or a combination of two or more, of them may be contained.

Specific examples of the structure of the antibody of the present invention include immunoglobulins, Fab, F(ab')$_2$, minibodies, scFv-Fc, Fv, scFv, diabodies, triabodies, tetrabodies, and the like. Among these, immunoglobulins are preferable in terms of the effects of the present invention.

Immunoglobulins are configured to have a combination of two structures each comprising one heavy chain having a heavy-chain variable region and a heavy-chain constant region, and one light chain having a light-chain variable region and a light-chain constant region.

Fab contains a heavy-chain fragment containing the heavy-chain variable region and CH1 in the heavy-chain constant region, and a light chain containing the light-chain variable region and the light-chain constant region (CL), wherein the heavy-chain variable region and the light-chain variable region are associated by the non-covalent intermolecular interactions described above, or are joined by a disulfide bond. In the Fab, CH1 and CL may be disulfide-bonded between thiol groups of cysteine residues present in each of CH1 and CL.

F(ab')$_2$ has two pairs of the above-mentioned Fabs, and each CH1 has a disulfide bond between thiol groups of cysteine residues contained in these Fabs.

Minibodies are configured such that two fragments each containing CH3 bonded to the heavy-chain variable region constituting scFV, described below, are associated by non-covalent intermolecular interactions between their CH3.

ScFv-Fc is configured such that two antibody fragments each containing scFv described below, CH2, and CH3 are associated by non-covalent intermolecular interactions between their CH3, as with the above minibodies, and are joined by a disulfide bond between thiol groups of cysteine residues contained in each CH3.

Fv, also called the minimum structural unit of an antibody, is configured such that the heavy-chain variable region and the light-chain variable region are associated by non-covalent intermolecular interactions. In the Fv, thiol groups of cysteine residues present in the heavy-chain variable region and the light-chain variable region may be disulfide-bonded.

scFv is configured such that the C-terminal of the heavy-chain variable region and the N-terminal of the light-chain variable region are linked by a linker, or configured such that the N-terminal of the heavy-chain variable region and the C-terminal of the light-chain variable region are linked by a linker. scFv is also called a single-chain antibody.

Diabodies, triabodies, and tetrabodies are configured such that the above scFv forms dimers, trimers, and tetramers, respectively, which are associated in a structurally stable state by non-covalent intermolecular interactions between the variable regions, as with Fv etc.

When the antibody of the present invention is an immunoglobulin, its class is not limited. Examples of the class include IgA, IgD, IgE, IgG, IgM, etc., and further include subclasses thereof. Preferable examples of the class include IgG, IgM, etc.; more preferably IgG; even more preferably IgG2; and still more preferably IgG2a.

The origin of the antibody of the present invention is not limited. Examples of the antibody of the present invention include human-derived antibodies, mouse-derived antibodies, rat-derived antibodies, rabbit-derived antibodies, monkey-derived antibodies, chimpanzee-derived antibodies, and the like. The antibody of the present invention may be a chimeric antibody (e.g., an antibody obtained by replacing the amino acid sequence of the constant region of an antibody derived from an organism other than a human (e.g., a mouse) with the amino acid sequence of the constant region of a human-derived antibody), a humanized antibody, a fully humanized antibody, or the like.

The antibody of the present invention can be produced, for example, by or according to a standard method, except that a proteoliposome containing and exposing the extracellular domain of the following Claudin 5 protein is used as an immunogen (production method 1). Specifically, when the antibody of the present invention is a polyclonal antibody, this antibody can be obtained in such a manner that a non-human animal (e.g., a rabbit) is immunized with a proteoliposome, and the antibody is obtained from the serum of the immunized animal according to a standard method. In contrast, when the antibody of the present invention is a monoclonal antibody, this antibody can be obtained in such a manner that a non-human animal (e.g., a mouse) is immunized with a proteoliposome, and the antibody is obtained from hybridoma cells prepared by cell-fusion of the obtained spleen cells and myeloma cells (Current Protocols in Molecular Biology, edit, Ausubel et al, (1987) Publish. John Wiley and Sons. Sections 11.4 to 11.11).

In general, the antibody of the present invention cannot be obtained even by simply using a proteoliposome containing wild-type Claudin 5 protein as an immunogen.

In order to obtain the antibody of the present invention, it is preferable to use, as an immunogen, a proteoliposome containing, for example, Claudin 5 protein in which the amino acid sequence of the extracellular domain is the extracellular domain sequence of Claudin 5 protein of the target biological species (e.g., human), and the amino acid sequence of the intracellular domain is the intracellular domain sequence of Claudin 5 protein of the animal to be immunized, wherein the extracellular domain is exposed (immunogen 1). Examples of immunogen 1 include a proteoliposome containing human-Mouse chimeric Claudin 5 protein comprising the amino acid sequence represented by SEQ ID NO: 75.

Alternatively, it is preferable to use a proteoliposome (immunogen 2) in which the extracellular domain of Claudin 5 protein is exposed to both sides of the membrane (preferably, the other domains are not exposed) as an immunogen for obtaining the antibody of the present invention. Examples of immunogen 2 include a proteoliposome containing extracellular domain reversible Claudin 5 protein comprising the amino acid sequence represented by SEQ ID NO: 77.

As the immunogen, the above immunogens 1 and 2 may be used singly or in combination of two or more.

Proteoliposomes used as immunogens can be prepared by a known cell-free protein synthetic system using, for example, polynucleotides encoding Claudin 5 protein mutants (human-mouse chimeric Claudin 5 protein and extracellular domain reversible Claudin 5 protein mentioned above). When the genomic sequence encoding Claudin 5 protein is directly used as the coding sequence of the above mutant, protein expression usually rarely occurs. The reason for this is considered to be that since the genomic sequence encoding Claudin 5 protein has a very high GC content, mRNA has a high-order structure to inhibit translation. Therefore, when a genomic sequence encoding Claudin 5 protein is used as the coding sequence of the above mutant, it is desirable to use the genomic sequence after the codons are converted so that the GC content is about 50% (e.g., 45 to 55%).

As lipids constituting proteoliposomes, various known lipids capable of constituting liposomes can be used. Among lipids, a combination of phosphatidylcholine (preferably egg yolk-derived phosphatidylcholine) and monophosphoryl lipid A is preferably used. The weight ratio of both (phosphatidylcholine:monophosphoryl lipid A) in this combination is, for example, 5 to 200:1, preferably 10 to 100:1, more preferably 20 to 70:1, even more preferably 30 to 50:1, and still more preferably 35 to 45:1.

The subject animals to be immunized with proteoliposomes are not limited, as long as they are animals capable of producing antibodies. Preferable examples of the subject animals include autoimmune disease animals (e.g., BXSB mice in the case of mice).

When at least the amino acid sequences of the CDRs of the antibody of the present invention are already known, the antibody of the present invention can also be produced by a method comprising culturing a host transformed with a polynucleotide encoding the antibody of the invention, and recovering a fraction containing the antibody of the invention (production method 2).

The polynucleotide encoding the antibody of the present invention is not limited, as long as it contains the antibody of the present invention in an expressible state. The polynucleotide may contain other sequences in addition to the coding sequence of the antibody of the present invention. Other sequences include a secretory signal peptide coding sequence to be arranged adjacent to the coding sequence of the antibody of the present invention, a promoter sequence, an enhancer sequence, a repressor sequence, an insulator sequence, a duplicate origin, a drug resistance gene coding sequence, and the like. Moreover, the polynucleotide encoding the antibody of the present invention may also be a linear polynucleotide or a circular polynucleotide (e.g., a vector).

Specific examples of the polynucleotide of the present invention include (I) a polynucleotide comprising a base sequence encoding at least one member selected from the group consisting of the heavy chain, heavy-chain variable region, and heavy-chain CDRs 1 to 3 of the antibody of the present invention, (II) a polynucleotide comprising a base sequence encoding at least one member selected from the group consisting of the light chain, light-chain variable region, and light-chain CDRs 1 to 3 of the antibody of the present invention, (III) a nucleic acid comprising a base sequence encoding at least one member selected from the group consisting of the heavy chain, heavy-chain variable region, and heavy-chain CDRs 1 to 3 of the antibody of the present invention, and a polynucleotide comprising a base sequence encoding at least one member selected from the group consisting of the light chain, light-chain variable region, and light-chain CDRs 1 to 3 of the antibody of the present invention.

The hosts are not limited, and examples include insect cells, eukaryotic cells, mammalian cells, and the like. Among these, HEK cells, CHO cells, NS0 cells, SP2/O cells, etc., which are mammalian cells, are preferable, in terms of more efficient expression of antibodies.

The methods for transformation, culture, and recovery are not limited, and known methods in antibody production can be used After recovery, the antibody of the present invention may be purified, if necessary. Purification can be performed by known methods in antibody production, such as chromatography and dialysis.

3. Complex

As one embodiment, the present invention relates to a complex of the antibody of the present invention and a drug (also referred to as "the complex of the present invention" in the present specification). This will be described below.

The drug is not limited, and can be suitably selected depending on the purpose. Examples of the drug include bioactive substances, such as nucleic acids, polynucleotides, genes, and analogs thereof, glycosaminoglycan and derivatives thereof, oligosaccharide, polysaccharides and derivatives thereof, proteins, and peptides; pharmacologically active substances, such as anti-nerve agents, antiviral agents, anticancer agents, antibiotics, enzyme agents, antioxidants, anti-inflammatory agents, steroid drugs, angiotensin-converting enzyme inhibitors, vasodilators, smooth muscle cell growth and/or migration inhibitors, platelet aggregation inhibitors, anticoagulants, chemical mediator release inhibitors, immunosuppressants, lipid uptake inhibitors, hormonal agents, angiotensin receptor antagonists, vascular endothelial cell stimulators or inhibitors, aldose reductase inhibitors, lipoxygenase inhibitors, immunostimulators, Maillard reaction inhibitors, amyloidosis inhibitors, nitric oxide synthase (NOS) inhibitors, advanced glycation end product (AGE) inhibitors, and radical scavengers; and the like. The complex of the present invention comprises the antibody of the present invention as a partial structure, whereby the complex can more efficiently penetrate the blood-brain barrier. Therefore, among the drugs, anti-nerve agents (e.g., drugs that can be used for the treatment and/or diagnosis of the central nervous system) are preferable.

Specific examples of anti-nerve agents include anxiolytic agents, such as Constan, Sepazon, Cersine, Serenal, Solanax, Depas, Balance, Meilax, Rize, Rivotril, Lexotan, Wypax, Sediel, Grandaxin, and Erispan; antidepressants, such as Anafranil, Tofranil, Tryptanol, Amoxan, Amplit, Prothiaden, Tecipul, Tetramide, Ludiomil, Desyrel, Reslin, Abilit, Dogmatyl, Miradol, Ritalin, Depromel, Paxil, Luvox, and Toledomin; sleeping drugs, such as Amoban, Halcion, Evamyl, Myslee, Rhythmy, Lendormin, Loramet, Silece, Doral, Benzarin, Eurodin, Rohypnol, Insumin, Somelin, Dalmate, Phenobal, and Isomytal; tranquilizers, such as Wintermin, Contomin, Neuleptil, Hirnamin, PZC, Melleril, Impromen, Serenace, Orap, Cremin, Clofekton, Defekton, Forit, Lodopin, and Atarax; mood stabilizers, such as Limas and Tegretol; antiepileptic agents, such as Ethotoin, Phenyloin, Acetylpheneturide, Primidone, Sultiame, Ethosuximide, Clonazepam, Carbamazepine, sodium valproate, and Zonisamide; Parkinson's disease therapeutic agents, such as levodopa agents, pergolide mesilate, amantadine hydrochloride, trihexyphenidyl hydrochloride, piroheptine hydrochloride, mazaticol hydrochloride, metixene hydrochloride, biperiden, profenamine, and droxidopa; and the like.

The complex of the present invention is formed in such a manner that the antibody of the present invention and a drug are bonded together directly or indirectly through a linker. The bonding form is not limited, and examples include covalent bonding, coordinate bonding, ionic bonding, and the like. Bonding between the antibody of the present invention and a drug can be formed by or according to a known method, depending on the bonding form.

Covalent bonding can be formed, for example, by the reaction of the antibody of the present invention with the functional group of each drug or an optionally introduced functional group. Examples of the combination of functional groups include an amino group and a carboxyl group, a carboxyl group and a hydroxyl group, a maleimide group and a thiol group, a thiol group and a thiol group, a hydrazide group and a ketone group, a hydrazide group and an aldehyde group, an amino group and an aldehyde group, a thiol group and a carboxyl group, an amino group and a squaric acid derivative, a dienyl aldehyde group and an amino group, a halo ester and a thiol group, an azide and an alkyne, and the like.

4. Medicine

As one embodiment, the present invention relates to a medicine comprising at least one member selected from the group consisting of the antibody of the present invention and the complex of the present invention (also referred to as "the medicine of the present invention" in the present specification).

The antibody of the present invention can open junctions between cerebrovascular endothelial cells to promote substance permeation through the blood-brain barrier. Accordingly, the antibody of the present invention and the complex of the present invention can be suitably used as active ingredients of medicines particularly for use in blood-brain barrier control (suppression), cerebrovascular endothelial cell layer barrier function control (suppression), promotion of drug permeation through the blood-brain barrier, etc.

When the medicine of the present invention comprises the antibody of the present invention but does not comprise the complex of the present invention, the combined use of the medicine with a drug can promote the permeation of the drug through the blood-brain barrier. Moreover, when the medicine of the present invention comprises the complex of the present invention, the use of the medicine alone or in combination with a drug can promote the permeation of the drug in the complex or the combined drug through the blood-brain barrier.

The content of the active ingredient in the medicine of the present invention can be suitably set in consideration of the type of target disease, desired therapeutic effects, administration method, treatment period, patient's age, patient's body weight, etc. For example, the content of the active ingredient in the medicine of the present invention can be set to about 0.0001 parts by weight to 100 parts by weight based on 100 parts by weight of the entire medicine of the present invention.

The dosage form of the medicine of the present invention is not limited, as long as the desired effects are obtained. The medicine of the present invention can be administered to mammals, including humans, by any of the following administration routes: oral administration and parenteral administration (e.g., intravenous injection, intramuscular injection, subcutaneous administration, rectal administration, dermal administration, and local administration). The administration form is preferably parenteral administration, and more preferably intravenous injection. The dosage forms for oral administration and parenteral administration, and their production methods are well known to a person skilled in the art. The medicine of the present invention can be produced according to a standard method by mixing the active ingredient with a pharmaceutically acceptable carrier etc.

Examples of dosage forms for parenteral administration include injection preparations (e.g., intravenous drip infusion, intravenous injection, intramuscular injection, subcutaneous injection, and endodermic injection), external preparations (e.g., ointments, cataplasms, and lotions), suppositories, inhalants, eye drops, ophthalmic ointments, nasal drops, ear drops, liposome agents, and the like. For example, an injection preparation can be prepared by dissolving an antibody or cells in distilled water for injection, and optionally adding a solubilizer, a buffer, a pH adjuster, an isotonizing agent, a soothing agent, a preservative, a stabilizer, etc. The medicine can also be used as a freeze-dried preparation prepared before use.

The medicine of the present invention may further comprise other drugs effective for the treatment or prevention of diseases. The medicine of the present invention can also contain components, such as sterilants, antiphlogistics, cell activators, vitamins, and amino acids, if necessary.

The carrier used for formulating the medicine of the present invention may contain excipients, binders, disintegrators, lubricants, coloring agents, and flavoring agents that are generally used in this technical field, and may optionally contain stabilizers, emulsifiers, absorption enhancers, surfactants, pH adjusters, antiseptics, antioxidants, extenders, moisturizers, surface activators, dispersants, buffers, preservatives, solubilizers, soothing agents, and the like.

The dose of the medicine of the present invention can be determined by clinical doctors based on various factors, such as the administration route, the type of disease, the degree of symptom, the age, sex, and body weight of the patient, the severity of disease, pharmacological findings, such as drug kinetics and toxicological characteristics, whether a drug delivery system is used, and whether the medicine is administered as part of combination with other drugs. The dose of the medicine of the present invention can be set to, for example, about 1 μg/kg (body weight) to 10 g/kg (body weight) per day. The administration schedule of the medicine of the present invention can also be determined in consideration of the same factors as the dose thereof. For example, the medicine of the present invention can be administered in the above dose per day once a day to once a month.

5. Reagent

As one embodiment, the present invention relates to a reagent comprising at least one member selected from the group consisting of the antibody of the present invention and the complex of the present invention (also referred to as "the reagent of the present invention" in the present specification). More specifically, the present invention relates to a reagent, for example, for detecting Claudin 5. The term "reagent" mentioned herein includes "diagnostic drugs" for performing examination, detection, diagnosis, etc., by, for example, detecting Claudin 5.

The reagent of the present invention may be in the form of a composition comprising at least one member selected from the group consisting of the antibody of the present invention and the complex of the present invention. The composition may contain other components, if necessary. Examples of other components include bases, carriers, solvents, dispersants, emulsifiers, buffers, stabilizers, excipients, binders, disintegrators, lubricants, thickeners, moisturizers, coloring agents, flavoring agents, chelating agents, and the like.

The reagent of the present invention may be in the form of a kit comprising at least one member selected from the group consisting of the antibody of the present invention and the complex of the present invention. The kit may comprise instruments, reagents, etc., used for implementation of detection, separation, etc., of Claudin 5. Examples of such instruments and reagents include test tubes, microtiter plates, agarose particles, latex particles, purification columns, labelled antibodies, standard samples (positive control, negative control), and the like.

EXAMPLES

The following describes the present invention in detail with reference to the Examples. However, the invention is not limited to these examples.

Reference Example 1: Production of Antigens

Immunogens (proteoliposomes) for use in the production of antibodies were prepared as follows.

Reference Example 1-1: Preparation of Template Plasmids

A DNA fragment that encodes a DNA fragment consisting of the coding sequence (SEQ ID NO: 74) of wild-type human Claudin 5 protein (SEQ ID NO: 73), a DNA fragment consisting of the coding sequence (SEQ ID NO: 76) of human-mouse-chimeric Claudin 5 protein (SEQ ID NO: 75), or a DNA fragment consisting of the coding sequence (SEQ ID NO: 78) of extracellular domain reversible Claudin 5 protein (SEQ ID NO: 77) was inserted into a pEU-E01 vector (CellFree Sciences) using the Gateway or Gibson Assembly method to obtain template plasmids.

In a preliminary experiment, when a base sequence derived from human cDNA was used as a base sequence for a coding DNA fragment of wild-type human Claudin 5 protein, the synthesis of protein was not confirmed. This is probably because a Claudin 5-coding sequence derived from human cDNA has a high average GC-content of 68%; and the GC-content in some regions is even as high as 80%, suggesting that mRNA has a high-order structure, and inhibits the translation process. Thus, a sequence was prepared by converting codons of a base sequence derived from human cDNA such that the amino acid sequence did not change, and adjusting the GC-content to about 50%. This prepared sequence was used as a coding sequence of wild-type human Claudin 5 protein (SEQ ID NO: 74). FIG. 1 illustrates a comparison between the coding sequence of Claudin 5 protein from human cDNA, and the codon-converted coding sequence of Claudin 5 protein (SEQ ID NO: 74).

Human-mouse-chimeric Claudin 5 protein consists of an amino acid sequence of which the extracellular regions and their neighboring transmembrane regions are derived from a human, and the intracellular regions and their neighboring transmembrane regions are derived from a mouse, with its C-terminal site deleted. FIG. 2 illustrates the sequence of this protein. The coding sequence of this protein is also codon-converted, as with the coding sequence of Claudin 5 protein derived from human cDNA.

The extracellular domain reversible Claudin 5 protein is a Claudin 5 protein that has been modified such that the extracellular domains are arranged on both sides of the lipid membrane. FIG. 3 illustrates the sequence of the protein and a schematic view of its arrangement in the lipid membrane. The coding sequence of this protein is also codon-converted, as with the coding sequence of Claudin 5 protein derived from human cDNA.

Reference Example 1-2: Preparation of Liposome

The liposome added to a cell-free system was prepared using a lipid mixture prepared by adding MPLA (Avanti) to egg yolk-derived phosphatidylcholine (eggPC, Wako Pure Chemical Industries, Ltd.). Specifically, a liposome was prepared as described below.

A solution of 50 mg of phosphatidylcholine and 1.25 mg of MPLA in chloroform was dispensed into an eggplant flask, and mixed. Chloroform was evaporated by rotating the flask with an evaporator, thereby obtaining a thin lipid film. To completely remove chloroform from the lipid film, the flask was allowed to stand in a vacuum desiccator under negative pressure for at least 6 hours. A buffer (SUB-AMIX SGC buffer), which came with a protein synthesis kit (WEPRO7240 expression kit, CellFree Science), was added to the flask to give a lipid concentration of 25 mg/mL; and sonicated (Branson, SONIFIER model 450D-Advanced), thereby preparing a liposome.

Reference Example 1-3: Preparation of Proteoliposome Using Cell-Free Protein Synthesis System A proteoliposome was prepared using a protein synthesis kit (WEPRO7240 expression kit, CellFree Science). Specifically, a proteoliposome was prepared as described below.

A transcription reaction was performed in accordance with the procedure of the kit using the template plasmids prepared in Reference Example 1-1.

The translation reaction was performed by the dialysis double-layer method. The specific procedure is as follows. 3.5 mL of a SUB-AMIX SGC buffer, which came with the kit, was added to a 6-well, flat-bottomed plate (TPP). Dialysis cups (Pierce, Slide-A-Lyzer™ MINI Dialysis Device, 10 kDa MWCO) were inserted into the plate, and 2 mL of the SUB-AMIX SGC buffer was injected into the cups. 125 μL of mRNA obtained by the transcription reaction above, 125 μL of a wheat germ extract, that came with the kit, 2 μL of creatine kinase, and 200 μL of the liposome obtained in Reference Example 1-2 were mixed to prepare a translation reaction solution; and the translation reaction solution was gently injected under the layer of the SUB-AMIX SGC buffer in the cups, and layered. The solution was left to stand at 15° C. for 24 hours to allow a translation reaction to proceed.

After the translation reaction, the solutions inside each dialysis cup were mixed and collected with a 15-mL or 50-mL centrifuge tube. The proteoliposome was precipitated by subjecting the tubes to centrifugation (15,000 rpm, 10 min, 4° C.). The supernatant was removed, and the pellets were suspended again in a PBS or BBS buffer that, was filter-sterilized. Centrifugation and suspension with a buffer were repeated three times to wash the proteoliposome. Finally, the proteoliposome was suspended in a predetermined amount of a buffer to obtain a proteoliposome suspension. The concentration of each protein in the proteoliposome suspension was calculated by comparing the bands detected by SDS-PAGE and CBB staining, with those of BSA concentration standards.

Example 1: Production of Antibody

Monoclonal antibodies were prepared using the immunogens obtained in Reference Example 1 (the proteoliposome of human-mouse-chimeric Claudin 5 protein, and the proteoliposome of extracellular domain reversible Claudin 5 protein), Specifically, monoclonal antibodies were prepared as described below.

Example 1-1: Immunization

Each proteoliposome obtained in Reference Example 1 was diluted to give a protein concentration of 40 μg/mL, 500 μL of the diluted solution was intraperitoneally administered to BXSB mice (male, 6 weeks old) (Shimizu Laboratory Supplies Co., Ltd.). Thereafter, administration was performed every 2 weeks, 2 to 3 times in total.

Example 1-2: Cell Fusion (1) Animal, Cells: immunized BXSB mice, their splenocytes, and mouse myeloma cells (P3U1 cells) were used.
(2) Reagents: PEG1500 and 10× BM Condimed H1 were purchased from Roche Diagnostics, 50×HAT supplement was purchased from Invitrogen. Other reagents for use were of special grade. The other reagents for use were of special grade.
(3) Hemolyzing Agent: 2.06 g of Tris was dissolved in 100 mL of ultrapure water, and adjusted to a pH of 7.65 with 1N HCl. This solution and a solution of 8.3 g of $NH_4Cl$ in 900 mL of ultrapure water were combined (1000 mL in total, pH=7.2), The obtained solution was then sterilized in an autoclave, and stored at 4° C.

(4) Experiment Operation (4-1) Preparation of Spleen Suspension: after 3 days from the final immunization, the spleen was removed by laparotomy under isoflurane anesthesia, and transferred to a dish containing a cold RPMI medium (serum-free). After the spleen was minced, the splenocytes were suspended in a cold RPMI medium using a cell strainer (100 μm, Becton Dickinson). An RPMI medium was added to the splenocyte suspension, and the cells were washed by centrifugation (300 g, 5 min) using a cooled centrifuge, Subsequently, 5 mL of the hemolyzing agent was added to the cell pellets, and the result was incubated on ice for 5 minutes. 30 mL of an RPMI medium was added thereto, followed by washing by centrifugation. Finally, a tissue fragment was completely removed from the splenocyte suspension using a cell strainer (70 μm).

(4-2) Preparation of P3U1 Cells: P3U1 cells prepared by sub-culture in 50 mL of a 10% FBS-containing RPMI medium were transferred to a Falcon tube. The cells were washed by centrifugation (300 g, 5 min) three times (washing solution: an RPMI medium), thereby obtaining pellets of P3U1 cells.

(4-3) Cell Fusion: the P3U1 cell pellets prepared in section (4-2) were crushed with the spleen suspension prepared in section (4-1), and well suspended (cell ratio: splenocytes: P3U1=10:1); followed by centrifugation (300 g, 5 min), thereby obtaining cell pellets. The pellets were loosened by tapping the bottom of the Falcon tube, for example, with the palm. Two mL of PEG1500 kept at 37° C. was then slowly added to the cells over 1 minute, while rotating the Falcon tube with gentle stirring using the end of the tip. Thereafter, the Falcon tube was sufficiently tapped for 30 seconds, and allowed to stand for 30 seconds. Subsequently, 5 mL of an RPMI medium was added to the centrifuge tube over 2 minutes in the same manner that PEG1500 was added, and the tube was allowed to stand for 3 minutes at 37° C. Then, 30 mL of an RPMI medium was added to the tube, followed by centrifugation (300 g, 5 min). The supernatant was discarded, and the cells were suspended in an RPMI medium containing 1×HAT/20% FBS/10% BM Condimed H1. The resulting suspension (total volume: 50 mL) was seeded, 0.5 mL each, in each well of four sets of 24-well plates that were supplemented with 0.5 mL of the RPMI medium containing 1×HAT/20% FBS/10% BM Condimed H1 beforehand. The cells were continuously cultured for a minimum of 7 days in an incubator, while the selection status was observed over time.

Example 1-3: Preparation of Screening Cells

A DNA fragment consisting of the coding sequence of wild-type human Claudin 5 protein was inserted into a pCX4pur vector (Osaka Bioscience Institute) to obtain a vector for preparing a retrovirus. Packaging cells (Phoenix A cells) were seeded into each well of a 12-well plate (Becton Dickinson), 0.5×10$^5$ cells each, and cultured for 24 hours. Thereafter, phoenix A cells were transfected with 0.5 μg of a pCL-Ampho Vector, and 0.5 μg of the vector for preparing a retrovirus using 3 μL of X-tremeGENE HP DNA (Roche Diagnosis). After 24 hours, the medium was replaced, and culture was continued for another 24 hours. The culture supernatant containing retroviruses was collected and filtered through a 0.45-μm filter to remove contaminants, followed by addition of polybrene (Sigma Aldrich) to give a concentration of 8 μg/mL. Human fibrosarcoma-derived cells (HT-1080) were then cultured using the obtained solution for 24 hours. Thereafter, the cells were cultured in a 10-cm dish (Corning Incorporated) with DMEM that was supplemented with 10% FBS containing 5 μg/mL puromycin for 2 days to remove uninfected cells.

Example 1-4: Screening Using FACS and Cloning

Screening cells obtained in Example 1-3 or mock cells (retrovirus-infected HT-1080 cells that do not express Claudin) were seeded into 10-cm dishes, and the cells were harvested the following day. 100 μL of the culture supernatant intended for screening obtained in Example 1-2 was added as the primary antibody to the obtained cells (1.0×10$^5$ cells), and allowed to react at 4° C. for 1 hour. The cells were washed three times with 0.2% BSA-TBS, and then mixed with 100 μL of a secondary antibody solution (FITC conjugated goat anti-mouse IgG+IgM in 1% BSA-PBS (1:400)), followed by a reaction at 4° C. for 1 hour. The cells were washed with 0.2% BSA-TBS, and FACS analysis (FACS caliber, BD Bioscience) was performed. In the histograms with the fluorescent signal on the horizontal axis and the cell count on the vertical axis, when peaks shifted to the right side (the side on which fluorescence signals were stronger), as compared with the mock cells, positive clones (anti-Claudin 5 antibody-producing cells) were determined to be present in the wells containing the culture supernatant used for the treatment.

Cloning was performed using a 96-well plate into which a spleen suspension was seeded in each well in 100-μL portions beforehand to form a support layer. The cells in the wells in which positive clones were present were diluted with a 10% FBS-containing RPMI medium, 100-fold for the first cloning; and then diluted in three steps of 1000-fold, 6000-fold, and 36000-fold for the second cloning and the following cloning. 100 μL of the diluted cells was seeded into each well of the 96-well plate in which a support layer was formed, and cultured in an incubator. Cloning was determined to have ended with an inverted phase-contrast microscope by confirming that positive clones selected by FACS were a single clone.

As a result, three hybridomas (4F1, 4A1, and 1B3) were obtained when the proteoliposome of the human-mouse-chimeric Claudin 5 protein was used as the immunogen. Five hybridomas (1D1, 2B1, 3A5, 2D1, and 2B12) were obtained when the proteoliposome of the extracellular domain reversible Claudin 5 protein was used as the immunogen. Additionally, one hybridoma (4D2) was obtained when the two types of proteoliposomes were mixed and used as the immunogen.

Example 1-5: Expanding Culture Scale of Cloned Hybridomas

The cloned hybridomas were transferred to a 24-well plate in which a support layer of ddY mouse splenocytes was formed beforehand, and the hybridomas were cultured in an incubator. After the cells began to grow, the entire culture fluid was transferred to a 25-cm$^3$ flask for tissue culture that contained 9 mL of a RPMI medium supplemented with 10% FBS, and culture was continued. After further growth was confirmed, the entire culture fluid was transferred to a 75-cm$^3$ flask for tissue culture that contained 40 mL of a RPMI medium supplemented with 10% FBS, and culture was continued.

Example 1-6: Preparation of Antibodies (1) Animal: BALB/c nu/nu mice were used.
(2) Cells for Use: cloned hybridoma cells (3) Reagents for Use: pristane (2,6,10,14-tetramethyl pentadecane) was purchased from Wako Pure Chemical Industries, Ltd., and Protein G Sepharose 4 Fast Flow was purchased from GE Healthcare.
(4) Ascites Recovery: 0.5 mL of pristine was administered to BALB/c nu/nu mice through their peritoneal cavity. One week later, hybridoma cells ($1 \times 10^7$ cells) were intraperitoneally injected. Because mice treated with hybridomas rapidly accumulated ascites from 7 to 10 days after administration, ascites was collected under anesthesia at the time the mice exhibited maximum swelling in the abdomen. The ascites was collected in a 15-mL Falcon tube, and centrifuged (3000 rpm, 10 minutes) to remove unwanted matter. The ascites was stored at −80° C., and thawed before use.
(5) Purification by Protein G
(5-1) Preparation of Reagent:
  Starting Buffer: a 20 mM sodium phosphate buffer, pH 7.0; 20 mM disodium phosphate (5.36 g/L) and 20 mM sodium dihydrogen phosphate (2.76 g/L) were mixed in a ratio of 61:39.
  Elution Buffer: 100 mM glycine HCl, pH 2.7; 7.507 g of glycine was dissolved in 950 mL of Milli-Q water, and adjusted to a pH of 2.7 with HCl, followed by increasing the total volume to 1000 mL.
  Neutralize Buffer: 1.0M tris HCl, pH 9,0; hydrochloric acid was added to 50 mL of 2.0M tris(hydroxymethyl)aminomethane (242 g/L) to adjust the pH to 9.0, and the mixture was increased with Milli-Q water to a total of 100 mL.
  Elution (non-specifically bound protein) Buffer: 3M NaCl, 17.5 g of sodium chloride was dissolved in 100 mL of Milli-Q water.
(5-2) Purification:
A three-fold volume of the starting buffer was added to the ascites fluid, and the mixture was left to stand for 20 minutes; followed by centrifugation (3000 rpm, 30 minutes) and filtration through a 0.8-µm membrane filter, thereby removing insoluble matter. The resulting sample was loaded onto a protein G column (0.7×5 cm) that was well equilibrated with the starting buffer. After complete run-off of the sample, the column was washed with 30 mL of the starting buffer. 10 mL of the elution buffer was passed through the column to elute an antibody. The eluate was separated into 50 drops using a fraction collector. Before this step, 50 µL of a neutralize buffer was added to each fraction in the fraction collector beforehand. The resulting antibody fractions were dialyzed (Slide-A-Lyzer 20K MWCO) in PBS at 4° C. The name of the purified monoclonal antibody is the same as that of the corresponding hybridoma (e.g., the antibody obtained from hybridoma 2B12 is referred to as "antibody 2B12," or simply "2B12").

Example 2: Determination of Class, Amino Acid Sequence, and Kd Values of Antibodies Example 2-1: Determination of Class of Antibodies (1) Cells for Use: hybridomas cloned in Example 1.
(2) Reagents for Use: a mouse monoclonal antibody isotyping test kit was purchased from AbD Serotec. Other reagents for use were of special grade.
(3) Experimental Methods: the supernatant of a hybridoma culture was diluted about 10-fold with 1% BSA(w/v)-PBS, and 150 µL of the diluted solution was added to a development tube. After being allowed to stand for 30 seconds, the development tube was lightly vortexed to completely suspend colored microparticles in the tube. An isotyping strip was then added to the development tube, and the tube was allowed to stand for 5 to 10 minutes. The class of the antibodies was determined by locating the bands. Table X illustrates the class of each antibody.

TABLE X

|   | Antibody | Class |
|---|----------|-------|
| 1 | 4F1  | IgM   |
| 2 | 4A1  | IgG2b |
| 3 | 1B3  | IgG2  |
| 4 | 4D2  | IgM   |
| 5 | 1D1  | IgG2a |
| 6 | 2B1  | IgG2a |
| 7 | 3A5  | IgG2a |
| 8 | 2D1  | IgM   |
| 9 | 2B12 | IgG2a |

Example 2-2: Determination of Amino Acid Sequence of Antibodies

The amino acid sequence of each antibody was determined from the genome information of the hybridomas cloned in Example 1. Table Y illustrates the amino acid sequence of each region (CDR1 to CDR3, and FR1 to FR4) in the heavy-chain variable region of each antibody. Table Z illustrates the amino acid sequence of each region (CDR1 to CDR3, and FR1 to FR4) in the light-chain variable region. In Tables Y and Z, the amino acids are shown with a single alphabet letter, and the sequences are described with the N-terminal side on the left of the uppermost row. The numbers in parentheses indicate the sequence number of each sequence, and "Full" indicates the entire sequence of a heavy-chain variable region or a light-chain variable region (the sequence that is arranged in the order of FR1, CDR1, FR2, CDR2, FR3, CDR3, and FR4 from the N-terminal).

TABLE Y

| mAb  | FR1 | CDR1 | FR2 | CDR2 | FR3 | CDR3 | FR4 | Full |
|------|-----|------|-----|------|-----|------|-----|------|
| 2B12 | QVQLQQSG AELARPGAS VKLSCKAS | GYTFT RF (1) | GMSWVK QRTGQG LEWIGEI | YPGSG D (2) | TYYSENFKGKATLTA DKSSGTAYMELRSL TSEDSAVYFCAR | WGIYY GNPYA MDY (3) | WGQG TSVTV SS | (4) |
| 2B1  | QVQLQQPG AELVKPGAS VKLSCKAS | GYTFT TF (9) | WIHWVK QRPGRG LEWIGRI | APYSG G (10) | TTYNEKFKSKATLTV DRPSTTAYMQLISLT SEDSAVYYCAR | WDFTY GSNLD Y (11) | WGQG TTLTV SS | (12) |
| 4F1  | QVQLQQSG PELVKPGAS VKISCKAS | GYSFT SY (17) | YIHWVK QRPGQG LEWIGWI | YPGSG N (18) | TKYNEKFKGKATLA DTSSSTAYMQLSSL TSEDSAVYYCAS | PYYGS RRDYF DY (19) | WGQG TTLTV SS | (20) |

TABLE Y-continued

| mAb | FR1 | CDR1 | FR2 | CDR2 | FR3 | CDR3 | FR4 | Full |
|-----|-----|------|-----|------|-----|------|-----|------|
| 4D2 | DVQLQESG PGLVKPSQS LSLTCSVT | GYSIT SGY (25) | YWNWIR QFPGNK LEWMGYI | SYDGS (26) | NNYNPSLKNRISITR DTSKNQFFLKLNSV TTEDTATYYCAR | EAYYS NYGFS (27) | WGQG LVTVS A | (28) |
| 1B3 | QIQLVQSGP ELKKPGETV KISCKAS | GYSFT AH (33) | GMSWVK QAPGKG LKWMGW | NTYSG V (34) | PAYADDFKGRFAFS LETSPSTAFLQINNL KNEDTATYFCTR | SHYDR KFGY (35) | WGQG TLVTV SA | (36) |
| 1D1 | QVQLQQPG AEHVKPGAS VKLSCKAS | GYTFT TY (41) | WIHWVK QRPGRG LEWIGRI | APNSG G (42) | TKYNENFKSKATLTV DRPSTTAYMQLSGL TSEDSAVYYCAR | WDFTF GTNLD Y (43) | WGQG TTLTV SS | (44) |
| 3A5 | QVQLQQPG TELVKPGAS VKLSCKAS | GYTFT SY (49) | WMHWVK QRPGQG LEWIGNI | NPSNG G (50) | TNYNEKFKSKATLTV DKSSTTAYMLLSSLT SEDSAVYYCAR | YYGSS FLYWY FDV (51) | WGTGT TVTVS S | (52) |
| 2D1 | QVQLQQPG AELVKPGAS VKLSCKAS | GYTFT SY (57) | WMHWVK QRPGRG LEWIGRI | DPNSG G (58) | TKYNEKFKSKATLTV DKPSSTAYMQLSSL TSEDSAVYYCAR | WGTG DY (59) | WGQG TTLTV SS | (60) |
| 4A1 | QVQLQQSG AELARPGAS VKLSCKAS | GYTFT SY (65) | GISWVN QRTGQG LEWIGEI | YPRGS N (66) | TYFNEKFQGKATLTA DKSSSTAYMELRSL TSEDSAVFFCAR | PYEGY FDY (67) | WGQG TTLTV SS | (68) |

TABLE Z

Light-Chain Variable Region

| mAb | FR1 | CDR1 | FR2 | CDR2 | FR3 | CDR3 | FR4 | Full |
|-----|-----|------|-----|------|-----|------|-----|------|
| 2B12 | DIVMTQAAP SVPVTPGES VSISC | RSSKSLL HSNGNTY LY (5) | WFLQR PGQSP QLLIY | RMSNL AS (6) | GVPDRFSGSG SGTAFTLRISR VEAEDVGVYYC | LQHLE YPFT (7) | FGSGT KLEIK RA | (8) |
| 2B1 | DIVMTQSQK FMSTSVGD RVSIPC | KASQNVR TAVA (13) | WYQQK PGQSP KALIY | LASNR HT (14) | GVPDRFTGSGS GTDFTLTISNV QSEDLADYFC | LGHW DYPYT (15) | FGGGT KLEIK RA | (16) |
| 4F1 | DIVMSQSPS SLAVSVGEK VTMSC | KSSQSLL YSSNQKN YLA (21) | WYQQK PGQSP KLLIY | WASTR ES (22) | GVPDRFTGSGS GTDFTLTISSVK AEDLAVYYC | QQYYS YPLT (23) | FGAGT KLELK RA | (24) |
| 4D2 | DIVMSQSPS SLAVSVGEK VTMSC | KSSQSLL YSSNQKN YLA (29) | WYQQK PGQSP KLLIY | WASTR ES (30) | GVPDRFTGSGS GTDFTLTISSVK AEDLAVYYC | QQYYR YPYT (31) | FGGGT KLEIK RA | (32) |
| 1B3 | QAVVTQESA LTTSPGETV TLTC | RSSTGAV TTSNYAN (37) | WVQEK PDHLF TGLIG | DTNNR AP (38) | GVPARFSGSLI GDKAALTITGA QTGDEAIYFC | ALWYS NLWV (39) | FGGGT KLTVR GQP | (40) |
| 1D1 | DIVMTQSQK FMSTSVGD RVSITC | KASQNVR TAVA (45) | WYQQK PGQSP KALIF | LASNR HT (46) | GVPDRFTGSGS GTDFTLTITNV QSEDLADYFC | LQHW TYPYT (47) | FGGGT KLEIK RA | (48) |
| 3A5 | DIVMTQSHK FMSSSVGD RVSITC | KASQDVG TAVA (53) | WYQQK PGQSP KILIY | WASTR HT (54) | GVPDRFTGSGS GTDFTLTISNV QSEDLADYFC | QQYSS YPT (55) | FGSGT KLEIK RA | (56) |
| 2D1 | DIVLTQSPA SLAVSLGQR ATISC | RASKSVS TSGYSYM H (61) | WYQQK PGQPP KLLIY | LASNL ES (62) | GVPARFSGSGS GTDFTLNIHPV EEEDAATYYC | QHSRE LPFT (63) | FGSGT KLEIK RA | (64) |
| 4A1 | DIVLTQSPA SLAVSLGQR ATISC | RASKSVS TSGYSYM H (69) | WYQQK PGQPP KLLIY | LASNL ES (70) | GVPARFSGSGS GTDFTLNIHPV EEEDAATYYC | QHSRE LPFT (71) | FGSGT KLEIK RA | (72) |

Example 2-3: Determination of Kd Values of Antibodies

FACS analysis was performed in the same manner as in Example 1-4 using human Claudin 5 protein-expressing cells obtained in Example 1-3 and antibodies (as primary antibodies). From the obtained data, a saturation bond curve was drawn with the MFI obtained by FACS analysis as Y-axis; and the 50% saturation bond concentration was determined, thereby calculating a Kd value. Table P illustrates the Kd value of each antibody.

TABLE P

| mAb | Kd (nM) |
|---|---|
| 2B12 | 7.3 |
| 2B1 | 6.9 |

Example 3: Antibody Specificity Analysis 1

In the same manner as in Example 1-3, a vector for preparing a retrovirus was prepared by inserting, into a pCX4pur vector, a DNA fragment consisting of the coding sequence of wild-type human Claudin 1 protein (SEQ ID NO: 79), the coding sequence of wild-type human Claudin 2 protein (SEQ ID NO: 80), the coding sequence of wild-type human Claudin 3 protein (SEQ ID NO: 81), the coding sequence of wild-type human Claudin 4 protein (SEQ ID NO: 82), the coding sequence of wild-type human Claudin 6 protein (SEQ ID NO: 83), the coding sequence of wild-type human Claudin 7 protein (SEQ ID NO: 84), the coding sequence of wild-type human Claudin 9 protein (SEQ ID NO: 85), the coding sequence of wild-type mouse Claudin 1 protein (SEQ ID NO: 86), the coding sequence of wild-type mouse Claudin 2 protein (SEQ ID NO: 87), the coding sequence of wild-type mouse Claudin 3 protein (SEQ ID NO: 88), the coding sequence of wild-type mouse Claudin 4 protein (SEQ ID NO: 89), or the coding sequence of wild-type mouse Claudin 5 protein (SEQ ID NO: 90). Then, various Claudin protein-expressing cells were produced using these vectors and the vector for preparing a retrovirus produced in Example 1-3. FACS analysis was performed in the same manner as in Example 1-4 using these cells and each antibody (antibody concentration: 10 μg/ML, used as a primary antibody). FIG. 4 illustrates histograms with the horizontal axis representing the fluorescence signal, and the vertical axis representing the cell count.

As illustrated in FIG. 4, antibodies 2B12 and 2B1 did not bind to human Claudins except for Claudin 5 and mouse Claudins. Antibody 4F1 did not bind to human Claudins except for Claudin 5 and mouse Claudins except for Claudin 5. This suggests that these antibodies are highly specific for human Claudin 5, Example 4: Antibody Specificity Analysis 2

Figure 5:
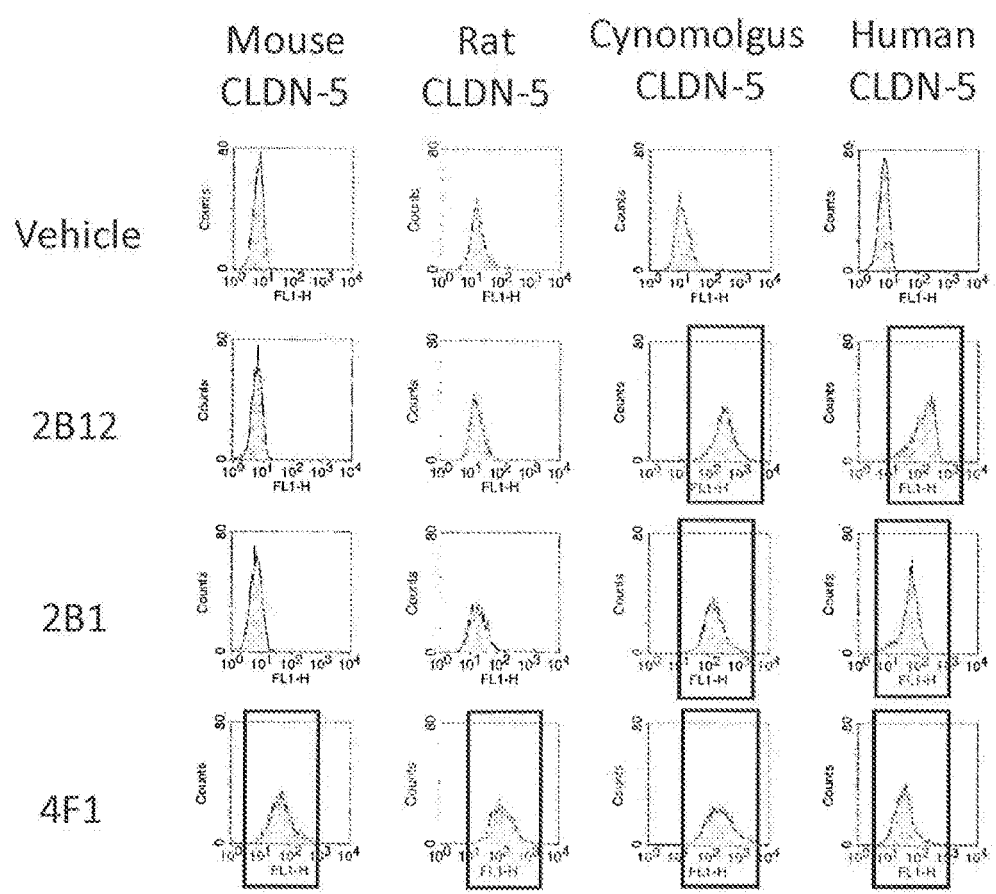
FIG. 5 illustrates FACS histograms showing the results of specificity analysis (Example 4) of the antibodies obtained in Example 1. Shown at the top of the histograms is the name of the Claudin proteins expressed in cells using a retrovirus. The antibodies used as a primary antibody are shown on the leftmost side of the histograms. In each histogram, the horizontal axis represents the fluorescence signal, and the vertical axis represents the cell count. Peaks that are shifted to the right (on the side of stronger fluorescent signals), as compared with peaks of the case in which the antibody was not reacted (vehicle), are indicated within square boxes.

In the same manner as in Example 1-3, a vector for preparing a retrovirus was prepared by inserting a DNA fragment consisting of the coding sequence of wild-type rat Claudin 5 protein (SEQ ID 91) or the coding sequence of wild-type monkey Claudin 5 protein (SEQ ID NO: 92) into a pCX4pur vector. Then, various Claudin protein-expressing cells were produced using these vectors, and the vectors for preparing a retrovirus prepared in Example 1-3 and Example 3. FACS analysis was performed in the same manner as in Example 1-4 using these cells and each antibody (antibody concentration: 10 μg/mL, used as a primary antibody). FIG. 5 illustrates histograms with the horizontal axis representing the fluorescence signal, and the vertical axis representing the cell count. FIG. 6 illustrates a comparison of the amino acid sequences of Claudin 5 protein of different species.

As shown in FIG. 5, antibodies 2B12 and 2B1 did not bind to mouse Claudin 5 and rat Claudin 5. However, antibody 4F1 bound to Claudin 5 of humans, monkeys, mice, and rats.

Example 5: Antibody Epitope Analysis 1

Figure 7:
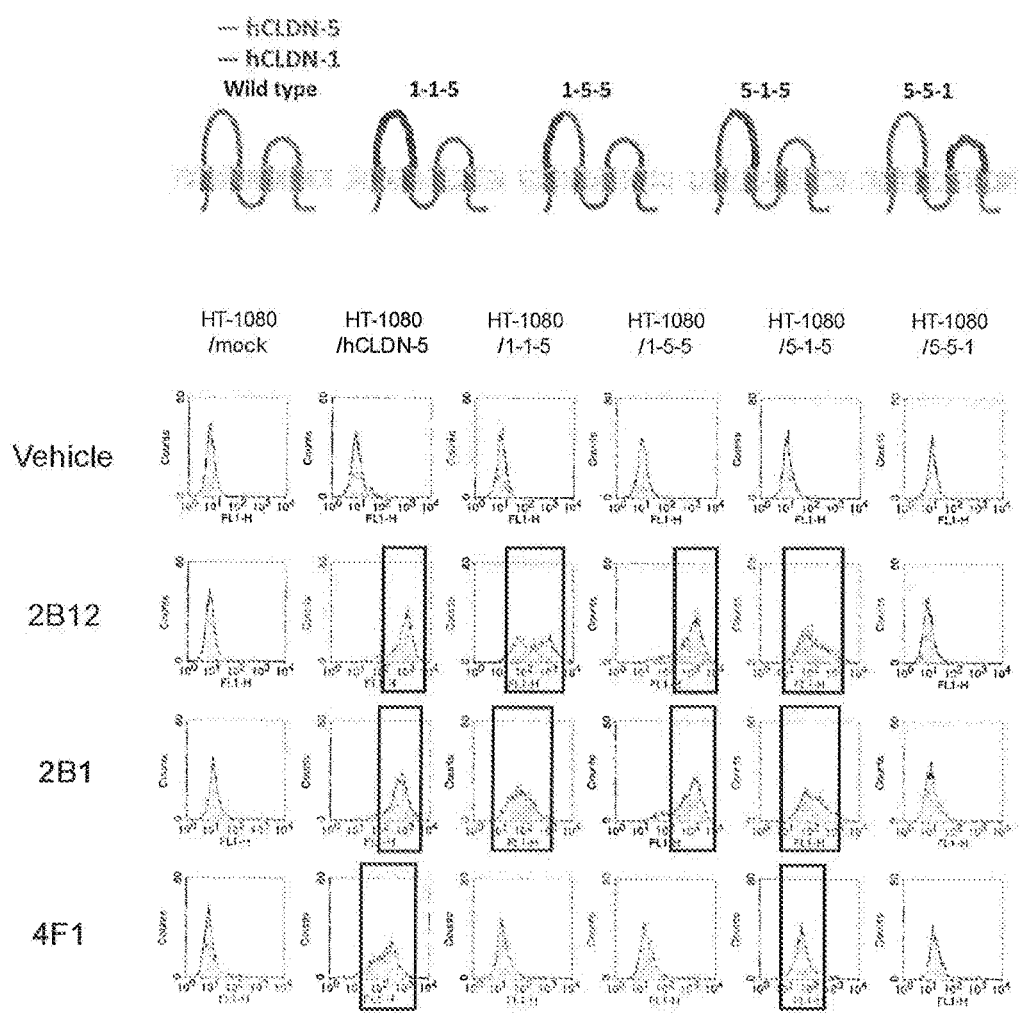
FIG. 7 illustrates FACS histograms showing the results of epitope analysis (Example 5) of the antibodies obtained in Example 1. Shown at the top of the histograms are the names of Claudin proteins expressed in HT-1080 cells using a retrovirus. The antibodies used as a primary antibody are shown on the leftmost side of the histograms. In each histogram, the horizontal axis represents the fluorescence signal, and the vertical axis represents the cell count. Peaks that are shifted to the right (on the side of stronger fluorescent signals), as compared with peaks of the case in which the antibody was not reacted (vehicle), are indicated in square boxes. At the top of FIG. 7, the sequence structure of each Claudin protein is shown. In the structures, the sequence of human Claudin 1 is indicated by a bold red line.

In the same manner as in Example 1-3, a vector for preparing a retrovirus was prepared by inserting, into a pCX4pur vector, a DNA fragment consisting of the coding sequence of a chimeric protein of a wild-type human Claudin 5 protein and a wild-type human Claudin 5 protein (1-1-5: a protein in which the first extracellular loop of human Claudin 5 protein is replaced with the sequence of human Claudin 1 protein (SEQ ID NO: 93), 1-5-5: a protein in which approximately half of the N-terminal side of the first extracellular loop of human Claudin 5 protein is replaced with the sequence of human Claudin 1 protein (SEQ ID NO: 94), 5-1-5: a protein in which approximately half of the C-terminal side of the first extracellular loop of human Claudin 5 protein is replaced with the sequence of human Claudin 1 protein (SEQ ID NO: 95), and 5-5-1: a protein in which the second extracellular loop of human Claudin 5 protein is replaced with the sequence of Claudin 1 protein (SEQ ID NO: 96)). Various Claudin protein-expressing cells were prepared using these vectors, and the vector for preparing a retrovirus produced in Example 1-3. FACS analysis was performed in the same manner as in Example 1-4 using these cells and each antibody (antibody concentration: 10 μg/mL, used as a primary antibody). FIG. 7 illustrates histograms with the horizontal axis representing the fluorescence signal, and the vertical axis representing the cell count. FIG. 8 illustrates a comparison of the amino acid sequences of these chimeric proteins.

FIG. 7 suggests that antibodies 2B12 and 2B1 recognize the second extracellular loop, and that antibody 4F1 recognizes both the first extracellular loop and the second extracellular loop, Example 6: Antibody Epitope Analysis 2

Figure 9:
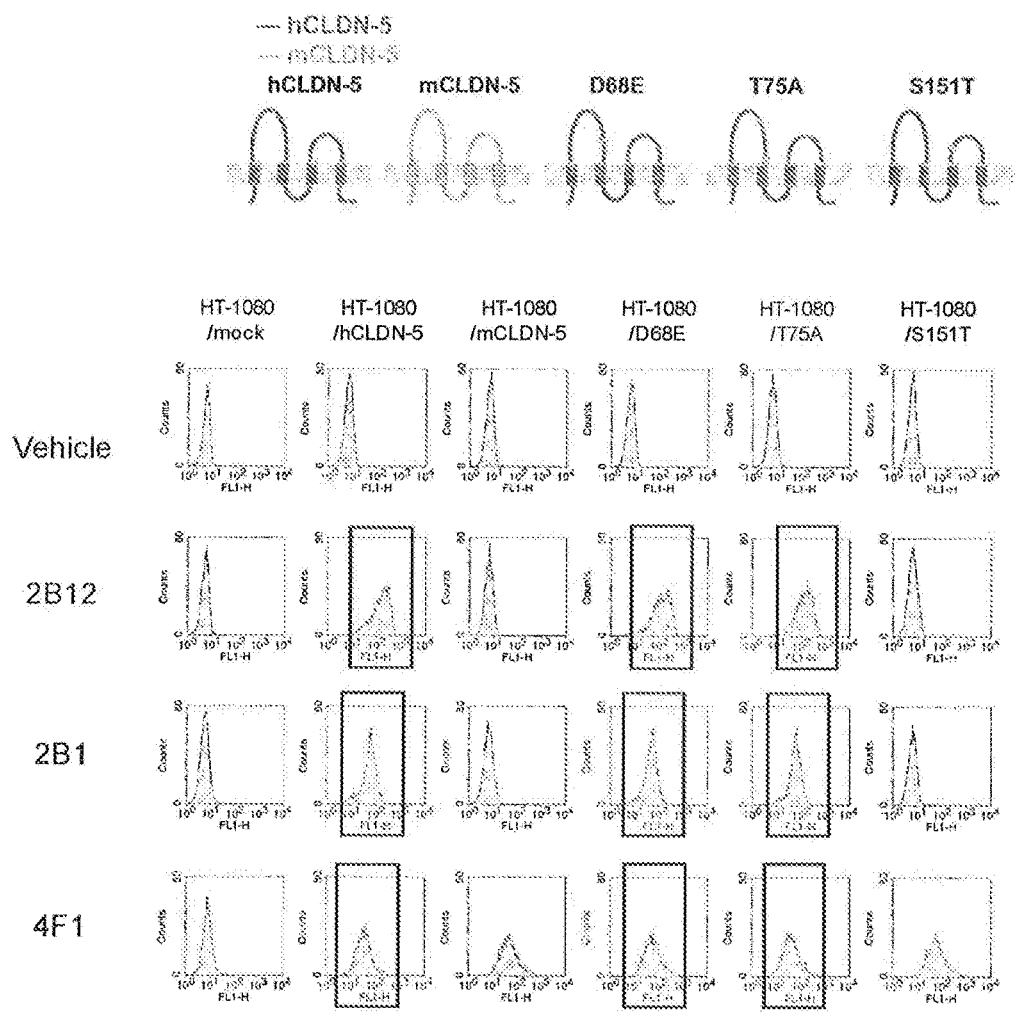
FIG. 9 illustrates FACS histograms showing the results of epitope analysis (Example 6) of the antibodies obtained in Example 1. Shown at the top of the histograms are the names of the Claudin proteins expressed in cells using a retrovirus. The antibodies used as a primary antibody are shown on the leftmost side of the histograms. In each histogram, the horizontal axis represents the fluorescence signal, and the vertical axis represents the cell count. Peaks that are shifted to the right (on the side of stronger fluorescent signals), as compared with peaks of the case in which the antibody was not reacted (vehicle), are indicated within square boxes. At the top of FIG. 9, the sequence structure of each Claudin protein is shown. In the structure of a point mutant, the point mutation site is indicated by a solid circle.

In the same manner as in Example 1-3, a vector for preparing a retrovirus was prepared by inserting, into a pCX4pur vector, a DNA fragment consisting of the coding sequence of a point mutant of wild-type human Claudin 5 protein (D68E: a protein in which the 68th amino acid (aspartic acid) from the N-terminal in human Claudin 5 protein is replaced with glutamic acid, which is the amino acid at the corresponding position in mouse Claudin 5 protein (SEQ ID NO: 97); a protein in which the 75th amino acid (threonine) from the N-terminal in human Claudin 5 protein is replaced with alanine, which is the amino acid at the corresponding position in mouse Claudin 5 protein (SEQ ID NO: 98); and a protein in which the 151st amino acid (serine) from the N-terminal in human Claudin 5 protein is replaced with threonine, which is the amino acid at the corresponding position in mouse Claudin 5 protein (SEQ ID NO: 99)). Then, various Claudin protein-expressing cells were produced using these vectors, and the vectors for preparing a retrovirus prepared in Example 1-3 and Example 3. FACS analysis was performed in the same manner as in Example 1-4 using these cells and each antibody (antibody concentration: 10 μg/mL, used as a primary antibody). FIG. 9 illustrates histograms with the horizontal axis representing a fluorescence signal, and the vertical axis representing the cell count.

FIG. 9 suggests that antibodies 2B12 and 2B1 recognize human-specific amino acids within the second extracellular loop.

Example 7: Antibody Epitope Analysis 3

Figure 10:
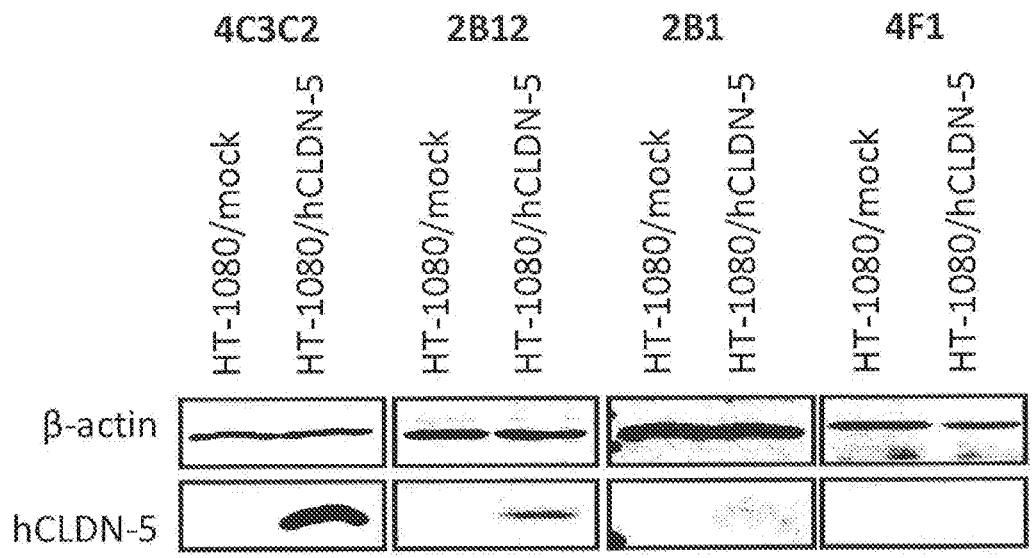
FIG. 10 illustrates Western blotting photographs showing the results of epitope analysis (Example 7) of the antibodies obtained in Example 1. The primary antibody used is shown at the top of each photograph, and the cells used are shown directly below. The name of the protein indicated as a band is shown on the left side of the photographs.

Lysates were prepared from the human Claudin 5 protein-expressing cells prepared in Example 1-3 or mock cells, and the lysates were separated by SDS-PAGE under reducing conditions. Western blotting was then performed in accordance with a standard method using each antibody prepared in Example 1 as a primary antibody (antibody concentration: 10 μg/mL). A commercially available monoclonal antibody (4C3C2), which recognizes the C-terminal of Claudin 5, and β-actin antibody were also used as primary antibodies, respectively as a positive control and a loading control. FIG. 10 illustrates the results, FIG. 10 suggests that antibodies 2B12 and 2B1 recognize linear peptides, and that antibody 4F1 recognizes the three-dimensional structure of Claudin 5.

Example 8: Evaluation of Barrier Function Control Activity of Antibody 1

Figure 11:
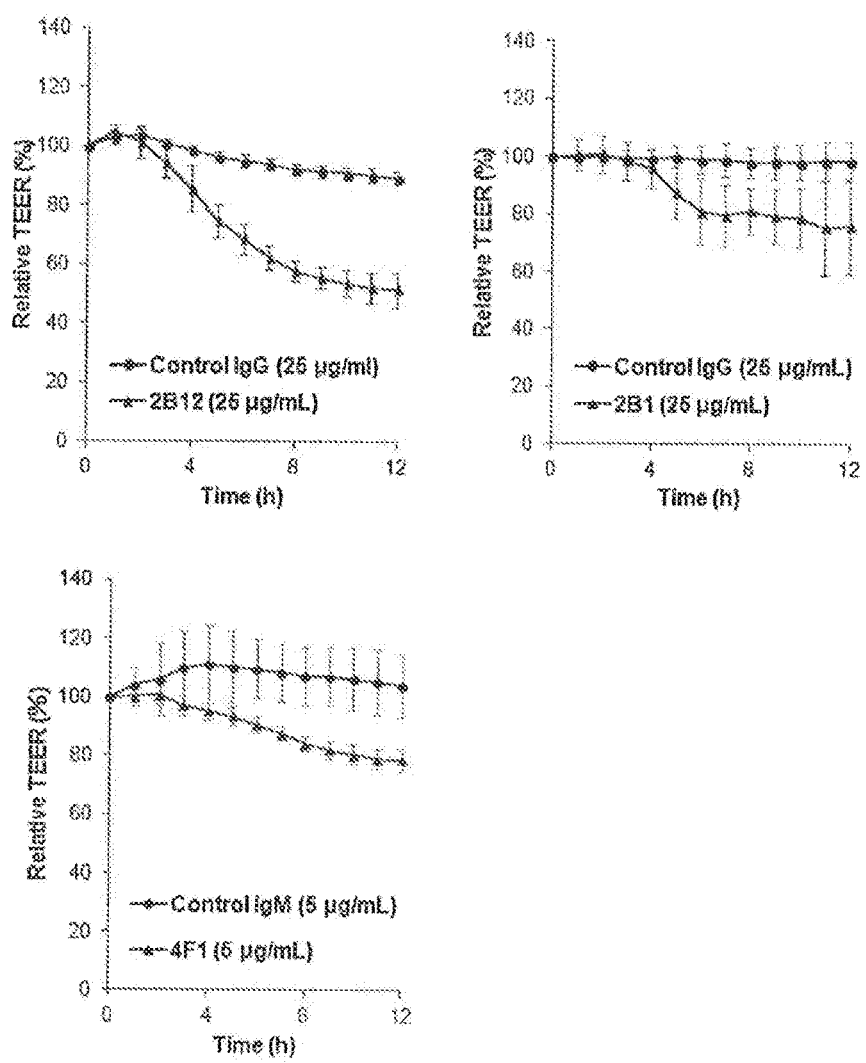
FIG. 11 illustrates graphs showing the results of the evaluation of barrier function control activity of the antibodies obtained in Example 1 (Example 8). In each graph, the vertical axis represents the trans-epithelial/endothelial electrical resistance, and the horizontal axis represents the time period from the addition of an antibody solution, with the concentrations in each graph representing the concentration of each antibody in a culture medium. Each plot indicates a mean (n=4-6), and the bars indicate the standard deviation.

A monolayer culture insert (BD Falcon Inc., catalog number: 353095) with a permeable membrane made of polyethylene terephthalate (pore size 0.4 μm, $1.6 \times 10^6$ pores per $cm^2$) on the bottom surface was set in each well of a 24-well plate. Human dermal microvascular endothelial cells (Lonza Inc., catalog number: CC-2543) were cultured on the membrane to form a monolayer sheet of endothelial cells on each membrane. 10 μL of a solution of each antibody obtained in Example 1, control IgG, or control IgM was added to the medium. After addition, the change in trans-epithelial/endothelial electrical resistance was measured over time using a trans-epithelial/endothelial electrical resistance analyzer (cellZscope, nanoAnalytics Corporation). FIG. 11 illustrates the results.

FIG. 11 suggests that antibodies 2B12, 2B1, and 4F1 have an action to open the junctions between endothelial cells; i.e., antibodies 2B12, 2B1, and 4F1 have activity to control the barrier function of the endothelial cell layers.

Example 9: Evaluation of Barrier Function Control Activity of Antibody 2

Barrier function control activity was evaluated using a cultured product mimicking the blood-brain barrier (a monkey-type BBB kit, PharmaCo-Cell Company Ltd.). The cultured product had a structure in which an insert with a permeable membrane made of polyethylene terephthalate (pore size: 3.0 μm, $1.6 > 10^6$ pores per $cm^2$) on the bottom surface was set in a culture well. A monolayer sheet of monkey brain capillary endothelial cells was formed on the upper side of the bottom surface of the insert, and a cell sheet of rat pericytes was formed on the lower side of the bottom surface, with a cell sheet of rat astrocytes formed on the bottom surface of the culture well.

Figure 12:
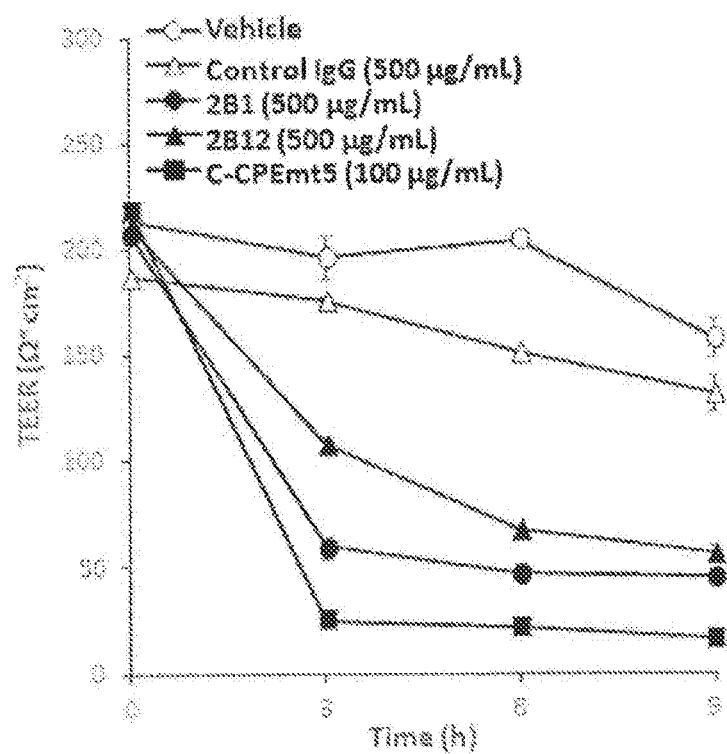
FIG. 12 illustrates a graph showing the results of evaluation of barrier function control activity of the antibodies obtained in Example 1 (Example 9). The vertical axis represents the trans-epithelial/endothelial electrical resistance, and the horizontal axis represents the time period from the addition of a test solution. The concentrations in the graph represent the concentration of a test substance in a medium, and the vehicle represents the addition of the solution used to dilute the antibodies. Each plot indicates a mean (n=3), and the bars indicate the standard deviation.

30 μL of an antibody obtained in Example 1, C-CPE mt5 (a mutant of a C-terminal fragment of an enterotoxin of *Clostridium perfringens*, positive control), a solution of control IgG, or the solution used for dilution of the antibody was added to the medium on the insert side of the cultured product (blood vessel side). After addition, the change of trans-epithelial/endothelial electrical resistance was measured over time using a Millicell-ERS resistance value analyzer (Millipore). FIG. 12 illustrates the results.

FIG. 12 suggests that antibodies 2B12 and 2B1 have an action to open the junctions between cerebrovascular endothelial cells; i.e., antibodies 2B12 and 2B1 have activity to control the barrier function of cerebrovascular endothelial cell layers (=blood-brain barrier control activity).

Example 10: Evaluation of Barrier Function Control Activity of Antibody 3

Figure 13:
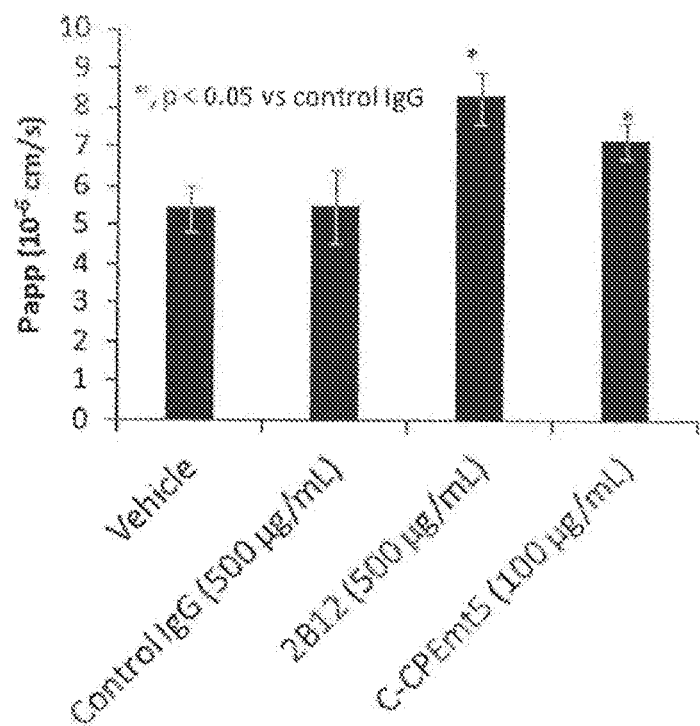
FIG. 13 illustrates a graph showing the results of evaluation of barrier function control activity of the antibodies obtained in Example 1 (Example 10). In the horizontal axis, the concentrations represent the concentration of a test substance in a medium, and the vehicle represents the case in which a solution used to dilute an antibody was added. Each plot indicates a mean (n=3), and the bars indicate the standard deviation. The asterisks indicate that p-value is less than 0.05, in comparison with control IgG.

The cultured product used in Example 9 was used. 30 μL of an antibody obtained in Example 1, C-CPE mt5 (a mutant of a C-terminal fragment of an enterotoxin of *Clostridium perfringens*, positive control), a solution of control IgG, or the solution used for dilution of the antibodies was added to the medium on the insert side of the cultured product (blood vessel side). After 9 hours from addition, the inserts were transferred to a 24-well plate (a plate for washing, Greiner) to which 900 μL of a medium was added beforehand, and the medium on the insert side was replaced once. Thereafter, the medium on the insert side was suctioned, and 200 μL of a medium containing 10 μg/mL of a fluorescein sodium salt (Wako Pure Chemical Industries) was added thereto. The inserts were then transferred to a 24-well plate (a plate for measurement, Greiner) to which 900 μL of a medium was added beforehand on a HIENAI plate warmer (Cosmo Bio). After 30 minutes from transfer to the plate for measurement, the inserts were sequentially transferred to a plate for washing. The fluorescence intensity of the medium in the plate for measurement (brain-side) was measured with a TriStar LB 941 microplate reader (Berthold Technologies). The apparent permeability coefficient (Papp) was calculated with the following equation: Papp(cm/s)=(the amount of a medium on the brain side×the concentration of a fluorescein sodium salt that has penetrated into the brain side)/(the surface area of the permeation membrane of an insert×the concentration of the fluorescein sodium salt added on the blood vessel side×experimental time). FIG. 13 illustrates the results.

FIG. 13 suggests that antibody 2B12 has an action to open the junctions between cerebrovascular endothelial cells, and to stimulate the permeation of substances; i.e., antibody 2B12 has activity to control the barrier function of the cerebrovascular endothelial cell layers (=blood-brain barrier control activity).

Example 11: Evaluation of Barrier Function Control Activity of Antibody 4

Figure 14:
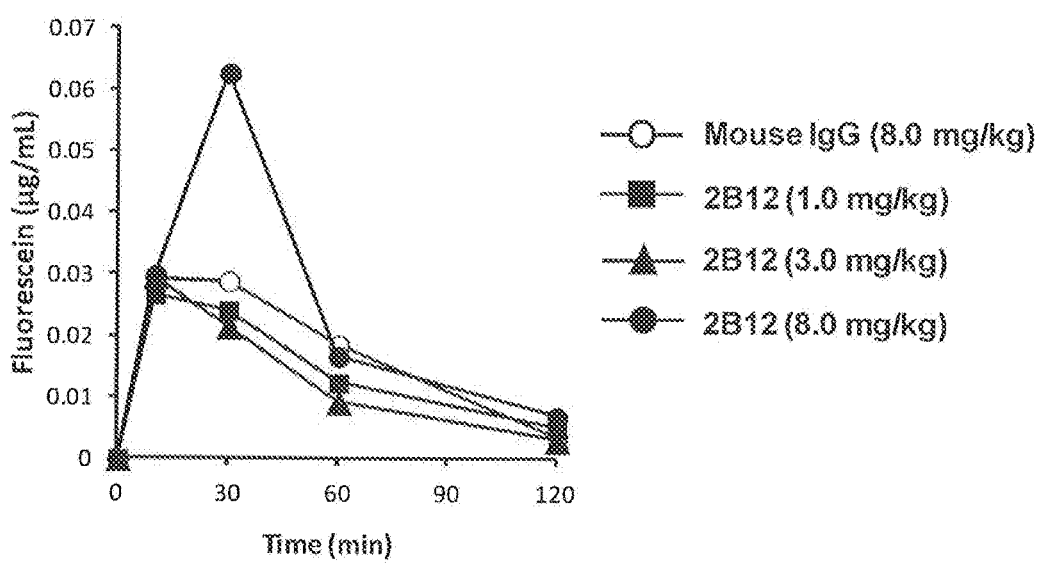
FIG. 14 illustrates a graph showing the results of evaluation of barrier function control activity of the antibodies obtained in Example 1 (Example 11). The vertical axis represents the concentration of a fluorescent dye in the cerebrospinal fluid, and the horizontal axis represents the time period from the administration of the fluorescent dye.

The blood-brain barrier control activity of antibodies was evaluated using crab-eating monkeys. Specifically, the evaluation was performed as described below.
Administration of Antibodies and Fluorescent Dye to Crab-Eating Monkeys This process was outsourced to Hamamatsu Pharma Research (Shizuoka). On days 1, 8, 15, and 22 of the experiment, the antibodies obtained in Example 1 were intravenously administered to crab-eating monkeys (3 years old, male, EveBioscience Co., Ltd., Wakayama) (day 1: mouse IgG, 8 mg/kg; day 8: 2B12, 1 mg/kg; day 15: 2B12, 3 mg/kg; and day 22: 2B12, 8 mg/kg). The day following administration, a fluorescein sodium salt (20 mg/kg), which is a fluorochrome, was intravenously administered to the monkeys under ketamine anesthesia. Immediately before administration, and 10, 30, 60, and 120 minutes after administration, cerebrospinal fluid and venous blood were collected.
Measurement of Fluorochrome in Cerebrospinal Fluid The molecular weight of fluorescent molecules in the collected cerebrospinal fluid was measured with a fluorescence plate reader (TriStar LB 941). FIG. 14 illustrates the results.
Measurement of Toxicity Markers in Venous Blood (Plasma)

The concentration of hepatotoxicity markers (AST, ALT) and a hepato-nephrotoxicity marker (BUN) in the collected plasma was measured using a measurement kit (Test Wako, Wako Pure Chemical Industries, Ltd.). Table Q illustrates the results.

TABLE Q

|  | Mouse IgG (8.0 mg/kg) | 2B12 (1.0 mg/kg) | 2B12 (3.0 mg/kg) | 2B12 (8.0 mg/kg) |
|---|---|---|---|---|
| AST (IU/L) | 54.3 | 36.8 | 31.0 | 34.8 |
| ALT (IU/L) | 29.9 | 25.4 | 21.8 | 23.8 |
| BUN (mg/dL) | 20.0 | 20.9 | 15.7 | 20.2 |

Results

After 30 minutes from the administration of Claudin-5 antibodies at a dose of 8 mg/kg, the fluorescent dye in the cerebrospinal fluid was increased. This increase was not observed when the control antibody was administered in the same amount. Additionally, there was no significant change in hepato-nephrotoxicity marker in the blood when the fluorochrome was increased. These results indicate that Claudin-5 antibodies promote the passage of a low-molecular compound through the monkey blood-brain barrier, without significant toxicity.

Sequence Listing

P17-198WO_PCT_Claudin5 antibody-20171204_115533_5.txt

The invention claimed is:

1. An antibody whose epitope is a region within an extracellular domain of Claudin 5 protein and wherein the antibody is selected from the group consisting of the following antibodies A to I:

(A) antibody A comprising: a heavy-chain variable region comprising:
heavy-chain CDR1 comprising the amino acid sequence represented by SEQ ID NO: 1,
heavy-chain CDR2 comprising the amino acid sequence represented by SEQ ID NO: 2, and
heavy-chain CDR3 comprising the amino acid sequence represented by SEQ ID NO: 3; and
a light-chain variable region comprising:
light-chain CDR1 comprising the amino acid sequence represented by SEQ ID NO: 5,
light-chain CDR2 comprising the amino acid sequence represented by SEQ ID NO: 6, and
light-chain CDR3 comprising the amino acid sequence represented by SEQ ID NO: 7;

(B) antibody B comprising: a heavy-chain variable region comprising:
heavy-chain CDR1 comprising the amino acid sequence represented by SEQ ID NO: 9,
heavy-chain CDR2 comprising the amino acid sequence represented by SEQ ID NO: 10, and
heavy-chain CDR3 comprising the amino acid sequence represented by SEQ ID NO: 11, and
a light-chain variable region comprising:
light-chain CDR1 comprising the amino acid sequence represented by SEQ ID NO: 13,
light-chain CDR2 comprising the amino acid sequence represented by SEQ ID NO: 14, and
light-chain CDR3 comprising the amino acid sequence represented by SEQ ID NO: 15;

(C) antibody C comprising: a heavy-chain variable region comprising:
heavy-chain CDR1 comprising the amino acid sequence represented by SEQ ID NO: 17,
heavy-chain CDR2 comprising the amino acid sequence represented by SEQ ID NO: 18, and
heavy-chain CDR3 comprising the amino acid sequence represented by SEQ ID NO: 19; and
a light-chain variable region comprising:
light-chain CDR1 comprising the amino acid sequence represented by SEQ ID NO: 21,
light-chain CDR2 comprising the amino acid sequence represented by SEQ ID NO: 22, and
light-chain CDR3 comprising the amino acid sequence represented by SEQ ID NO: 23;

(D) antibody D comprising: a heavy-chain variable region comprising:

heavy-chain CDR1 comprising the amino acid sequence represented by SEQ ID NO: 25,
heavy-chain CDR2 comprising the amino acid sequence represented by SEQ ID NO: 26, and
heavy-chain CDR3 comprising the amino acid sequence represented by SEQ ID NO: 27; and
a light-chain variable region comprising:
light-chain CDR1 comprising the amino acid sequence represented by SEQ ID NO: 29,
light-chain CDR2 comprising the amino acid sequence represented by SEQ ID NO: 30, and
light-chain CDR3 comprising the amino acid sequence represented by SEQ ID NO: 31;
(E) antibody E comprising: a heavy-chain variable region comprising:
heavy-chain CDR1 comprising the amino acid sequence represented by SEQ ID NO: 33,
heavy-chain CDR2 comprising the amino add sequence represented by SEQ ID NO: 34, and
heavy-chain CDR3 comprising the amino add sequence represented by SEQ ID NO: 35; and
a light-chain variable region comprising:
light-chain CDR1 comprising the amino add sequence represented by SEQ ID NO: 37,
light-chain CDR2 comprising the amino add sequence represented by SEQ ID NO: 38, and
light-chain CDR3 comprising the amino add sequence represented by SEQ ID NO: 39;
(F) antibody F comprising: a heavy-chain variable region comprising:
heavy-chain CDR1 comprising the amino acid sequence represented by SEQ ID NO: 41,
heavy-chain CDR2 comprising the amino acid sequence represented by SEQ ID NO: 42, and
heavy-chain CDR3 comprising the amino acid sequence represented by SEQ ID NO: 43; and
a light-chain variable region comprising:
light-chain CDR1 comprising the amino acid sequence represented by SEQ ID NO: 45,
light-chain CDR2 comprising the amino acid sequence represented by SEQ ID NO: 46, and
light-chain CDR3 comprising the amino acid sequence represented by SEQ ID NO: 47;
(G) antibody G comprising: a heavy-chain variable region comprising:
heavy-chain CDR1 comprising the amino acid sequence represented by SEQ ID NO: 49,
heavy-chain CDR2 comprising the amino acid sequence represented by SEQ ID NO: 50, and
heavy-chain CDR3 comprising the amino acid sequence represented by SEQ ID NO: 51; and
a light-chain variable region comprising:
light-chain CDR1 comprising the amino acid sequence represented by SEQ ID NO: 53,
light-chain CDR2 comprising the amino acid sequence represented by SEQ ID NO: 54, and
light-chain CDR3 comprising the amino acid sequence represented by SEQ ID NO: 55;
(H) antibody H comprising: a heavy chain variable region comprising:
heavy-chain CDR1 comprising the amino acid sequence represented by SEQ ID NO: 57,
heavy-chain CDR2 comprising the amino acid sequence represented by SEQ ID NO: 58, and
heavy-chain CDR3 comprising the amino acid sequence represented by SEQ ID NO: 59; and
a light-chain variable region comprising:
light-chain CDR1 comprising the amino acid sequence represented by SEQ ID NO: 61,
light-chain CDR2 comprising the amino acid sequence represented by SEQ ID NO: 62, and
light-chain CDR3 comprising the amino acid sequence represented by SEQ ID NO: 63; and
(I) antibody I comprising: a heavy-chain variable region comprising:
heavy-chain CDR1 comprising the amino acid sequence represented by SEQ ID NO: 65,
heavy chain CDR2 comprising the amino acid sequence represented by SEQ ID NO: 66, and
heavy-chain CDR3 comprising the amino acid sequence represented by SEQ ID NO: 67; and
a light-chain variable region comprising:
light-chain CDR1 comprising the amino acid sequence represented by SEQ ID NO: 69,
light-chain CDR2 comprising the amino acid sequence represented by SEQ ID NO: 70, and
light-chain CDR3 comprising the amino acid sequence represented by SEQ ID NO: 71.

2. The antibody according to claim 1, wherein the epitope is at least one member selected from the group consisting of a region within a first extracellular loop C terminal side of Claudin 5 protein, a region within a second extracellular loop of Claudin 5 protein, and a three-dimensional structure formed from the first extracellular loop and the second extracellular loop.

3. The antibody according to claim 1, wherein the epitope is a region within the second extracellular loop of Claudin 5 protein.

4. The antibody according to claim 3, wherein the epitope is a region containing 151st amino acid from the N-terminal in human Claudin 5 protein comprising the amino acid sequence represented by SEQ ID NO: 73, or an amino acid in another Claudin 5 protein corresponding to the 151st amino acid.

5. The antibody according to claim 3, wherein the affinity of the antibody to human Claudin 5 protein point mutant S151T comprising the amino acid sequence represented by SEQ ID NO: 99 is ⅕ or less of the affinity thereof to human Claudin 5 protein comprising the amino acid sequence represented by SEQ ID NO: 73.

6. The antibody according to claim 1, wherein the epitope is a three-dimensional structure formed from the first extracellular loop and second extracellular loop of Claudin 5 protein.

7. The antibody according to claim 1, wherein the affinity of the antibody to Claudin family proteins other than Claudin 5 protein is ⅕ or less of the affinity thereof to Claudin 5 protein.

8. The antibody according to claim 1, which is selected from the group consisting of antibodies A and B.

9. The antibody according to claim 1, which is a monoclonal antibody.

10. A polynucleotide that encodes the antibody according to claim 1.

11. A cell comprising the polynucleotide according to claim 10.

12. A complex of the antibody according to claim 1 and a drug.

13. A pharmaceutical composition comprising at least one member selected from the group consisting of the antibody according to claim 1 and a complex of the antibody and a drug.

14. The pharmaceutical composition according to claim 13, which is for blood-brain barrier control.

15. A reagent comprising at least one member selected from the group consisting of the antibody according to claim 1 and a complex of the antibody and a drug.

* * * * *

```
                        SEQUENCE LISTING

<160> NUMBER OF SEQ ID NOS: 99

<210> SEQ ID NO 1
<211> LENGTH: 7
<212> TYPE: PRT
<213> ORGANISM: Artificial Sequence
<220> FEATURE:
<223> OTHER INFORMATION: 2B12 heavy chain CDR1

<400> SEQUENCE: 1

Gly Tyr Thr Phe Thr Arg Phe
1               5

<210> SEQ ID NO 2
<211> LENGTH: 6
<212> TYPE: PRT
<213> ORGANISM: Artificial Sequence
<220> FEATURE:
<223> OTHER INFORMATION: 2B12 heavy chain CDR2

<400> SEQUENCE: 2

Tyr Pro Gly Ser Gly Asp
1               5

<210> SEQ ID NO 3
<211> LENGTH: 13
<212> TYPE: PRT
<213> ORGANISM: Artificial Sequence
<220> FEATURE:
<223> OTHER INFORMATION: 2B12 heavy chain CDR3

<400> SEQUENCE: 3

Trp Gly Ile Tyr Tyr Gly Asn Pro Tyr Ala Met Asp Tyr
1               5                   10

<210> SEQ ID NO 4
<211> LENGTH: 122
<212> TYPE: PRT
<213> ORGANISM: Artificial Sequence
<220> FEATURE:
<223> OTHER INFORMATION: 2B12 Heavy chain variable region

<400> SEQUENCE: 4

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Arg Phe
            20                  25                  30

Gly Met Ser Trp Val Lys Gln Arg Thr Gly Gln Gly Leu Glu Trp Ile
        35                  40                  45

Gly Glu Ile Tyr Pro Gly Ser Gly Asp Thr Tyr Tyr Ser Glu Asn Phe
    50                  55                  60
```

```
Lys Gly Lys Ala Thr Leu Thr Ala Asp Lys Ser Ser Gly Thr Ala Tyr
 65                  70                  75                  80

Met Glu Leu Arg Ser Leu Thr Ser Glu Asp Ser Ala Val Tyr Phe Cys
                 85                  90                  95

Ala Arg Trp Gly Ile Tyr Tyr Gly Asn Pro Tyr Ala Met Asp Tyr Trp
            100                 105                 110

Gly Gln Gly Thr Ser Val Thr Val Ser Ser
        115                 120

<210> SEQ ID NO 5
<211> LENGTH: 16
<212> TYPE: PRT
<213> ORGANISM: Artificial Sequence
<220> FEATURE:
<223> OTHER INFORMATION: 2B12 light chain CDR1

<400> SEQUENCE: 5

Arg Ser Ser Lys Ser Leu Leu His Ser Asn Gly Asn Thr Tyr Leu Tyr
1               5                   10                  15

<210> SEQ ID NO 6
<211> LENGTH: 7
<212> TYPE: PRT
<213> ORGANISM: Artificial Sequence
<220> FEATURE:
<223> OTHER INFORMATION: 2B12 light chain CDR2

<400> SEQUENCE: 6

Arg Met Ser Asn Leu Ala Ser
1               5

<210> SEQ ID NO 7
<211> LENGTH: 9
<212> TYPE: PRT
<213> ORGANISM: Artificial Sequence
<220> FEATURE:
<223> OTHER INFORMATION: 2B12 light chain CDR3

<400> SEQUENCE: 7

Leu Gln His Leu Glu Tyr Pro Phe Thr
1               5

<210> SEQ ID NO 8
<211> LENGTH: 114
<212> TYPE: PRT
<213> ORGANISM: Artificial Sequence
<220> FEATURE:
<223> OTHER INFORMATION: 2B12 light chain variable region

<400> SEQUENCE: 8

Asp Ile Val Met Thr Gln Ala Ala Pro Ser Val Pro Thr Pro Gly
1               5                   10                  15

Glu Ser Val Ser Ile Ser Cys Arg Ser Ser Lys Ser Leu Leu His Ser
                 20                  25                  30

Asn Gly Asn Thr Tyr Leu Tyr Trp Phe Leu Gln Arg Pro Gly Gln Ser
             35                  40                  45

Pro Gln Leu Leu Ile Tyr Arg Met Ser Asn Leu Ala Ser Gly Val Pro
     50                  55                  60

Asp Arg Phe Ser Gly Ser Gly Ser Gly Thr Ala Phe Thr Leu Arg Ile
 65                 70                  75                  80

Ser Arg Val Glu Ala Glu Asp Val Gly Val Tyr Tyr Cys Leu Gln His
                85                  90                  95
```

```
Leu Glu Tyr Pro Phe Thr Phe Gly Ser Gly Thr Lys Leu Glu Ile Lys
            100                 105                 110

Arg Ala

<210> SEQ ID NO 9
<211> LENGTH: 7
<212> TYPE: PRT
<213> ORGANISM: Artificial Sequence
<220> FEATURE:
<223> OTHER INFORMATION: 2B1 heavy chain CDR1

<400> SEQUENCE: 9

Gly Tyr Thr Phe Thr Thr Phe
1               5

<210> SEQ ID NO 10
<211> LENGTH: 6
<212> TYPE: PRT
<213> ORGANISM: Artificial Sequence
<220> FEATURE:
<223> OTHER INFORMATION: 2B1 heavy chain CDR2

<400> SEQUENCE: 10

Ala Pro Tyr Ser Gly Gly
1               5

<210> SEQ ID NO 11
<211> LENGTH: 11
<212> TYPE: PRT
<213> ORGANISM: Artificial Sequence
<220> FEATURE:
<223> OTHER INFORMATION: 2B1 heavy chain CDR3

<400> SEQUENCE: 11

Trp Asp Phe Thr Tyr Gly Ser Asn Leu Asp Tyr
1               5                   10

<210> SEQ ID NO 12
<211> LENGTH: 120
<212> TYPE: PRT
<213> ORGANISM: Artificial Sequence
<220> FEATURE:
<223> OTHER INFORMATION: 2B1 Heavy chain variable region

<400> SEQUENCE: 12

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Thr Phe
            20                  25                  30

Trp Ile His Trp Val Lys Gln Arg Pro Gly Arg Gly Leu Glu Trp Ile
        35                  40                  45

Gly Arg Ile Ala Pro Tyr Ser Gly Gly Thr Thr Tyr Asn Glu Lys Phe
    50                  55                  60

Lys Ser Lys Ala Thr Leu Thr Val Asp Arg Pro Ser Thr Thr Ala Tyr
65                  70                  75                  80

Met Gln Leu Ile Ser Leu Thr Ser Glu Asp Ser Ala Val Tyr Tyr Cys
                85                  90                  95

Ala Arg Trp Asp Phe Thr Tyr Gly Ser Asn Leu Asp Tyr Trp Gly Gln
            100                 105                 110

Gly Thr Thr Leu Thr Val Ser Ser
        115                 120
```

```
<210> SEQ ID NO 13
<211> LENGTH: 11
<212> TYPE: PRT
<213> ORGANISM: Artificial Sequence
<220> FEATURE:
<223> OTHER INFORMATION: 2B1 light chain CDR1

<400> SEQUENCE: 13

Lys Ala Ser Gln Asn Val Arg Thr Ala Val Ala
1               5                   10

<210> SEQ ID NO 14
<211> LENGTH: 7
<212> TYPE: PRT
<213> ORGANISM: Artificial Sequence
<220> FEATURE:
<223> OTHER INFORMATION: 2B1 light chain CDR2

<400> SEQUENCE: 14

Leu Ala Ser Asn Arg His Thr
1               5

<210> SEQ ID NO 15
<211> LENGTH: 9
<212> TYPE: PRT
<213> ORGANISM: Artificial Sequence
<220> FEATURE:
<223> OTHER INFORMATION: 2B1 light chain CDR3

<400> SEQUENCE: 15

Leu Gly His Trp Asp Tyr Pro Tyr Thr
1               5

<210> SEQ ID NO 16
<211> LENGTH: 109
<212> TYPE: PRT
<213> ORGANISM: Artificial Sequence
<220> FEATURE:
<223> OTHER INFORMATION: 2B1 light chain variable region

<400> SEQUENCE: 16

Asp Ile Val Met Thr Gln Ser Gln Lys Phe Met Ser Thr Ser Val Gly
1               5                   10                  15

Asp Arg Val Ser Ile Pro Cys Lys Ala Ser Gln Asn Val Arg Thr Ala
            20                  25                  30

Val Ala Trp Tyr Gln Gln Lys Pro Gly Gln Ser Pro Lys Ala Leu Ile
        35                  40                  45

Tyr Leu Ala Ser Asn Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gly His Trp Asp Tyr Pro Tyr
                85                  90                  95

Thr Phe Gly Gly Gly Thr Lys Leu Glu Ile Lys Arg Ala
            100                 105

<210> SEQ ID NO 17
<211> LENGTH: 7
<212> TYPE: PRT
<213> ORGANISM: Artificial Sequence
<220> FEATURE:
<223> OTHER INFORMATION: 4F1 heavy chain CDR1

<400> SEQUENCE: 17
```

Gly Tyr Ser Phe Thr Ser Tyr
1               5

<210> SEQ ID NO 18
<211> LENGTH: 6
<212> TYPE: PRT
<213> ORGANISM: Artificial Sequence
<220> FEATURE:
<223> OTHER INFORMATION: 4F1 heavy chain CDR2

<400> SEQUENCE: 18

Tyr Pro Gly Ser Gly Asn
1               5

<210> SEQ ID NO 19
<211> LENGTH: 12
<212> TYPE: PRT
<213> ORGANISM: Artificial Sequence
<220> FEATURE:
<223> OTHER INFORMATION: 4F1 heavy chain CDR3

<400> SEQUENCE: 19

Pro Tyr Tyr Gly Ser Arg Arg Asp Tyr Phe Asp Tyr
1               5                   10

<210> SEQ ID NO 20
<211> LENGTH: 121
<212> TYPE: PRT
<213> ORGANISM: Artificial Sequence
<220> FEATURE:
<223> OTHER INFORMATION: 4F1 Heavy chain variable region

<400> SEQUENCE: 20

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ser Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Ser Gly Asn Thr Lys Tyr Asn Glu Lys Phe
50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Ser Pro Tyr Tyr Gly Ser Arg Arg Asp Tyr Phe Asp Tyr Trp Gly
            100                 105                 110

Gln Gly Thr Thr Leu Thr Val Ser Ser
        115                 120

<210> SEQ ID NO 21
<211> LENGTH: 17
<212> TYPE: PRT
<213> ORGANISM: Artificial Sequence
<220> FEATURE:
<223> OTHER INFORMATION: 4F1 light chain CDR1

<400> SEQUENCE: 21

Lys Ser Ser Gln Ser Leu Leu Tyr Ser Ser Asn Gln Lys Asn Tyr Leu
1               5                   10                  15

Ala

```
<210> SEQ ID NO 22
<211> LENGTH: 7
<212> TYPE: PRT
<213> ORGANISM: Artificial Sequence
<220> FEATURE:
<223> OTHER INFORMATION: 4F1 light chain CDR2

<400> SEQUENCE: 22

Trp Ala Ser Thr Arg Glu Ser
1               5

<210> SEQ ID NO 23
<211> LENGTH: 9
<212> TYPE: PRT
<213> ORGANISM: Artificial Sequence
<220> FEATURE:
<223> OTHER INFORMATION: 4F1 light chain CDR3

<400> SEQUENCE: 23

Gln Gln Tyr Tyr Ser Tyr Pro Leu Thr
1               5

<210> SEQ ID NO 24
<211> LENGTH: 115
<212> TYPE: PRT
<213> ORGANISM: Artificial Sequence
<220> FEATURE:
<223> OTHER INFORMATION: 4F1 light chain variable region

<400> SEQUENCE: 24

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys Arg Ala
        115

<210> SEQ ID NO 25
<211> LENGTH: 8
<212> TYPE: PRT
<213> ORGANISM: Artificial Sequence
<220> FEATURE:
<223> OTHER INFORMATION: 4D2 heavy chain CDR1

<400> SEQUENCE: 25

Gly Tyr Ser Ile Thr Ser Gly Tyr
1               5

<210> SEQ ID NO 26
<211> LENGTH: 5
<212> TYPE: PRT
<213> ORGANISM: Artificial Sequence
<220> FEATURE:
<223> OTHER INFORMATION: 4D2 heavy chain CDR2
```

<400> SEQUENCE: 26

Ser Tyr Asp Gly Ser
1               5

<210> SEQ ID NO 27
<211> LENGTH: 10
<212> TYPE: PRT
<213> ORGANISM: Artificial Sequence
<220> FEATURE:
<223> OTHER INFORMATION: 4D2  heavy chain CDR3

<400> SEQUENCE: 27

Glu Ala Tyr Tyr Ser Asn Tyr Gly Phe Ser
1               5                   10

<210> SEQ ID NO 28
<211> LENGTH: 119
<212> TYPE: PRT
<213> ORGANISM: Artificial Sequence
<220> FEATURE:
<223> OTHER INFORMATION: 4D2 Heavy chain variable region

<400> SEQUENCE: 28

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Arg Glu Ala Tyr Tyr Ser Asn Tyr Gly Phe Ser Pro Gly Gln Gly
            100                 105                 110

Thr Leu Val Thr Val Ser Ala
        115

<210> SEQ ID NO 29
<211> LENGTH: 17
<212> TYPE: PRT
<213> ORGANISM: Artificial Sequence
<220> FEATURE:
<223> OTHER INFORMATION: 4D2 light chain CDR1

<400> SEQUENCE: 29

Lys Ser Ser Gln Ser Leu Leu Tyr Ser Ser Asn Gln Lys Asn Tyr Leu
1               5                   10                  15

Ala

<210> SEQ ID NO 30
<211> LENGTH: 7
<212> TYPE: PRT
<213> ORGANISM: Artificial Sequence
<220> FEATURE:
<223> OTHER INFORMATION: 4D2 light chain CDR2

<400> SEQUENCE: 30

Trp Ala Ser Thr Arg Glu Ser

<210> SEQ ID NO 31
<211> LENGTH: 9
<212> TYPE: PRT
<213> ORGANISM: Artificial Sequence
<220> FEATURE:
<223> OTHER INFORMATION: 4D2 light chain CDR3

<400> SEQUENCE: 31

Gln Gln Tyr Tyr Arg Tyr Pro Tyr Thr
1               5

<210> SEQ ID NO 32
<211> LENGTH: 115
<212> TYPE: PRT
<213> ORGANISM: Artificial Sequence
<220> FEATURE:
<223> OTHER INFORMATION: 4D2 light chain variable region

<400> SEQUENCE: 32

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Arg Tyr Pro Tyr Thr Phe Gly Gly Gly Thr Lys Leu Glu Ile
            100                 105                 110

Lys Arg Ala
        115

<210> SEQ ID NO 33
<211> LENGTH: 7
<212> TYPE: PRT
<213> ORGANISM: Artificial Sequence
<220> FEATURE:
<223> OTHER INFORMATION: 1B3 heavy chain CDR1

<400> SEQUENCE: 33

Gly Tyr Ser Phe Thr Ala His
1               5

<210> SEQ ID NO 34
<211> LENGTH: 6
<212> TYPE: PRT
<213> ORGANISM: Artificial Sequence
<220> FEATURE:
<223> OTHER INFORMATION: 1B3 heavy chain CDR2

<400> SEQUENCE: 34

Asn Thr Tyr Ser Gly Val
1               5

<210> SEQ ID NO 35
<211> LENGTH: 9
<212> TYPE: PRT

<213> ORGANISM: Artificial Sequence
<220> FEATURE:
<223> OTHER INFORMATION: 1B3 heavy chain CDR3

<400> SEQUENCE: 35

Ser His Tyr Asp Arg Lys Phe Gly Tyr
1               5

<210> SEQ ID NO 36
<211> LENGTH: 118
<212> TYPE: PRT
<213> ORGANISM: Artificial Sequence
<220> FEATURE:
<223> OTHER INFORMATION: 1B3 Heavy chain variable region

<400> SEQUENCE: 36

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ser Phe Thr Ala His
                20                  25                  30

Gly Met Ser Trp Val Lys Gln Ala Pro Gly Lys Gly Leu Lys Trp Met
            35                  40                  45

Gly Trp Ile Asn Thr Tyr Ser Gly Val Pro Ala Tyr Ala Asp Asp Phe
        50                  55                  60

Lys Gly Arg Phe Ala Phe Ser Leu Glu Thr Ser Pro Ser Thr Ala Phe
65                  70                  75                  80

Leu Gln Ile Asn Asn Leu Lys Asn Glu Asp Thr Ala Thr Tyr Phe Cys
                85                  90                  95

Thr Arg Ser His Tyr Asp Arg Lys Phe Gly Tyr Trp Gly Gln Gly Thr
            100                 105                 110

Leu Val Thr Val Ser Ala
        115

<210> SEQ ID NO 37
<211> LENGTH: 14
<212> TYPE: PRT
<213> ORGANISM: Artificial Sequence
<220> FEATURE:
<223> OTHER INFORMATION: 1B3 light chain CDR1

<400> SEQUENCE: 37

Arg Ser Ser Thr Gly Ala Val Thr Thr Ser Asn Tyr Ala Asn
1               5                   10

<210> SEQ ID NO 38
<211> LENGTH: 7
<212> TYPE: PRT
<213> ORGANISM: Artificial Sequence
<220> FEATURE:
<223> OTHER INFORMATION: 1B3 light chain CDR2

<400> SEQUENCE: 38

Asp Thr Asn Asn Arg Ala Pro
1               5

<210> SEQ ID NO 39
<211> LENGTH: 9
<212> TYPE: PRT
<213> ORGANISM: Artificial Sequence
<220> FEATURE:
<223> OTHER INFORMATION: 1B3 light chain CDR3

<400> SEQUENCE: 39

```
Ala Leu Trp Tyr Ser Asn Leu Trp Val
1               5
```

<210> SEQ ID NO 40
<211> LENGTH: 112
<212> TYPE: PRT
<213> ORGANISM: Artificial Sequence
<220> FEATURE:
<223> OTHER INFORMATION: 1B3 light chain variable region

<400> SEQUENCE: 40

```
Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Asp Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Gly Asp Glu Ala Ile Tyr Phe Cys Ala Leu Trp Tyr Ser Asn
                85                  90                  95

Leu Trp Val Phe Gly Gly Gly Thr Lys Leu Thr Val Arg Gly Gln Pro
            100                 105                 110
```

<210> SEQ ID NO 41
<211> LENGTH: 7
<212> TYPE: PRT
<213> ORGANISM: Artificial Sequence
<220> FEATURE:
<223> OTHER INFORMATION: 1D1 heavy chain CDR1

<400> SEQUENCE: 41

```
Gly Tyr Thr Phe Thr Thr Tyr
1               5
```

<210> SEQ ID NO 42
<211> LENGTH: 6
<212> TYPE: PRT
<213> ORGANISM: Artificial Sequence
<220> FEATURE:
<223> OTHER INFORMATION: 1D1 heavy chain CDR2

<400> SEQUENCE: 42

```
Ala Pro Asn Ser Gly Gly
1               5
```

<210> SEQ ID NO 43
<211> LENGTH: 11
<212> TYPE: PRT
<213> ORGANISM: Artificial Sequence
<220> FEATURE:
<223> OTHER INFORMATION: 1D1 heavy chain CDR3

<400> SEQUENCE: 43

```
Trp Asp Phe Thr Phe Gly Thr Asn Leu Asp Tyr
1               5                   10
```

<210> SEQ ID NO 44
<211> LENGTH: 120
<212> TYPE: PRT
<213> ORGANISM: Artificial Sequence
<220> FEATURE:

<223> OTHER INFORMATION: 1D1 Heavy chain variable region

<400> SEQUENCE: 44

```
Gln Val Gln Leu Gln Gln Pro Gly Ala Glu His Val Lys Pro Gly Ala
1               5                   10                  15
Ser Val Lys Leu Ser Cys Lys Ala Ser Gly Tyr Thr Phe Thr Thr Tyr
            20                  25                  30
Trp Ile His Trp Val Lys Gln Arg Pro Gly Arg Gly Leu Glu Trp Ile
        35                  40                  45
Gly Arg Ile Ala Pro Asn Ser Gly Gly Thr Lys Tyr Asn Glu Asn Phe
    50                  55                  60
Lys Ser Lys Ala Thr Leu Thr Val Asp Arg Pro Ser Thr Thr Ala Tyr
65                  70                  75                  80
Met Gln Leu Ser Gly Leu Thr Ser Glu Asp Ser Ala Val Tyr Tyr Cys
                85                  90                  95
Ala Arg Trp Asp Phe Thr Phe Gly Thr Asn Leu Asp Tyr Trp Gly Gln
            100                 105                 110
Gly Thr Thr Leu Thr Val Ser Ser
        115                 120
```

<210> SEQ ID NO 45
<211> LENGTH: 11
<212> TYPE: PRT
<213> ORGANISM: Artificial Sequence
<220> FEATURE:
<223> OTHER INFORMATION: 1D1 light chain CDR1

<400> SEQUENCE: 45

```
Lys Ala Ser Gln Asn Val Arg Thr Ala Val Ala
1               5                   10
```

<210> SEQ ID NO 46
<211> LENGTH: 7
<212> TYPE: PRT
<213> ORGANISM: Artificial Sequence
<220> FEATURE:
<223> OTHER INFORMATION: 1D1 light chain CDR2

<400> SEQUENCE: 46

```
Leu Ala Ser Asn Arg His Thr
1               5
```

<210> SEQ ID NO 47
<211> LENGTH: 9
<212> TYPE: PRT
<213> ORGANISM: Artificial Sequence
<220> FEATURE:
<223> OTHER INFORMATION: 1D1 light chain CDR3

<400> SEQUENCE: 47

```
Leu Gln His Trp Thr Tyr Pro Tyr Thr
1               5
```

<210> SEQ ID NO 48
<211> LENGTH: 109
<212> TYPE: PRT
<213> ORGANISM: Artificial Sequence
<220> FEATURE:
<223> OTHER INFORMATION: 1D1 light chain variable region

<400> SEQUENCE: 48

```
Asp Ile Val Met Thr Gln Ser Gln Lys Phe Met Ser Thr Ser Val Gly
1               5                   10                  15
```

Asp Arg Val Ser Ile Thr Cys Lys Ala Ser Gln Asn Val Arg Thr Ala
            20                  25                  30

Val Ala Trp Tyr Gln Gln Lys Pro Gly Gln Ser Pro Lys Ala Leu Ile
        35                  40                  45

Phe Leu Ala Ser Asn Arg His Thr Gly Val Pro Asp Arg Phe Thr Gly
50                  55                  60

Ser Gly Ser Gly Thr Asp Phe Thr Leu Thr Ile Thr Asn Val Gln Ser
65                  70                  75                  80

Glu Asp Leu Ala Asp Tyr Phe Cys Leu Gln His Trp Thr Tyr Pro Tyr
                85                  90                  95

Thr Phe Gly Gly Gly Thr Lys Leu Glu Ile Lys Arg Ala
            100                 105

<210> SEQ ID NO 49
<211> LENGTH: 7
<212> TYPE: PRT
<213> ORGANISM: Artificial Sequence
<220> FEATURE:
<223> OTHER INFORMATION: 3A5 heavy chain CDR1

<400> SEQUENCE: 49

Gly Tyr Thr Phe Thr Ser Tyr
1               5

<210> SEQ ID NO 50
<211> LENGTH: 6
<212> TYPE: PRT
<213> ORGANISM: Artificial Sequence
<220> FEATURE:
<223> OTHER INFORMATION: 3A5 heavy chain CDR2

<400> SEQUENCE: 50

Asn Pro Ser Asn Gly Gly
1               5

<210> SEQ ID NO 51
<211> LENGTH: 13
<212> TYPE: PRT
<213> ORGANISM: Artificial Sequence
<220> FEATURE:
<223> OTHER INFORMATION: 3A5 heavy chain CDR3

<400> SEQUENCE: 51

Tyr Tyr Gly Ser Ser Phe Leu Tyr Trp Tyr Phe Asp Val
1               5                   10

<210> SEQ ID NO 52
<211> LENGTH: 122
<212> TYPE: PRT
<213> ORGANISM: Artificial Sequence
<220> FEATURE:
<223> OTHER INFORMATION: 3A5 Heavy chain variable region

<400> SEQUENCE: 52

Gln Val Gln Leu Gln Gln Pro Gly Thr Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Asn Ile Asn Pro Ser Asn Gly Gly Thr Asn Tyr Asn Glu Lys Phe
50                  55                  60

```
Lys Ser Lys Ala Thr Leu Thr Val Asp Lys Ser Ser Thr Thr Ala Tyr
 65                  70                  75                  80

Met Leu Leu Ser Ser Leu Thr Ser Glu Asp Ser Ala Val Tyr Tyr Cys
                 85                  90                  95

Ala Arg Tyr Tyr Gly Ser Ser Phe Leu Tyr Trp Tyr Phe Asp Val Trp
            100                 105                 110

Gly Thr Gly Thr Thr Val Thr Val Ser Ser
        115                 120

<210> SEQ ID NO 53
<211> LENGTH: 11
<212> TYPE: PRT
<213> ORGANISM: Artificial Sequence
<220> FEATURE:
<223> OTHER INFORMATION: 3A5 light chain CDR1

<400> SEQUENCE: 53

Lys Ala Ser Gln Asp Val Gly Thr Ala Val Ala
 1               5                  10

<210> SEQ ID NO 54
<211> LENGTH: 7
<212> TYPE: PRT
<213> ORGANISM: Artificial Sequence
<220> FEATURE:
<223> OTHER INFORMATION: 3A5 light chain CDR2

<400> SEQUENCE: 54

Trp Ala Ser Thr Arg His Thr
 1               5

<210> SEQ ID NO 55
<211> LENGTH: 8
<212> TYPE: PRT
<213> ORGANISM: Artificial Sequence
<220> FEATURE:
<223> OTHER INFORMATION: 3A5 light chain CDR3

<400> SEQUENCE: 55

Gln Gln Tyr Ser Ser Tyr Pro Thr
 1               5

<210> SEQ ID NO 56
<211> LENGTH: 108
<212> TYPE: PRT
<213> ORGANISM: Artificial Sequence
<220> FEATURE:
<223> OTHER INFORMATION: 3A5 light chain variable region

<400> SEQUENCE: 56

Asp Ile Val Met Thr Gln Ser His Lys Phe Met Ser Ser Val Gly
 1               5                  10                  15

Asp Arg Val Ser Ile Thr Cys Lys Ala Ser Gln Asp Val Gly Thr Ala
                 20                  25                  30

Val Ala Trp Tyr Gln Gln Lys Pro Gly Gln Ser Pro Lys Ile Leu Ile
             35                  40                  45

Tyr Trp Ala Ser Thr Arg His Thr Gly Val Pro Asp Arg Phe Thr Gly
         50                  55                  60

Ser Gly Ser Gly Thr Asp Phe Thr Leu Thr Ile Ser Asn Val Gln Ser
 65                  70                  75                  80

Glu Asp Leu Ala Asp Tyr Phe Cys Gln Gln Tyr Ser Ser Tyr Pro Thr
                 85                  90                  95
```

Phe Gly Ser Gly Thr Lys Leu Glu Ile Lys Arg Ala
            100                 105

<210> SEQ ID NO 57
<211> LENGTH: 7
<212> TYPE: PRT
<213> ORGANISM: Artificial Sequence
<220> FEATURE:
<223> OTHER INFORMATION: 2D1 heavy chain CDR1

<400> SEQUENCE: 57

Gly Tyr Thr Phe Thr Ser Tyr
1               5

<210> SEQ ID NO 58
<211> LENGTH: 6
<212> TYPE: PRT
<213> ORGANISM: Artificial Sequence
<220> FEATURE:
<223> OTHER INFORMATION: 2D1 heavy chain CDR2

<400> SEQUENCE: 58

Asp Pro Asn Ser Gly Gly
1               5

<210> SEQ ID NO 59
<211> LENGTH: 6
<212> TYPE: PRT
<213> ORGANISM: Artificial Sequence
<220> FEATURE:
<223> OTHER INFORMATION: 2D1 heavy chain CDR3

<400> SEQUENCE: 59

Trp Gly Thr Gly Asp Tyr
1               5

<210> SEQ ID NO 60
<211> LENGTH: 115
<212> TYPE: PRT
<213> ORGANISM: Artificial Sequence
<220> FEATURE:
<223> OTHER INFORMATION: 2D1 Heavy chain variable region

<400> SEQUENCE: 60

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Arg Gly Leu Glu Trp Ile
        35                  40                  45

Gly Arg Ile Asp Pro Asn Ser Gly Gly Thr Lys Tyr Asn Glu Lys Phe
    50                  55                  60

Lys Ser Lys Ala Thr Leu Thr Val Asp Lys Pro Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Trp Gly Thr Gly Asp Tyr Trp Gly Gln Gly Thr Thr Leu Thr
            100                 105                 110

Val Ser Ser
        115

<210> SEQ ID NO 61

-continued

```
<211> LENGTH: 15
<212> TYPE: PRT
<213> ORGANISM: Artificial Sequence
<220> FEATURE:
<223> OTHER INFORMATION: 2D1 light chain CDR1

<400> SEQUENCE: 61

Arg Ala Ser Lys Ser Val Ser Thr Ser Gly Tyr Ser Tyr Met His
1               5                   10                  15

<210> SEQ ID NO 62
<211> LENGTH: 7
<212> TYPE: PRT
<213> ORGANISM: Artificial Sequence
<220> FEATURE:
<223> OTHER INFORMATION: 2D1 light chain CDR2

<400> SEQUENCE: 62

Leu Ala Ser Asn Leu Glu Ser
1               5

<210> SEQ ID NO 63
<211> LENGTH: 9
<212> TYPE: PRT
<213> ORGANISM: Artificial Sequence
<220> FEATURE:
<223> OTHER INFORMATION: 2D1 light chain CDR3

<400> SEQUENCE: 63

Gln His Ser Arg Glu Leu Pro Phe Thr
1               5

<210> SEQ ID NO 64
<211> LENGTH: 113
<212> TYPE: PRT
<213> ORGANISM: Artificial Sequence
<220> FEATURE:
<223> OTHER INFORMATION: 2D1 light chain variable region

<400> SEQUENCE: 64

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
                20                  25                  30

Gly Tyr Ser Tyr Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Phe Thr Phe Gly Ser Gly Thr Lys Leu Glu Ile Lys Arg
            100                 105                 110

Ala

<210> SEQ ID NO 65
<211> LENGTH: 7
<212> TYPE: PRT
<213> ORGANISM: Artificial Sequence
<220> FEATURE:
<223> OTHER INFORMATION: 4A1 heavy chain CDR1

<400> SEQUENCE: 65
```

```
Gly Tyr Thr Phe Thr Ser Tyr
1               5
```

<210> SEQ ID NO 66
<211> LENGTH: 6
<212> TYPE: PRT
<213> ORGANISM: Artificial Sequence
<220> FEATURE:
<223> OTHER INFORMATION: 4A1 heavy chain CDR2

<400> SEQUENCE: 66

```
Tyr Pro Arg Ser Gly Asn
1               5
```

<210> SEQ ID NO 67
<211> LENGTH: 8
<212> TYPE: PRT
<213> ORGANISM: Artificial Sequence
<220> FEATURE:
<223> OTHER INFORMATION: 4A1 heavy chain CDR3

<400> SEQUENCE: 67

```
Pro Tyr Glu Gly Tyr Phe Asp Tyr
1               5
```

<210> SEQ ID NO 68
<211> LENGTH: 117
<212> TYPE: PRT
<213> ORGANISM: Artificial Sequence
<220> FEATURE:
<223> OTHER INFORMATION: 4A1 Heavy chain variable region

<400> SEQUENCE: 68

```
Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Gly Ile Ser Trp Val Asn Gln Arg Thr Gly Gln Gly Leu Glu Trp Ile
        35                  40                  45

Gly Glu Ile Tyr Pro Arg Ser Gly Asn Thr Tyr Phe Asn Glu Lys Phe
    50                  55                  60

Gln Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Phe Phe Cys
                85                  90                  95

Ala Arg Pro Tyr Glu Gly Tyr Phe Asp Tyr Trp Gly Gln Gly Thr Thr
            100                 105                 110

Leu Thr Val Ser Ser
        115
```

<210> SEQ ID NO 69
<211> LENGTH: 15
<212> TYPE: PRT
<213> ORGANISM: Artificial Sequence
<220> FEATURE:
<223> OTHER INFORMATION: 4A1 light chain CDR1

<400> SEQUENCE: 69

```
Arg Ala Ser Lys Ser Val Ser Thr Ser Gly Tyr Ser Tyr Met His
1               5                   10                  15
```

<210> SEQ ID NO 70

```
<211> LENGTH: 7
<212> TYPE: PRT
<213> ORGANISM: Artificial Sequence
<220> FEATURE:
<223> OTHER INFORMATION: 4A1 light chain CDR2

<400> SEQUENCE: 70

Leu Ala Ser Asn Leu Glu Ser
1               5

<210> SEQ ID NO 71
<211> LENGTH: 9
<212> TYPE: PRT
<213> ORGANISM: Artificial Sequence
<220> FEATURE:
<223> OTHER INFORMATION: 4A1 light chain CDR3

<400> SEQUENCE: 71

Gln His Ser Arg Glu Leu Pro Phe Thr
1               5

<210> SEQ ID NO 72
<211> LENGTH: 113
<212> TYPE: PRT
<213> ORGANISM: Artificial Sequence
<220> FEATURE:
<223> OTHER INFORMATION: 4A1 light chain variable region

<400> SEQUENCE: 72

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
                20                  25                  30

Gly Tyr Ser Tyr Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Phe Thr Phe Gly Ser Gly Thr Lys Leu Ile Lys Arg
            100                 105                 110

Ala

<210> SEQ ID NO 73
<211> LENGTH: 218
<212> TYPE: PRT
<213> ORGANISM: Homo sapiens

<400> SEQUENCE: 73

Met Gly Ser Ala Ala Leu Glu Ile Leu Gly Leu Val Leu Cys Leu Val
1               5                   10                  15

Gly Trp Gly Gly Leu Ile Leu Ala Cys Gly Leu Pro Met Trp Gln Val
                20                  25                  30

Thr Ala Phe Leu Asp His Asn Ile Val Thr Ala Gln Thr Thr Trp Lys
            35                  40                  45

Gly Leu Trp Met Ser Cys Val Val Gln Ser Thr Gly His Met Gln Cys
        50                  55                  60

Lys Val Tyr Asp Ser Val Leu Ala Leu Ser Thr Glu Val Gln Ala Ala
65                  70                  75                  80
```

```
Arg Ala Leu Thr Val Ser Ala Val Leu Leu Ala Phe Val Ala Leu Phe
                85                  90                  95

Val Thr Leu Ala Gly Ala Gln Cys Thr Thr Cys Val Ala Pro Gly Pro
            100                 105                 110

Ala Lys Ala Arg Val Ala Leu Thr Gly Gly Val Leu Tyr Leu Phe Cys
        115                 120                 125

Gly Leu Leu Ala Leu Val Pro Leu Cys Trp Phe Ala Asn Ile Val Val
    130                 135                 140

Arg Glu Phe Tyr Asp Pro Ser Val Pro Val Ser Gln Lys Tyr Glu Leu
145                 150                 155                 160

Gly Ala Ala Leu Tyr Ile Gly Trp Ala Ala Thr Ala Leu Leu Met Val
                165                 170                 175

Gly Gly Cys Leu Leu Cys Cys Gly Ala Trp Val Cys Thr Gly Arg Pro
            180                 185                 190

Asp Leu Ser Phe Pro Val Lys Tyr Ser Ala Pro Arg Arg Pro Thr Ala
        195                 200                 205

Thr Gly Asp Tyr Asp Lys Lys Asn Tyr Val
    210                 215
```

<210> SEQ ID NO 74
<211> LENGTH: 657
<212> TYPE: DNA
<213> ORGANISM: Artificial Sequence
<220> FEATURE:
<223> OTHER INFORMATION: human Claudin 5 coding sequence

<400> SEQUENCE: 74

```
atgggatctg ctgctcttga gatccttgga cttgttctct gccttgttgg atggggagga    60
cttatccttg cttgcggact tcctatgtgg caggttacag cttttcctcga tcacaacatc   120
gtgactgctc agactacttg gaagggactc tggatgtctt gcgtggtgca atctactgga   180
cacatgcagt gcaaggtgta cgattctgtt ctcgctctct ctactgaggt tcaagctgct   240
agggctctta ctgtttctgc tgttctcctc gctttcgtgg ctctcttcgt tactcttgct   300
ggtgctcagt gtactacctg tgttgctcct ggacctgcta aggctagagt tgctcttaca   360
ggtggtgtgc tctaccttt ctgtggactt cttgctcttg tgcctctctg ctggttcgct   420
aacatcgtgg ttagagagtt ctacgatcct tctgtgcctg tgtctcagaa gtacgaactt   480
ggagctgctc tctacattgg atgggctgct actgctctcc ttatggttgg aggatgcctt   540
ctttgttgtg gtgcttgggt gtgcactgga aggcctgatt tgtctttccc agtgaagtac   600
tctgctccta gaaggcctac tgctaccggt gattacgata agaagaacta cgtttga      657
```

<210> SEQ ID NO 75
<211> LENGTH: 189
<212> TYPE: PRT
<213> ORGANISM: Artificial Sequence
<220> FEATURE:
<223> OTHER INFORMATION: human mouse-chimera Claudin 5

<400> SEQUENCE: 75

```
Met Gly Ser Ala Ala Leu Glu Ile Leu Gly Leu Val Leu Cys Leu Val
1               5                   10                  15

Gly Trp Val Gly Leu Ile Leu Ala Cys Gly Leu Pro Met Trp Gln Val
            20                  25                  30

Thr Ala Phe Leu Asp His Asn Ile Val Thr Ala Gln Thr Thr Trp Lys
        35                  40                  45
```

Gly Leu Trp Met Ser Cys Val Val Gln Ser Thr Gly His Met Gln Cys
            50                  55                  60

Lys Val Tyr Asp Ser Val Leu Ala Leu Ser Thr Glu Val Gln Ala Ala
 65                  70                  75                  80

Arg Ala Leu Thr Val Ser Ala Val Leu Ala Leu Val Ala Leu Phe
                85                  90                  95

Val Thr Leu Thr Gly Ala Gln Cys Thr Thr Cys Val Ala Pro Gly Pro
                100                 105                 110

Val Lys Ala Arg Val Ala Leu Thr Gly Gly Ala Leu Tyr Ala Val Cys
            115                 120                 125

Gly Leu Leu Ala Leu Val Pro Leu Cys Trp Phe Ala Asn Ile Val Val
        130                 135                 140

Arg Glu Phe Tyr Asp Pro Ser Val Pro Val Ser Gln Lys Tyr Glu Leu
145                 150                 155                 160

Gly Ala Ala Leu Tyr Ile Gly Trp Ala Ala Thr Ala Leu Leu Met Val
                165                 170                 175

Gly Gly Gly Leu Val Cys Cys Gly Ala Trp Val Cys Thr
                180                 185

<210> SEQ ID NO 76
<211> LENGTH: 570
<212> TYPE: DNA
<213> ORGANISM: Artificial Sequence
<220> FEATURE:
<223> OTHER INFORMATION: human mouse-chimera Claudin 5 coding sequence

<400> SEQUENCE: 76
atgggatctg ctgctcttga gatccttgga cttgttctct gcctcgttgg atgggttgga        60
cttatccttg cttgcggact tcctatgtgg caggttacag cttttcctcga tcacaacatc      120 gtgactgctc agactacttg gaagggactc tggatgtctt gcgtggtgca atctactgga      180
cacatgcagt gcaaggtgta cgattctgtt ctcgctctct ctactgaggt tcaagctgct      240
agggctctta ctgtttctgc tgttctcctt gctctcgtgg ctctcttcgt tactcttact      300
ggtgctcagt gtactacctg tgttgctcct ggacctgtta aggctagagt tgctcttaca      360
ggtggtgctc tctacgctgt tgtgtggactt cttgctcttg tgccactttg ctggttcgct      420
aacatcgtgg tgagagagtt ctacgatcct tctgtgcctg tgtctcagaa gtacgaactt      480
ggagctgcac tctacattgg atgggctgct actgctctcc ttatggttgg aggtggtctt      540
gtttgttgtg gtgcttgggt gtgcacttga                                        570

<210> SEQ ID NO 77
<211> LENGTH: 282
<212> TYPE: PRT
<213> ORGANISM: Artificial Sequence
<220> FEATURE:
<223> OTHER INFORMATION: extracellular domain reversible Claudin 5

<400> SEQUENCE: 77

Met Gly Ser Ala Ala Leu Glu Ile Leu Gly Leu Val Leu Cys Leu Val
 1               5                  10                  15

Gly Trp Gly Gly Leu Ile Leu Ala Cys Gly Leu Pro Met Trp Gln Val
                20                  25                  30

Thr Ala Phe Leu Asp His Asn Ile Val Thr Ala Gln Thr Thr Trp Lys
            35                  40                  45

Gly Leu Trp Met Ser Cys Val Val Gln Ser Thr Gly His Met Gln Cys
         50                  55                  60

Lys Val Tyr Asp Ser Val Leu Ala Leu Ser Thr Glu Val Gln Ala Ala
65                  70                  75                  80

Arg Ala Leu Thr Val Ser Ala Val Leu Leu Ala Phe Trp Gly Gly Leu
                85                  90                  95

Ile Leu Ala Cys Gly Leu Pro Met Trp Gln Val Thr Ala Phe Leu Asp
                100                 105                 110

His Asn Ile Val Thr Ala Gln Thr Thr Trp Lys Gly Leu Trp Met Ser
            115                 120                 125

Cys Val Val Gln Ser Thr Gly His Met Gln Cys Lys Val Tyr Asp Ser
        130                 135                 140

Val Leu Ala Leu Ser Thr Glu Val Gln Ala Ala Arg Ala Leu Thr Val
145                 150                 155                 160

Ser Ala Val Leu Leu Ala Phe Leu Leu Ala Leu Val Pro Leu Cys Trp
                165                 170                 175

Phe Ala Asn Ile Val Val Arg Glu Phe Tyr Asp Pro Ser Val Pro Val
                180                 185                 190

Ser Gln Lys Tyr Glu Leu Gly Ala Ala Leu Tyr Ile Gly Trp Ala Ala
            195                 200                 205

Thr Ala Leu Leu Met Val Gly Leu Leu Ala Leu Val Pro Leu Cys Trp
        210                 215                 220

Phe Ala Asn Ile Val Val Arg Glu Phe Tyr Asp Pro Ser Val Pro Val
225                 230                 235                 240

Ser Gln Lys Tyr Glu Leu Gly Ala Ala Leu Tyr Ile Gly Trp Ala Ala
                245                 250                 255

Thr Ala Leu Leu Met Val Gly Trp Gly Gly Leu Ile Leu Ala Cys Gly
                260                 265                 270

Leu Pro Met Trp Gln Val Thr Ala Phe Leu
            275                 280

<210> SEQ ID NO 78
<211> LENGTH: 849
<212> TYPE: DNA
<213> ORGANISM: Artificial Sequence
<220> FEATURE:
<223> OTHER INFORMATION: extracellular domain reversible Claudin 5
      coding sequence

<400> SEQUENCE: 78
atgggatctg ctgctcttga gatccttgga cttgttctct gccttgttgg atggggagga      60
cttatccttg cttgcggact tcctatgtgg caggttacag ctttcctcga tcacaacatc    120
gtgactgctc agactacttg gaagggactc tggatgtctt gcgtggtgca atctactgga    180
cacatgcagt gcaaggtgta cgattctgtt ctcgctctct ctactgaggt tcaagctgct    240
agggctctta ctgtttctgc tgttcttctc gctttctggg gtggtctgat cctggcctgt    300
ggcctgccaa tgtggcaagt gaccgccttc ctggaccata atatagtcac cgcccagacc    360
acctggaaag gcctgtggat gagctgtgtc gtccagagca caggccatat gcaatgtaag    420
gtttatgaca gcgtgctggc cctgagcaca gaagtgcagg cagcaagagc cctgaccgtg    480
agtgcagtgc tgctggcctt tttgctcgct cttgttccac tctgctggtt cgctaacatt    540
gtggtgagag agttctacga cccatccgtt ccagtgtctc agaagtatga acttggcgct    600
gctctctaca ttggatgggc tgctactgct cttttgatgg tgggattatt ggcactcgtt    660
ccactctgtt ggtttgccaa tattgttgtg cgtgaatttt atgacccatc ggtgccagtg    720
tcgcaaaaat acgagttggg tgctgccttg tatatcggtt gggcagctac agctcttttg    780

```
atggtaggtt ggggtggact tattctcgca tgtggactcc caatgtggca ggttaccgca    840
tttctttga                                                            849
```

<210> SEQ ID NO 79
<211> LENGTH: 211
<212> TYPE: PRT
<213> ORGANISM: Homo sapiens

<400> SEQUENCE: 79

```
Met Ala Asn Ala Gly Leu Gln Leu Leu Gly Phe Ile Leu Ala Phe Leu
1               5                   10                  15

Gly Trp Ile Gly Ala Ile Val Ser Thr Ala Leu Pro Gln Trp Arg Ile
            20                  25                  30

Tyr Ser Tyr Ala Gly Asp Asn Ile Val Thr Ala Gln Ala Met Tyr Glu
        35                  40                  45

Gly Leu Trp Met Ser Cys Val Ser Gln Ser Thr Gly Gln Ile Gln Cys
    50                  55                  60

Lys Val Phe Asp Ser Leu Leu Asn Leu Ser Ser Thr Leu Gln Ala Thr
65                  70                  75                  80

Arg Ala Leu Met Val Val Gly Ile Leu Leu Gly Val Ile Ala Ile Phe
                85                  90                  95

Val Ala Thr Val Gly Met Lys Cys Met Lys Cys Leu Glu Asp Asp Glu
            100                 105                 110

Val Gln Lys Met Arg Met Ala Val Ile Gly Gly Ala Ile Phe Leu Leu
        115                 120                 125

Ala Gly Leu Ala Ile Leu Val Ala Thr Ala Trp Tyr Gly Asn Arg Ile
    130                 135                 140

Val Gln Glu Phe Tyr Asp Pro Met Thr Pro Val Asn Ala Arg Tyr Glu
145                 150                 155                 160

Phe Gly Gln Ala Leu Phe Thr Gly Trp Ala Ala Ala Ser Leu Cys Leu
                165                 170                 175

Leu Gly Gly Ala Leu Leu Cys Cys Ser Cys Pro Arg Lys Thr Thr Ser
            180                 185                 190

Tyr Pro Thr Pro Arg Pro Tyr Pro Lys Pro Ala Pro Ser Ser Gly Lys
        195                 200                 205

Asp Tyr Val
    210
```

<210> SEQ ID NO 80
<211> LENGTH: 230
<212> TYPE: PRT
<213> ORGANISM: Homo sapiens

<400> SEQUENCE: 80

```
Met Ala Ser Leu Gly Leu Gln Leu Val Gly Tyr Ile Leu Gly Leu Leu
1               5                   10                  15

Gly Leu Leu Gly Thr Leu Val Ala Met Leu Leu Pro Ser Trp Lys Thr
            20                  25                  30

Ser Ser Tyr Val Gly Ala Ser Ile Val Thr Ala Val Gly Phe Ser Lys
        35                  40                  45

Gly Leu Trp Met Glu Cys Ala Thr His Ser Thr Gly Ile Thr Gln Cys
    50                  55                  60

Asp Ile Tyr Ser Thr Leu Leu Gly Leu Pro Ala Asp Ile Gln Ala Ala
65                  70                  75                  80

Gln Ala Met Met Val Thr Ser Ser Ala Ile Ser Ser Leu Ala Cys Ile
                85                  90                  95
```

```
Ile Ser Val Val Gly Met Arg Cys Thr Val Phe Cys Gln Glu Ser Arg
            100                 105                 110

Ala Lys Asp Arg Val Ala Val Ala Gly Gly Val Phe Phe Ile Leu Gly
            115                 120                 125

Gly Leu Leu Gly Phe Ile Pro Val Ala Trp Asn Leu His Gly Ile Leu
            130                 135                 140

Arg Asp Phe Tyr Ser Pro Leu Val Pro Asp Ser Met Lys Phe Glu Ile
145                 150                 155                 160

Gly Glu Ala Leu Tyr Leu Gly Ile Ile Ser Ser Leu Phe Ser Leu Ile
                165                 170                 175

Ala Gly Ile Ile Leu Cys Phe Ser Cys Ser Ser Gln Arg Asn Arg Ser
            180                 185                 190

Asn Tyr Tyr Asp Ala Tyr Gln Ala Gln Pro Leu Ala Thr Arg Ser Ser
                195                 200                 205

Pro Arg Pro Gly Gln Pro Pro Lys Val Lys Ser Glu Phe Asn Ser Tyr
210                 215                 220

Ser Leu Thr Gly Tyr Val
225                 230

<210> SEQ ID NO 81
<211> LENGTH: 220
<212> TYPE: PRT
<213> ORGANISM: Homo sapiens

<400> SEQUENCE: 81

Met Ser Met Gly Leu Glu Ile Thr Gly Thr Ala Leu Ala Val Leu Gly
1               5                   10                  15

Trp Leu Gly Thr Ile Val Cys Cys Ala Leu Pro Met Trp Arg Val Ser
            20                  25                  30

Ala Phe Ile Gly Ser Asn Ile Ile Thr Ser Gln Asn Ile Trp Glu Gly
            35                  40                  45

Leu Trp Met Asn Cys Val Val Gln Ser Thr Gly Gln Met Gln Cys Lys
50                  55                  60

Val Tyr Asp Ser Leu Leu Ala Leu Pro Gln Asp Leu Gln Ala Ala Arg
65                  70                  75                  80

Ala Leu Ile Val Val Ala Ile Leu Leu Ala Ala Phe Gly Leu Leu Val
                85                  90                  95

Ala Leu Val Gly Ala Gln Cys Thr Asn Cys Val Gln Asp Asp Thr Ala
            100                 105                 110

Lys Ala Lys Ile Thr Ile Val Ala Gly Val Leu Phe Leu Leu Ala Ala
            115                 120                 125

Leu Leu Thr Leu Val Pro Val Ser Trp Ser Ala Asn Thr Ile Ile Arg
            130                 135                 140

Asp Phe Tyr Asn Pro Val Val Pro Glu Ala Gln Lys Arg Glu Met Gly
145                 150                 155                 160

Ala Gly Leu Tyr Val Gly Trp Ala Ala Ala Leu Gln Leu Leu Gly Gly
                165                 170                 175

Gly Ala Leu Leu Cys Cys Ser Cys Pro Pro Arg Glu Lys Lys Tyr Thr
            180                 185                 190

Ala Thr Lys Val Val Tyr Ser Ala Pro Arg Ser Thr Gly Pro Gly Ala
            195                 200                 205

Ser Leu Gly Thr Gly Tyr Asp Arg Lys Asp Tyr Val
210                 215                 220
```

<210> SEQ ID NO 82
<211> LENGTH: 209
<212> TYPE: PRT
<213> ORGANISM: Homo sapiens

<400> SEQUENCE: 82

Met Ala Ser Met Gly Leu Gln Val Met Gly Ile Ala Leu Ala Val Leu
1               5                   10                  15

Gly Trp Leu Ala Val Met Leu Cys Cys Ala Leu Pro Met Trp Arg Val
            20                  25                  30

Thr Ala Phe Ile Gly Ser Asn Ile Val Thr Ser Gln Thr Ile Trp Glu
        35                  40                  45

Gly Leu Trp Met Asn Cys Val Val Gln Ser Thr Gly Gln Met Gln Cys
    50                  55                  60

Lys Val Tyr Asp Ser Leu Leu Ala Leu Pro Gln Asp Leu Gln Ala Ala
65                  70                  75                  80

Arg Ala Leu Val Ile Ile Ser Ile Ile Val Ala Ala Leu Gly Val Leu
                85                  90                  95

Leu Ser Val Val Gly Gly Lys Cys Thr Asn Cys Leu Glu Asp Glu Ser
            100                 105                 110

Ala Lys Ala Lys Thr Met Ile Val Ala Gly Val Val Phe Leu Leu Ala
        115                 120                 125

Gly Leu Met Val Ile Val Pro Val Ser Trp Thr Ala His Asn Ile Ile
    130                 135                 140

Gln Asp Phe Tyr Asn Pro Leu Val Ala Ser Gly Gln Lys Arg Glu Met
145                 150                 155                 160

Gly Ala Ser Leu Tyr Val Gly Trp Ala Ala Ser Gly Leu Leu Leu Leu
                165                 170                 175

Gly Gly Gly Leu Leu Cys Cys Asn Cys Pro Pro Arg Thr Asp Lys Pro
            180                 185                 190

Tyr Ser Ala Lys Tyr Ser Ala Ala Arg Ser Ala Ala Ala Ser Asn Tyr
        195                 200                 205

Val

<210> SEQ ID NO 83
<211> LENGTH: 220
<212> TYPE: PRT
<213> ORGANISM: Homo sapiens

<400> SEQUENCE: 83

Met Ala Ser Ala Gly Met Gln Ile Leu Gly Val Val Leu Thr Leu Leu
1               5                   10                  15

Gly Trp Val Asn Gly Leu Val Ser Cys Ala Leu Pro Met Trp Lys Val
            20                  25                  30

Thr Ala Phe Ile Gly Asn Ser Ile Val Val Ala Gln Val Val Trp Glu
        35                  40                  45

Gly Leu Trp Met Ser Cys Val Val Gln Ser Thr Gly Gln Met Gln Cys
    50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Val Ala Leu Phe Gly Leu Leu
                85                  90                  95

Val Tyr Leu Ala Gly Ala Lys Cys Thr Thr Cys Val Glu Glu Lys Asp
            100                 105                 110

Ser Lys Ala Arg Leu Val Leu Thr Ser Gly Ile Val Phe Val Ile Ser
        115                 120                 125

Gly Val Leu Thr Leu Ile Pro Val Cys Trp Thr Ala His Ala Ile Ile
            130                 135                 140

Arg Asp Phe Tyr Asn Pro Leu Val Ala Glu Ala Gln Lys Arg Glu Leu
145                 150                 155                 160

Gly Ala Ser Leu Tyr Leu Gly Trp Ala Ala Ser Gly Leu Leu Leu Leu
                165                 170                 175

Gly Gly Gly Leu Leu Cys Cys Thr Cys Pro Ser Gly Ser Gln Gly
            180                 185                 190

Pro Ser His Tyr Met Ala Arg Tyr Ser Thr Ser Ala Pro Ala Ile Ser
                195                 200                 205

Arg Gly Pro Ser Glu Tyr Pro Thr Lys Asn Tyr Val
            210                 215                 220

<210> SEQ ID NO 84
<211> LENGTH: 211
<212> TYPE: PRT
<213> ORGANISM: Homo sapiens

<400> SEQUENCE: 84

Met Ala Asn Ser Gly Leu Gln Leu Leu Gly Phe Ser Met Ala Leu Leu
1               5                   10                  15

Gly Trp Val Gly Leu Val Ala Cys Thr Ala Ile Pro Gln Trp Gln Met
            20                  25                  30

Ser Ser Tyr Ala Gly Asp Asn Ile Ile Thr Ala Gln Ala Met Tyr Lys
                35                  40                  45

Gly Leu Trp Met Asp Cys Val Thr Gln Ser Thr Gly Met Met Ser Cys
50                  55                  60

Lys Met Tyr Asp Ser Val Leu Ala Leu Ser Ala Ala Leu Gln Ala Thr
65                  70                  75                  80

Arg Ala Leu Met Val Val Ser Leu Val Leu Gly Phe Leu Ala Met Phe
                85                  90                  95

Val Ala Thr Met Gly Met Lys Cys Thr Arg Cys Gly Gly Asp Asp Lys
            100                 105                 110

Val Lys Lys Ala Arg Ile Ala Met Gly Gly Gly Ile Ile Phe Ile Val
        115                 120                 125

Ala Gly Leu Ala Ala Leu Val Ala Cys Ser Trp Tyr Gly His Gln Ile
130                 135                 140

Val Thr Asp Phe Tyr Asn Pro Leu Ile Pro Thr Asn Ile Lys Tyr Glu
145                 150                 155                 160

Phe Gly Pro Ala Ile Phe Ile Gly Trp Ala Gly Ser Ala Leu Val Ile
                165                 170                 175

Leu Gly Gly Ala Leu Leu Ser Cys Ser Cys Pro Gly Asn Glu Ser Lys
            180                 185                 190

Ala Gly Tyr Arg Val Pro Arg Ser Tyr Pro Lys Ser Asn Ser Ser Lys
        195                 200                 205

Glu Tyr Val
    210

<210> SEQ ID NO 85
<211> LENGTH: 217
<212> TYPE: PRT
<213> ORGANISM: Homo sapiens

<400> SEQUENCE: 85

Met Ala Ser Thr Gly Leu Glu Leu Leu Gly Met Thr Leu Ala Val Leu
1               5                   10                  15

Gly Trp Leu Gly Thr Leu Val Ser Cys Ala Leu Pro Leu Trp Lys Val
            20                  25                  30

Thr Ala Phe Ile Gly Asn Ser Ile Val Val Ala Gln Val Val Trp Glu
        35                  40                  45

Gly Leu Trp Met Ser Cys Val Val Gln Ser Thr Gly Gln Met Gln Cys
50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Leu Ala Leu Gly Leu Leu
                85                  90                  95

Val Ala Ile Thr Gly Ala Gln Cys Thr Thr Cys Val Glu Asp Glu Gly
            100                 105                 110

Ala Lys Ala Arg Ile Val Leu Thr Ala Gly Val Ile Leu Leu Leu Ala
        115                 120                 125

Gly Ile Leu Val Leu Ile Pro Val Cys Trp Thr Ala His Ala Ile Ile
130                 135                 140

Gln Asp Phe Tyr Asn Pro Leu Val Ala Glu Ala Leu Lys Arg Glu Leu
145                 150                 155                 160

Gly Ala Ser Leu Tyr Leu Gly Trp Ala Ala Ala Leu Leu Met Leu
                165                 170                 175

Gly Gly Gly Leu Leu Cys Cys Thr Cys Pro Pro Gln Val Glu Arg
            180                 185                 190

Pro Arg Gly Pro Arg Leu Gly Tyr Ser Ile Pro Ser Arg Ser Gly Ala
        195                 200                 205

Ser Gly Leu Asp Lys Arg Asp Tyr Val
210                 215

<210> SEQ ID NO 86
<211> LENGTH: 211
<212> TYPE: PRT
<213> ORGANISM: Mus musculus

<400> SEQUENCE: 86

Met Ala Asn Ala Gly Leu Gln Leu Leu Gly Phe Ile Leu Ala Ser Leu
1               5                   10                  15

Gly Trp Ile Gly Ser Ile Val Ser Thr Ala Leu Pro Gln Trp Lys Ile
            20                  25                  30

Tyr Ser Tyr Ala Gly Asp Asn Ile Val Thr Ala Gln Ala Ile Tyr Glu
        35                  40                  45

Gly Leu Trp Met Ser Cys Val Ser Gln Ser Thr Gly Gln Ile Gln Cys
50                  55                  60

Lys Val Phe Asp Ser Leu Leu Asn Leu Asn Ser Thr Leu Gln Ala Thr
65                  70                  75                  80

Arg Ala Leu Met Val Ile Gly Ile Leu Leu Gly Leu Ile Ala Ile Phe
                85                  90                  95

Val Ser Thr Ile Gly Met Lys Cys Met Arg Cys Leu Glu Asp Asp Glu
            100                 105                 110

Val Gln Lys Met Trp Met Ala Val Ile Gly Gly Ile Ile Phe Leu Ile
        115                 120                 125

Ser Gly Leu Ala Thr Leu Val Ala Thr Ala Trp Tyr Gly Asn Arg Ile
130                 135                 140

Val Gln Glu Phe Tyr Asp Pro Leu Thr Pro Ile Asn Ala Arg Tyr Glu
145                 150                 155                 160

Phe Gly Gln Ala Leu Phe Thr Gly Trp Ala Ala Ala Ser Leu Cys Leu 165                 170                 175

Leu Gly Gly Val Leu Leu Ser Cys Ser Cys Pro Arg Lys Thr Thr Ser
            180                 185                 190

Tyr Pro Thr Pro Arg Pro Tyr Pro Lys Pro Thr Pro Ser Ser Gly Lys
        195                 200                 205

Asp Tyr Val
    210

<210> SEQ ID NO 87
<211> LENGTH: 230
<212> TYPE: PRT
<213> ORGANISM: Mus musculus

<400> SEQUENCE: 87

Met Ala Ser Leu Gly Val Gln Leu Val Gly Tyr Ile Leu Gly Leu Leu
1               5                   10                  15

Gly Leu Leu Gly Thr Ser Ile Ala Met Leu Leu Pro Asn Trp Arg Thr
            20                  25                  30

Ser Ser Tyr Val Gly Ala Ser Ile Val Thr Ala Val Gly Phe Ser Lys
        35                  40                  45

Gly Leu Trp Met Glu Cys Ala Thr His Ser Thr Gly Ile Thr Gln Cys
    50                  55                  60

Asp Ile Tyr Ser Thr Leu Leu Gly Leu Pro Ala Asp Ile Gln Ala Ala
65                  70                  75                  80

Gln Ala Met Met Val Thr Ser Ser Ala Met Ser Ser Leu Ala Cys Ile
                85                  90                  95

Ile Ser Val Val Gly Met Arg Cys Thr Val Phe Cys Gln Asp Ser Arg
            100                 105                 110

Ala Lys Asp Arg Val Ala Val Val Gly Gly Val Phe Phe Ile Leu Gly
        115                 120                 125

Gly Ile Leu Gly Phe Ile Pro Val Ala Trp Asn Leu His Gly Ile Leu
    130                 135                 140

Arg Asp Phe Tyr Ser Pro Leu Val Pro Asp Ser Met Lys Phe Glu Ile
145                 150                 155                 160

Gly Glu Ala Leu Tyr Leu Gly Ile Ile Ser Ala Leu Phe Ser Leu Val
                165                 170                 175

Ala Gly Val Ile Leu Cys Phe Ser Cys Ser Pro Gln Gly Asn Arg Thr
            180                 185                 190

Asn Tyr Tyr Asp Gly Tyr Gln Ala Gln Pro Leu Ala Thr Arg Ser Ser
        195                 200                 205

Pro Arg Ser Ala Gln Gln Pro Lys Ala Lys Ser Glu Phe Asn Ser Tyr
    210                 215                 220

Ser Leu Thr Gly Tyr Val
225                 230

<210> SEQ ID NO 88
<211> LENGTH: 219
<212> TYPE: PRT
<213> ORGANISM: Mus musculus

<400> SEQUENCE: 88

Met Ser Met Gly Leu Glu Ile Thr Gly Thr Ser Leu Ala Val Leu Gly
1               5                   10                  15

Trp Leu Cys Thr Ile Val Cys Cys Ala Leu Pro Met Trp Arg Val Ser
            20                  25                  30

Ala Phe Ile Gly Ser Ser Ile Ile Thr Ala Gln Ile Thr Trp Glu Gly

```
                35                  40                  45
Leu Trp Met Asn Cys Val Val Gln Ser Thr Gly Gln Met Gln Cys Lys
 50                  55                  60

Met Tyr Asp Ser Leu Leu Ala Leu Pro Gln Asp Leu Gln Ala Ala Arg
 65                  70                  75                  80

Ala Leu Ile Val Val Ser Ile Leu Leu Ala Ala Phe Gly Leu Leu Val
                 85                  90                  95

Ala Leu Val Gly Ala Gln Cys Thr Asn Cys Val Gln Asp Glu Thr Ala
                100                 105                 110

Lys Ala Lys Ile Thr Ile Val Ala Gly Val Leu Phe Leu Leu Ala Ala
                115                 120                 125

Leu Leu Thr Leu Val Pro Val Ser Trp Ser Ala Asn Thr Ile Ile Arg
130                 135                 140

Asp Phe Tyr Asn Pro Leu Val Pro Glu Ala Gln Lys Arg Glu Met Gly
145                 150                 155                 160

Ala Gly Leu Tyr Val Gly Trp Ala Ala Ala Leu Gln Leu Leu Gly
                165                 170                 175

Gly Ala Leu Leu Cys Cys Ser Cys Pro Pro Arg Asp Lys Tyr Ala Pro
                180                 185                 190

Thr Lys Ile Leu Tyr Ser Ala Pro Arg Ser Thr Gly Pro Gly Thr Gly
                195                 200                 205

Thr Gly Thr Ala Tyr Asp Arg Lys Asp Tyr Val
210                 215

<210> SEQ ID NO 89
<211> LENGTH: 210
<212> TYPE: PRT
<213> ORGANISM: Mus musculus

<400> SEQUENCE: 89

Met Ala Ser Met Gly Leu Gln Val Leu Gly Ile Ser Leu Ala Val Leu
 1               5                  10                  15

Gly Trp Leu Gly Ile Ile Leu Ser Cys Ala Leu Pro Met Trp Arg Val
                 20                  25                  30

Thr Ala Phe Ile Gly Ser Asn Ile Val Thr Ala Gln Thr Ser Trp Glu
                 35                  40                  45

Gly Leu Trp Met Asn Cys Val Val Gln Ser Thr Gly Gln Met Gln Cys
 50                  55                  60

Lys Met Tyr Asp Ser Met Leu Ala Leu Pro Gln Asp Leu Gln Ala Ala
 65                  70                  75                  80

Arg Ala Leu Met Val Ile Ser Ile Ile Val Gly Ala Leu Gly Met Leu
                 85                  90                  95

Leu Ser Val Val Gly Gly Lys Cys Thr Asn Cys Met Glu Asp Glu Thr
                100                 105                 110

Val Lys Ala Lys Ile Met Ile Thr Ala Gly Ala Val Phe Ile Val Ala
                115                 120                 125

Ser Met Leu Ile Met Val Pro Val Ser Trp Thr Ala His Asn Val Ile
130                 135                 140

Arg Asp Phe Tyr Asn Pro Met Val Ala Ser Gly Gln Lys Arg Glu Met
145                 150                 155                 160

Gly Ala Ser Leu Tyr Val Gly Trp Ala Ala Ser Gly Leu Leu Leu Leu
                165                 170                 175

Gly Gly Gly Leu Leu Cys Cys Ser Cys Pro Pro Arg Ser Asn Asp Lys
                180                 185                 190
```

Pro Tyr Ser Ala Lys Tyr Ser Ala Ala Arg Ser Val Pro Ala Ser Asn
                195                 200                 205

Tyr Val
    210

<210> SEQ ID NO 90
<211> LENGTH: 218
<212> TYPE: PRT
<213> ORGANISM: Mus musculus

<400> SEQUENCE: 90

Met Gly Ser Ala Ala Leu Glu Ile Leu Gly Leu Val Leu Cys Leu Val
1               5                   10                  15

Gly Trp Val Gly Leu Ile Leu Ala Cys Gly Leu Pro Met Trp Gln Val
            20                  25                  30

Thr Ala Phe Leu Asp His Asn Ile Val Thr Ala Gln Thr Thr Trp Lys
        35                  40                  45

Gly Leu Trp Met Ser Cys Val Val Gln Ser Thr Gly His Met Gln Cys
    50                  55                  60

Lys Val Tyr Glu Ser Val Leu Ala Leu Ser Ala Glu Val Gln Ala Ala
65                  70                  75                  80

Arg Ala Leu Thr Val Gly Ala Val Leu Leu Ala Leu Val Ala Leu Phe
                85                  90                  95

Val Thr Leu Thr Gly Ala Gln Cys Thr Thr Cys Val Ala Pro Gly Pro
            100                 105                 110

Val Lys Ala Arg Val Ala Leu Thr Gly Gly Ala Leu Tyr Ala Val Cys
        115                 120                 125

Gly Leu Leu Ala Leu Val Pro Leu Cys Trp Phe Ala Asn Ile Val Val
    130                 135                 140

Arg Glu Phe Tyr Asp Pro Thr Val Pro Val Ser Gln Lys Tyr Glu Leu
145                 150                 155                 160

Gly Ala Ala Leu Tyr Ile Gly Trp Ala Ala Ser Ala Leu Leu Met Cys
                165                 170                 175

Gly Gly Gly Leu Val Cys Cys Gly Ala Trp Val Cys Thr Gly Arg Pro
            180                 185                 190

Glu Phe Ser Phe Pro Val Lys Tyr Ser Ala Pro Arg Arg Pro Thr Ala
        195                 200                 205

Asn Gly Asp Tyr Asp Lys Lys Asn Tyr Val
    210                 215

<210> SEQ ID NO 91
<211> LENGTH: 218
<212> TYPE: PRT
<213> ORGANISM: Rattus norvegicus

<400> SEQUENCE: 91

Met Gly Ser Ala Ala Leu Glu Ile Leu Gly Leu Val Leu Cys Leu Val
1               5                   10                  15

Gly Trp Val Gly Leu Ile Leu Ala Cys Gly Leu Pro Met Trp Gln Val
            20                  25                  30

Thr Ala Phe Leu Asp His Asn Ile Val Thr Ala Gln Thr Thr Trp Lys
        35                  40                  45

Gly Leu Trp Met Ser Cys Val Val Gln Ser Thr Gly His Met Gln Cys
    50                  55                  60

Lys Val Tyr Glu Ser Val Leu Ala Leu Ser Ala Glu Val Gln Ala Ala
65                  70                  75                  80

```
Arg Ala Leu Thr Val Gly Ala Val Leu Leu Ala Leu Val Ala Leu Phe
                85                  90                  95
Val Thr Leu Thr Gly Ala Gln Cys Thr Thr Cys Val Ala Pro Gly Pro
            100                 105                 110
Val Lys Ala Arg Val Ala Leu Thr Gly Gly Ala Leu Tyr Ala Leu Cys
            115                 120                 125
Gly Leu Leu Ala Leu Val Pro Leu Cys Trp Phe Ala Asn Ile Val Val
        130                 135                 140
Arg Glu Phe Tyr Asp Pro Thr Val Pro Val Ser Gln Lys Tyr Glu Leu
145                 150                 155                 160
Gly Ala Ala Leu Tyr Ile Gly Trp Ala Ala Ser Ala Leu Leu Met Cys
                165                 170                 175
Gly Gly Gly Leu Val Cys Cys Gly Ala Trp Val Cys Thr Gly Arg Pro
            180                 185                 190
Glu Phe Ser Phe Pro Val Lys Tyr Ser Ala Pro Arg Thr Thr Ala
            195                 200                 205
Asn Gly Asp Tyr Asp Lys Lys Asn Tyr Val
        210                 215
```

<210> SEQ ID NO 92
<211> LENGTH: 218
<212> TYPE: PRT
<213> ORGANISM: Macaca fascicularis

<400> SEQUENCE: 92

```
Met Gly Ser Ala Ala Leu Glu Ile Leu Gly Leu Val Leu Cys Leu Val
1               5                   10                  15
Gly Trp Gly Gly Leu Ile Leu Ala Cys Gly Leu Pro Met Trp Gln Val
            20                  25                  30
Thr Ala Phe Leu Asp His Asn Ile Val Thr Ala Gln Thr Thr Trp Lys
        35                  40                  45
Gly Leu Trp Met Ser Cys Val Val Gln Ser Thr Gly His Met Gln Cys
    50                  55                  60
Lys Val Tyr Asp Ser Val Leu Ala Leu Ser Thr Glu Val Gln Ala Ala
65                  70                  75                  80
Arg Ala Leu Thr Val Gly Ala Val Leu Leu Ala Phe Val Ala Leu Phe
                85                  90                  95
Val Thr Leu Ala Gly Ala Gln Cys Thr Thr Cys Val Ala Pro Gly Pro
            100                 105                 110
Ala Lys Ala Arg Val Ala Leu Thr Gly Gly Val Leu Tyr Leu Leu Cys
            115                 120                 125
Gly Leu Leu Ala Leu Val Pro Leu Cys Trp Phe Ala Asn Ile Val Val
        130                 135                 140
Arg Glu Phe Tyr Asp Pro Ser Val Pro Val Ser Gln Lys Tyr Glu Leu
145                 150                 155                 160
Gly Ala Ala Leu Tyr Ile Gly Trp Ala Ala Thr Ala Leu Leu Met Val
                165                 170                 175
Gly Gly Gly Leu Leu Cys Cys Gly Ala Trp Val Cys Thr Ser Arg Pro
            180                 185                 190
Asp Leu Ser Phe Pro Val Lys Tyr Ser Ala Pro Arg Arg Pro Thr Ala
            195                 200                 205
Thr Gly Asp Tyr Asp Lys Lys Asn Tyr Val
        210                 215
```

<210> SEQ ID NO 93

<211> LENGTH: 218
<212> TYPE: PRT
<213> ORGANISM: Artificial Sequence
<220> FEATURE:
<223> OTHER INFORMATION: chimera claudin 1-1-5

<400> SEQUENCE: 93

Met Gly Ser Ala Ala Leu Glu Ile Leu Gly Leu Val Leu Cys Leu Val
1               5                   10                  15

Gly Trp Gly Gly Leu Ile Leu Ala Cys Ala Leu Pro Gln Trp Arg Ile
            20                  25                  30

Tyr Ser Tyr Ala Gly Asp Asn Ile Val Thr Ala Gln Ala Met Tyr Glu
        35                  40                  45

Gly Leu Trp Met Ser Cys Val Ser Gln Ser Thr Gly Gln Ile Gln Cys
    50                  55                  60

Lys Val Phe Asp Ser Leu Leu Asn Leu Ser Ser Thr Val Gln Ala Ala
65                  70                  75                  80

Arg Ala Leu Thr Val Ser Ala Val Leu Leu Ala Phe Val Ala Leu Phe
                85                  90                  95

Val Thr Leu Ala Gly Ala Gln Cys Thr Thr Cys Val Ala Pro Gly Pro
            100                 105                 110

Ala Lys Ala Arg Val Ala Leu Thr Gly Gly Val Leu Tyr Leu Phe Cys
        115                 120                 125

Gly Leu Leu Ala Leu Val Pro Leu Cys Trp Phe Ala Asn Ile Val Val
    130                 135                 140

Arg Glu Phe Tyr Asp Pro Ser Val Pro Val Ser Gln Lys Tyr Glu Leu
145                 150                 155                 160

Gly Ala Ala Leu Tyr Ile Gly Trp Ala Ala Thr Ala Leu Leu Met Val
                165                 170                 175

Gly Gly Cys Leu Leu Cys Cys Gly Ala Trp Val Cys Thr Gly Arg Pro
            180                 185                 190

Asp Leu Ser Phe Pro Val Lys Tyr Ser Ala Pro Arg Arg Pro Thr Ala
        195                 200                 205

Thr Gly Asp Tyr Asp Lys Lys Asn Tyr Val
    210                 215

<210> SEQ ID NO 94
<211> LENGTH: 218
<212> TYPE: PRT
<213> ORGANISM: Artificial Sequence
<220> FEATURE:
<223> OTHER INFORMATION: chimera claudin 1-5-5

<400> SEQUENCE: 94

Met Gly Ser Ala Ala Leu Glu Ile Leu Gly Leu Val Leu Cys Leu Val
1               5                   10                  15

Gly Trp Gly Gly Leu Ile Leu Ala Cys Ala Leu Pro Gln Trp Arg Ile
            20                  25                  30

Tyr Ser Tyr Ala Gly Asp Asn Ile Val Thr Ala Gln Ala Met Tyr Glu
        35                  40                  45

Gly Leu Trp Met Ser Cys Val Val Gln Ser Thr Gly His Met Gln Cys
    50                  55                  60

Lys Val Tyr Asp Ser Val Leu Ala Leu Ser Thr Glu Val Gln Ala Ala
65                  70                  75                  80

Arg Ala Leu Thr Val Ser Ala Val Leu Leu Ala Phe Val Ala Leu Phe
                85                  90                  95

Val Thr Leu Ala Gly Ala Gln Cys Thr Thr Cys Val Ala Pro Gly Pro

```
            100                 105                 110
Ala Lys Ala Arg Val Ala Leu Thr Gly Gly Val Leu Tyr Leu Phe Cys
            115                 120                 125

Gly Leu Leu Ala Leu Val Pro Leu Cys Trp Phe Ala Asn Ile Val Val
            130                 135             140

Arg Glu Phe Tyr Asp Pro Ser Val Pro Val Ser Gln Lys Tyr Glu Leu
145                 150                 155                 160

Gly Ala Ala Leu Tyr Ile Gly Trp Ala Ala Thr Ala Leu Leu Met Val
                165                 170                 175

Gly Gly Cys Leu Leu Cys Cys Gly Ala Trp Val Cys Thr Gly Arg Pro
            180                 185                 190

Asp Leu Ser Phe Pro Val Lys Tyr Ser Ala Pro Arg Arg Pro Thr Ala
            195                 200                 205

Thr Gly Asp Tyr Asp Lys Lys Asn Tyr Val
            210                 215
```

<210> SEQ ID NO 95  
<211> LENGTH: 218  
<212> TYPE: PRT  
<213> ORGANISM: Artificial Sequence  
<220> FEATURE:  
<223> OTHER INFORMATION: chimera claudin 5-1-5

<400> SEQUENCE: 95

```
Met Gly Ser Ala Ala Leu Glu Ile Leu Gly Leu Val Leu Cys Leu Val
1               5                   10                  15

Gly Trp Gly Gly Leu Ile Leu Ala Cys Gly Leu Pro Met Trp Gln Val
            20                  25                  30

Thr Ala Phe Leu Asp His Asn Ile Val Thr Ala Gln Thr Thr Trp Lys
            35                  40                  45

Gly Leu Trp Met Ser Cys Val Ser Gln Ser Thr Gly Gln Ile Gln Cys
        50                  55                  60

Lys Val Phe Asp Ser Leu Leu Asn Leu Ser Ser Thr Val Gln Ala Ala
65                  70                  75                  80

Arg Ala Leu Thr Val Ser Ala Val Leu Leu Ala Phe Val Ala Leu Phe
                85                  90                  95

Val Thr Leu Ala Gly Ala Gln Cys Thr Thr Cys Val Ala Pro Gly Pro
            100                 105                 110

Ala Lys Ala Arg Val Ala Leu Thr Gly Gly Val Leu Tyr Leu Phe Cys
            115                 120                 125

Gly Leu Leu Ala Leu Val Pro Leu Cys Trp Phe Ala Asn Ile Val Val
            130                 135             140

Arg Glu Phe Tyr Asp Pro Ser Val Pro Val Ser Gln Lys Tyr Glu Leu
145                 150                 155                 160

Gly Ala Ala Leu Tyr Ile Gly Trp Ala Ala Thr Ala Leu Leu Met Val
                165                 170                 175

Gly Gly Cys Leu Leu Cys Cys Gly Ala Trp Val Cys Thr Gly Arg Pro
            180                 185                 190

Asp Leu Ser Phe Pro Val Lys Tyr Ser Ala Pro Arg Arg Pro Thr Ala
            195                 200                 205

Thr Gly Asp Tyr Asp Lys Lys Asn Tyr Val
            210                 215
```

<210> SEQ ID NO 96  
<211> LENGTH: 218  
<212> TYPE: PRT

<213> ORGANISM: Artificial Sequence
<220> FEATURE:
<223> OTHER INFORMATION: chimera claudin 5-5-1

<400> SEQUENCE: 96

Met Gly Ser Ala Ala Leu Glu Ile Leu Gly Leu Val Leu Cys Leu Val
1               5                   10                  15

Gly Trp Gly Gly Leu Ile Leu Ala Cys Gly Leu Pro Met Trp Gln Val
            20                  25                  30

Thr Ala Phe Leu Asp His Asn Ile Val Thr Ala Gln Thr Thr Trp Lys
        35                  40                  45

Gly Leu Trp Met Ser Cys Val Val Gln Ser Thr Gly His Met Gln Cys
    50                  55                  60

Lys Val Tyr Asp Ser Val Leu Ala Leu Ser Thr Glu Val Gln Ala Ala
65                  70                  75                  80

Arg Ala Leu Thr Val Ser Ala Val Leu Leu Ala Phe Val Ala Leu Phe
                85                  90                  95

Val Thr Leu Ala Gly Ala Gln Cys Thr Thr Cys Val Ala Pro Gly Pro
            100                 105                 110

Ala Lys Ala Arg Val Ala Leu Thr Gly Gly Val Leu Tyr Leu Phe Cys
        115                 120                 125

Gly Leu Leu Ala Leu Val Pro Leu Cys Trp Phe Ala Asn Ile Val Val
    130                 135                 140

Arg Glu Phe Tyr Asp Pro Met Thr Pro Val Asn Ala Arg Tyr Glu Phe
145                 150                 155                 160

Gly Gln Ala Leu Tyr Ile Gly Trp Ala Ala Thr Ala Leu Leu Met Val
                165                 170                 175

Gly Gly Cys Leu Leu Cys Cys Gly Ala Trp Val Cys Thr Gly Arg Pro
            180                 185                 190

Asp Leu Ser Phe Pro Val Lys Tyr Ser Ala Pro Arg Arg Pro Thr Ala
        195                 200                 205

Thr Gly Asp Tyr Asp Lys Lys Asn Tyr Val
    210                 215

<210> SEQ ID NO 97
<211> LENGTH: 218
<212> TYPE: PRT
<213> ORGANISM: Artificial Sequence
<220> FEATURE:
<223> OTHER INFORMATION: point mutated claudin 5 D68E

<400> SEQUENCE: 97

Met Gly Ser Ala Ala Leu Glu Ile Leu Gly Leu Val Leu Cys Leu Val
1               5                   10                  15

Gly Trp Gly Gly Leu Ile Leu Ala Cys Gly Leu Pro Met Trp Gln Val
            20                  25                  30

Thr Ala Phe Leu Asp His Asn Ile Val Thr Ala Gln Thr Thr Trp Lys
        35                  40                  45

Gly Leu Trp Met Ser Cys Val Val Gln Ser Thr Gly His Met Gln Cys
    50                  55                  60

Lys Val Tyr Glu Ser Val Leu Ala Leu Ser Thr Glu Val Gln Ala Ala
65                  70                  75                  80

Arg Ala Leu Thr Val Ser Ala Val Leu Leu Ala Phe Val Ala Leu Phe
                85                  90                  95

Val Thr Leu Ala Gly Ala Gln Cys Thr Thr Cys Val Ala Pro Gly Pro
            100                 105                 110

```
Ala Lys Ala Arg Val Ala Leu Thr Gly Gly Val Leu Tyr Leu Phe Cys
            115                 120                 125
Gly Leu Leu Ala Leu Val Pro Leu Cys Trp Phe Ala Asn Ile Val Val
            130                 135                 140
Arg Glu Phe Tyr Asp Pro Ser Val Pro Val Ser Gln Lys Tyr Glu Leu
145                 150                 155                 160
Gly Ala Ala Leu Tyr Ile Gly Trp Ala Ala Thr Ala Leu Leu Met Val
                165                 170                 175
Gly Gly Cys Leu Leu Cys Cys Gly Ala Trp Val Cys Thr Gly Arg Pro
            180                 185                 190
Asp Leu Ser Phe Pro Val Lys Tyr Ser Ala Pro Arg Arg Pro Thr Ala
            195                 200                 205
Thr Gly Asp Tyr Asp Lys Lys Asn Tyr Val
            210                 215

<210> SEQ ID NO 98
<211> LENGTH: 218
<212> TYPE: PRT
<213> ORGANISM: Artificial Sequence
<220> FEATURE:
<223> OTHER INFORMATION: point mutated claudin 5 T75A

<400> SEQUENCE: 98

Met Gly Ser Ala Ala Leu Glu Ile Leu Gly Leu Val Leu Cys Leu Val
1               5                   10                  15
Gly Trp Gly Gly Leu Ile Leu Ala Cys Gly Leu Pro Met Trp Gln Val
            20                  25                  30
Thr Ala Phe Leu Asp His Asn Ile Val Thr Ala Gln Thr Thr Trp Lys
        35                  40                  45
Gly Leu Trp Met Ser Cys Val Val Gln Ser Thr Gly His Met Gln Cys
    50                  55                  60
Lys Val Tyr Asp Ser Val Leu Ala Leu Ser Ala Glu Val Gln Ala Ala
65                  70                  75                  80
Arg Ala Leu Thr Val Ser Ala Val Leu Leu Ala Phe Val Ala Leu Phe
                85                  90                  95
Val Thr Leu Ala Gly Ala Gln Cys Thr Thr Cys Val Ala Pro Gly Pro
            100                 105                 110
Ala Lys Ala Arg Val Ala Leu Thr Gly Gly Val Leu Tyr Leu Phe Cys
            115                 120                 125
Gly Leu Leu Ala Leu Val Pro Leu Cys Trp Phe Ala Asn Ile Val Val
            130                 135                 140
Arg Glu Phe Tyr Asp Pro Ser Val Pro Val Ser Gln Lys Tyr Glu Leu
145                 150                 155                 160
Gly Ala Ala Leu Tyr Ile Gly Trp Ala Ala Thr Ala Leu Leu Met Val
                165                 170                 175
Gly Gly Cys Leu Leu Cys Cys Gly Ala Trp Val Cys Thr Gly Arg Pro
            180                 185                 190
Asp Leu Ser Phe Pro Val Lys Tyr Ser Ala Pro Arg Arg Pro Thr Ala
            195                 200                 205
Thr Gly Asp Tyr Asp Lys Lys Asn Tyr Val
            210                 215

<210> SEQ ID NO 99
<211> LENGTH: 218
<212> TYPE: PRT
<213> ORGANISM: Artificial Sequence
<220> FEATURE:
```

```
<223> OTHER INFORMATION: point mutated claudin 5 S151T

<400> SEQUENCE: 99

Met Gly Ser Ala Ala Leu Glu Ile Leu Gly Leu Val Leu Cys Leu Val
1               5                   10                  15

Gly Trp Gly Gly Leu Ile Leu Ala Cys Gly Leu Pro Met Trp Gln Val
            20                  25                  30

Thr Ala Phe Leu Asp His Asn Ile Val Thr Ala Gln Thr Thr Trp Lys
            35                  40                  45

Gly Leu Trp Met Ser Cys Val Val Gln Ser Thr Gly His Met Gln Cys
    50                  55                  60

Lys Val Tyr Asp Ser Val Leu Ala Leu Ser Thr Glu Val Gln Ala Ala
65                  70                  75                  80

Arg Ala Leu Thr Val Ser Ala Val Leu Leu Ala Phe Val Ala Leu Phe
                85                  90                  95

Val Thr Leu Ala Gly Ala Gln Cys Thr Thr Cys Val Ala Pro Gly Pro
            100                 105                 110

Ala Lys Ala Arg Val Ala Leu Thr Gly Gly Val Leu Tyr Leu Phe Cys
            115                 120                 125

Gly Leu Leu Ala Leu Val Pro Leu Cys Trp Phe Ala Asn Ile Val Val
    130                 135                 140

Arg Glu Phe Tyr Asp Pro Thr Val Pro Val Ser Gln Lys Tyr Glu Leu
145                 150                 155                 160

Gly Ala Ala Leu Tyr Ile Gly Trp Ala Ala Thr Ala Leu Leu Met Val
                165                 170                 175

Gly Gly Cys Leu Leu Cys Cys Gly Ala Trp Val Cys Thr Gly Arg Pro
            180                 185                 190

Asp Leu Ser Phe Pro Val Lys Tyr Ser Ala Pro Arg Arg Pro Thr Ala
            195                 200                 205

Thr Gly Asp Tyr Asp Lys Lys Asn Tyr Val
    210                 215
```